US009205069B2

(12) United States Patent
King et al.

(10) Patent No.: US 9,205,069 B2
(45) Date of Patent: *Dec. 8, 2015

(54) INHIBITORS OF ANAPHASE PROMOTING COMPLEX ACTIVITY

(75) Inventors: Randall King, Newton, MA (US); Xing Zeng, Jamaica Plain, MA (US); Shantanu Gaur, Canonsburg, PA (US)

(73) Assignee: President and Fellows of Harvard College, Cambridge, MA (US)

( * ) Notice: Subject to any disclaimer, the term of this patent is extended or adjusted under 35 U.S.C. 154(b) by 469 days.

This patent is subject to a terminal disclaimer.

(21) Appl. No.: 13/254,235

(22) PCT Filed: Mar. 8, 2010

(86) PCT No.: PCT/US2010/026505
§ 371 (c)(1),
(2), (4) Date: Dec. 12, 2011

(87) PCT Pub. No.: WO2010/102281
PCT Pub. Date: Sep. 10, 2010

(65) Prior Publication Data
US 2012/0115948 A1 May 10, 2012

Related U.S. Application Data

(60) Provisional application No. 61/157,942, filed on Mar. 6, 2009.

(51) Int. Cl.
*A61K 31/155* (2006.01)
*A61K 31/18* (2006.01)
*A61K 31/198* (2006.01)

(52) U.S. Cl.
CPC ............ *A61K 31/198* (2013.01); *A61K 31/155* (2013.01); *A61K 31/18* (2013.01)

(58) Field of Classification Search
CPC .............................. A61K 31/155; A61K 31/18
See application file for complete search history.

(56) References Cited

U.S. PATENT DOCUMENTS 6,951,730 B2 10/2005 Small et al.
2005/0203063 A1* 9/2005 Deshaies et al. ............... 514/63

FOREIGN PATENT DOCUMENTS

EP 1469082 A1 10/2004
WO WO-97/19672 A1 6/1997

OTHER PUBLICATIONS

Vodermaier et al. Current Biology, 2003, vol. 13, pp. 1459-1468.*
Keyes et al. Genetics, Jan. 2008, vol. 178, p. 589-591.*
DiStefano et al. "Pharmacological Studies of the Mechanism of Tumor-Induced Bone Marrow Cytolysis." *Cancer Res.* 39.4(1979):1193-1198.
Eisen. "Effect of Hexadimethrine Bromide on Plasma Kinin Formation, Hydrolysis of ρ-Tosyl-L-Arginine Methyl Ester and Fibrinolysis." *Brit. J. Pharm. Chemoth.* 22(1964):87-103.
Fiedler et al. "Activation, Inhibiton, and pH-Dependence of the Hydrolysis α-N-Benzoyl-L-Arginine Ethyl Ester Catalyzed by Kallikrein from Porcine Pancreas." *Eur. J. Biochem.* 7.1(1968):27-33.
Fry et al. "APC/C-mediated Degradation in Early Mitosis:How to Avoid Spindle Assembly Checkpoint Inhibition." *Cell Cycle* 5.14 (2006): 1487-1491.
Verma et al. "Ubistatins Inhibit Proteasome-dependent Degradation by Binding the Ubiquitin Chain." *Science* 306.5693 (2004): 117-120.
Ricard et al. "Proliferation and Agglutinability of Primary and Transformed Human Epithelial Cells in Culture." *J.Cell.Sci.* 21.3 (1976): 553-561.
Fang et al. "The Checkpoint Protein MAD2 and the Mitotic Regulator CDC20 Form a Ternary Complex With the Anaphase-Promoting Complex to Control Anaphase Initiation." *Genes Dev.* 12.12(1998):1871-1883.
Kallio et al. "Mammalian p55CDC Mediates Association of the Spindle Checkpoint Protein Mad2 with the Cyclosome/Anaphase-Promoting Complex, and is Involved in Regulating Anaphase Onset and Late Mitotic Events." *J. Cell. Biol.* 141.6(1998):1393-1406.
Kraft et al. "Mitotic Regulation of the Human Anaphase-Promoting Complex by Phosphorylation." *EMBO J.* 22.24(2003):6598-6609.
Kramer et al. "Activation of the Human Anaphase-Promoting Complex by Proteins of the CDC20/Fizzy Family" *Curr. Biol.* 8.22(1998):1207-1210.
Kramer et al. "Mitotic Regulation of the APC Activator Proteins CDC20 and CDH1." *Mol. Biol. Cell.* 11.5(2000):1555-1569.
NCBI Accession No. AAF05754 dated Nov. 3, 1999.
NCBI Accession No. AAF05755 dated Nov. 3, 1999.
NCBI Accession No. AAH02941 dated Jan. 27, 2004.
NCBI Accession No. AAH05258 dated Nov. 17, 2006.
NCBI Accession No. AAH09496 dated Jan. 27, 2004.
NCBI Accession No. AAH10875 dated Nov. 17, 2006.
NCBI Accession No. AAH10944 dated Nov. 17, 2006.
NCBI Accession No. AAH11656 dated Nov. 17, 2006.
NCBI Accession No. AAH17713 dated Dec. 2, 2006.
NCBI Accession No. AAH98264 dated Jul. 18, 2005.
NCBI Accession No. AAH98295 dated Jul. 18, 2005.
NCBI Accession No. AAH98362 dated Jul. 15, 2004.
NCBI Accession No. AAH99732 dated Aug. 3, 2005.
NCBI Accession No. AAI11799 dated Jan. 17, 2006.
NCBI Accession No. AAI41849 dated May 8, 2007.
NCBI Accession No. AAI48237 dated Oct. 12, 2007.
NCBI Accession No. NP_001072113 dated Jan. 28, 2012.
NCBI Accession No. NP_001107563 dated Jan. 29, 2012.
NCBI Accession No. NP_001247 dated Jan. 29, 2012.
NCBI Accession No. NP_003894 dated Jan. 28, 2012.
NCBI Accession No. NP_004652 dated Nov. 21, 2011.
NCBI Accession No. NP_057322 dated Nov. 27, 2011.

(Continued)

*Primary Examiner* — Samira Jean-Louis
(74) *Attorney, Agent, or Firm* — Mintz Levin Cohn Ferris Glovsky and Popeo, P.C.; Ingrid A. Beattie

(57) ABSTRACT

The invention provides an anti-proliferative composition comprising a non-peptide analog of the C-terminal isoleucine-arginine (IR) tail motif of an activator of an anaphase promoting complex (APC). The invention further provides methods of inhibiting the ubiquitination activity of the APC by administering compositions of the invention.

9 Claims, 8 Drawing Sheets

(56) References Cited

OTHER PUBLICATIONS

NCBI Accession No. Q13042 dated Feb. 22, 2012.
NCBI Accession No. Q9UJX2 dated Feb. 22, 2012.
NCBI Accession No. Q9UJX3 dated Feb. 22, 2012.
Vodermaier et al. "TPR Subunits of the Anaphase-Promoting Complex Mediate Binding to the Activator Protein CDH1." *Curr. Biol.* 13.17(2003):1459-1468.

* cited by examiner

A

B

C

D

United States Patent US 9,205,069 B2

INHIBITORS OF ANAPHASE PROMOTING COMPLEX ACTIVITY

RELATED APPLICATIONS

This application is a national stage application, filed under 35 U.S.C. §371, of International Application No. PCT/US2010/026505, filed Mar. 8, 2010, which claims the benefit of provisional applications U.S. Ser. No. 61/157,942, filed Mar. 6, 2009, the contents of which are incorporated by reference in their entireties.

GOVERNMENT SUPPORT

This invention was made with U.S. Government support under National Institutes of Health grant RO1 GM66492. The Government has certain rights in the invention.

INCORPORATION BY REFERENCE

The contents of the text file named "29297-059001WO_ST25.txt", which was created on Oct. 28, 2010 and is 118 KB in size, are hereby incorporated by reference in their entirety.

FIELD OF THE INVENTION

This invention relates generally to the fields of oncology and disorders associated with cell division.

BACKGROUND OF THE INVENTION

Conventional antiproliferative agents used in the treatment of cancer are generally grouped as compounds which affect the integrity of nucleic acid polymers, e.g., by binding, alkylating, inducing strand breaks, intercalating between base pairs or affecting enzymes which maintain the integrity and function of DNA and RNA, and compounds that bind to proteins to inhibit enzymatic action (e.g., antimetabolites) or the function of structural proteins necessary for cellular integrity (e.g., antitubulin agents). Other antiproliferative drugs include those that block steroid hormone action for the treatment of hormone-dependent cancer, photochemically activated agents, radiation sensitizers, and protectors. Many of these agents are associated with adverse side effects.

SUMMARY OF THE INVENTION

The invention features an anti-proliferative composition comprising a non-peptide analog of the C-terminal isoleucine-arginine (IR) motif of an activator of an anaphase promoting complex (APC) such as Cdc20 or Cdh1. For example, the consensus sequence for vertebrate cdc20 is I, H, Q, G/S, I, R, and the consensus sequence for cdh1 is L, F, T, R, I, R, and conserved region of Cdh1 also extends further upstream Preferably, the compound is formulated in a pharmaceutical composition, i.e., in the presence of physiologically-acceptable excipients. A peptide is a polymer of at least two amino acids. A non-peptide compound or IR motif analog is a composition that comprises less than two amino acids; such a compound may include one amino acid or no amino acids. For example, the non-peptide compound or IR motif analog is tosyl-L-arginine methylester (TAME). Other compounds in this class include, tosyl-L-arginine amide (TAA), tosyl-L-lysine methylester (TLME), tosyl-L-arginine (TAOH), acetyl-L-arginine methylester (AAME), Benzoyl-L-arginine amide (BAA), tosyl-L-arginine t-butyl-ester (TATE), or Benzoyl-L-arginine methylester (BAME).

Members of this class of compounds inhibits degradation of a substrate of an APC in a cell such as a human cell or population of cells characterized as aberrantly proliferating. The compounds are useful to treat cellular proliferative disorders such as cancers, e.g., skin cancer, viral induced hyperproliferative HPV-papiloma, HSV-shingles, colon cancer, bladder cancer, breast cancer, melanoma, ovarian carcinoma, prostate carcinoma, or lung cancer as well as psoriasis and eczema. The compounds may be also useful in the context of in vitro fertilization, because they enhance the ability of these early embryos to properly segregate DNA during mitosis.

The compound contacts a component of a tetratricopeptide repeats (TPR) subcomplex of an APC. For example, a TPR subcomplex is composed of APC3/Cdc27, APC6, APC7, and APC8. The compound induces a cell cycle checkpoint such as the spindle assembly checkpoint (SAC). The compound contacts at least one amino acid of said APC3 polypeptide of SEQ ID NO: 1, 2, or 3. In other examples, the compound contacts at least one amino acid of the APC6 polypeptide of SEQ ID NO: 4, 5, 6, or 7; at least one amino acid of the APC7 polypeptide of SEQ ID NO: 9, 10, 11, 12, 13, 14, 15, 16, 17, 18, or 19; at least one amino acid of the APC8 polypeptide of SEQ ID NO: 20, 21, 22, 23, 24, or 25; at least one amino acid of the APC3 polypeptide of SEQ ID NO: 1, 2, or 3 and at least one amino acid of the APC7 polypeptide of SEQ ID NO: 9, 10, 11, 12, 13, 14, 15, 16, 17, 18, or 19. The compound further further contacts at least one amino acid of the APC6 polypeptide of SEQ ID NO: 4, 5, 6, or 7; at least one amino acid of the APC8 polypeptide of SEQ ID NO: 20, 21, 22, 23, 24, or 25; or at least one amino acid of the APC6 polypeptide of SEQ ID NO: 4, 5, 6, or 7 and contacts at least one amino acid of the APC8 polypeptide of SEQ ID NO: 20, 21, 22, 23, 24, or 25.

A method for inhibiting a ubiquitination activity of an APC is carried out by administering an effective amount of an analog of the C-terminal IR motif of an activator of an APC to a cell to inhibit the degradation of a substrate of an APC or to to induce a cell cycle checkpoint. The analog contacts a component of a tetratricopeptide repeats (TPR) subcomplex of an APC such as APC3/Cdc27, APC6, APC7, or APC8.

An IR tail analog that inhibits APC is useful to identify other antiproliferative agents the mechanism of which involve the same or similar contact regions of the APC. Accordingly, a method of identifying an antiproliferative agent is carried out by contacting an APC complex with a candidate compound in the presence of TAME (and in the absence of TAME as a control. A decrease in binding of the candidate compound to the APC in the presence of TAME compared to the level of binding in its absence indicates that the compound interferes with the APC in a manner analogous to TAME and therefore inhibits cell proliferation.

A method of screening for a small molecule inhibitor of an APC includes the steps of (a) identifying a test compound, wherein the test compound is an analog of an IR motif; (b) combining either the test compound or a control compound with an activated APC and at least one labeled substrate of APC; and (c) determining the amount of labeled substrate present following the addition of either the test compound or the control compound. An increase in the amount of the labeled substrate following the addition of the test compound compared to the amount of labeled substrate present following the addition of the control compound indicates that the test compound inhibits an activity of APC. The control compound is not an analog of an IR motif. The combining step occurs in vivo, in vitro, or ex vivo. An example of a labeled substrate is cyclin B-luciferase.

The compositions describes herein are useful in treating a cell cycle disorder. The compounds are administered to a subject in need thereof in an effective amount to inhibit an activity of an anaphase promoting complex (APC). For example, the compounds activate a cell cycle checkpoint such as the SAC. Optionally, a second chemotherapeutic compound is administered.

One advantage of APC inhibitors is that they are much less toxic than other antiproliferative agents since they do not disrupt other processes (e.g., damage DNA or microtubules).

Publications, U.S. patents and applications, GEN-BANK™/NCBI accession numbers, and all other references cited herein, are hereby incorporated by reference.

DETAILED DESCRIPTION

Figure 1:
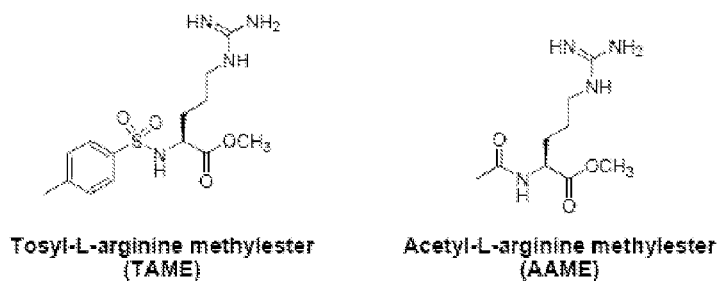
FIG. 1A is a schematic diagram representing the structure of TAME and AAME.
FIG. 1B is a Western Blot showing that TAME but not AAME establishes mitotic arrest in *Xenopus* extract as indicated by stabilization of Cdc27 phosphorylation and cyclin B.
FIG. 1C is a Western Blot showing that TAME inhibits activation of APC-Cdc20 but does not directly inhibit the ligase activity. APC was immunoprecipitated from mitotic extract and tested in an in vitro ubiquitination assay. Adding 200 μM TAME but not AAME into the extract inhibited APC activity. Adding 200 μM TAME or AAME into the ubiquitination reaction system did not inhibit APC.
FIG. 1D is a Western Blot showing that TAME inhibits activation of APC-Cdh1 but does not directly inhibit the ligase activity. Interphase extract was pre-incubated with 200 μM TAME or AAME for 30 minutes before addition of recombinant Cdh1. APC was then immunoprecipitated and tested in an in vitro ubiquitination assay. Pre-incubation with TAME but not AAME inhibited APC activity. Adding 200 μM TAME or AAME into the ubiquitination reaction system did not inhibit APC.
Figure 1:
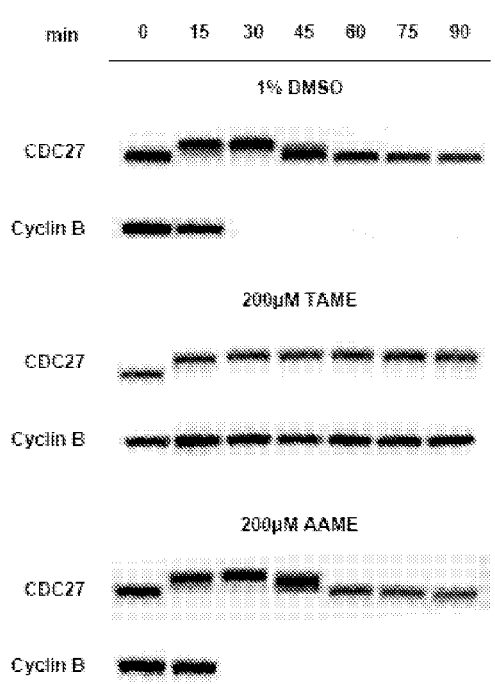
Figure 1:
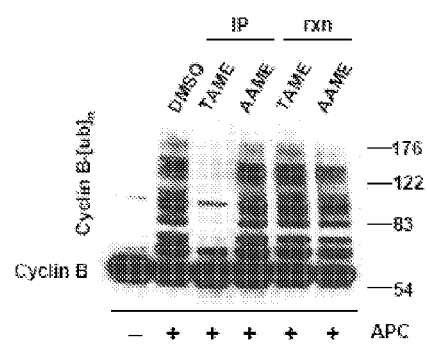
Figure 1:
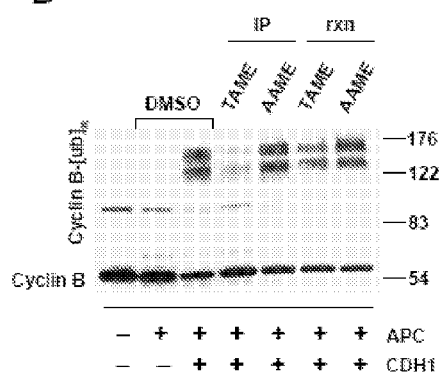

The invention provides the first reported small molecule inhibitor of the APC. The Anaphase-Promoting Complex (APC) is a multisubunit ubiquitin ligase that regulates the timing of mitotic exit and the G1/S transition. In prometaphase, the APC is activated by Cdc20, leading to ubiquitination and degradation of Nek2A and cyclin A. However, ubiquitination of other APC substrates is inhibited by the Spindle Assembly Checkpoint (SAC) until chromosomes have achieved proper bipolar attachment to the mitotic spindle. Once the SAC is satisfied, ubiquitination and degradation of securin and cyclin B lead to chromosome segregation and mitotic exit. In telophase, another APC activator, Cdh1, replaces Cdc20 and maintains APC activity during G1.

Cdc20 and Cdh1 activate the APC and are important for recruiting substrates to the APC. The activator proteins share several evolutionarily conserved motifs, including an N-terminal C-box (comprising the consensus sequence DRFY-IPXR and SEQ ID NO: 26), seven WD40 repeats (also known as WD or beta-transducin repeats of about 40 amino acids, often terminating in a WD dipeptide and containing 4-16 repeating units that together form a circular beta-propellar structure), and a C-terminal IR tail (a C-terminal region including one or more IR dipeptide motifs). Whereas the WD40 domain may interact simultaneously with substrates and the APC, the C-box and the IR tail are specifically involved in APC binding. The IR tail of Cdh1 interacts with multiple APC subunits, including Cdc27 and Apc7. Deletion of the IR tail of Cdh1 compromises its ability to activate human APC in vitro, and is lethal in budding yeast lacking Sic1. However, deletion of IR tail of Cdc20 does not affect the viability of wild-type budding yeast, and thus, does not seem to be strictly required for APC activation. Instead, the IR tail may be important for regulating Cdc20 abundance, as Cdc20ΔIR accumulates to higher levels than the wild-type protein. Thus while the IR tail seems to be critical for Cdh1 recruitment and activation of the APC, the specific role of Cdc20's IR tail in APC binding and activation remains unclear.

Phenotypic chemical genetic screens identify small molecules that are useful for dissecting the regulation of complex systems as well as novel targets for drug development. However, determining the precise mechanism of action of compounds discovered in phenotypic screens can be challenging. Method of the invention identify APC as the target of a small molecule discovered in a phenotypic screen for inhibitors of cyclin proteolysis in Xenopus extracts and use this compound as a tool to study APC regulation in Xenopus extracts and human cells.

The methods of the invention are used to show that TAME, a compound identified previously in a high-throughput screen for inhibitors of cyclin proteolysis in Xenopus extracts (Verna, R. et al. 2004. Science 306(5693):117), blocks APC activation by competitively inhibiting the association of the IR tail of Cdc20 and Cdh1 with the APC. The data provided indicate that the IR tail of Cdc20 is critical for binding to the APC in mitotic Xenopus extract. The requirement for an IR-dependent recruitment mechanism stems from the dynamic nature of Cdc20 binding to mitotic APC. There is an activity in mitotic Xenopus extracts that actively dissociates Cdc20 from the APC, thereby sensitizing the system to the inhibitory effects of TAME. Because Cdh1 binding to interphase APC is not dynamic, TAME is a less effective inhibitor of Cdh1 association with interphase APC in the Xenopus system.

A key aspect of TAME function is that it can inhibit APC activation without activating the spindle checkpoint. For example, TAME blocks APC activation in the Xenopus system which lacks an intact spindle checkpoint. However in mammalian cells, a cell-permeable derivative of the compound arrests cells in mitosis through two mechanisms: direct APC inhibition, and by preventing inactivation of the spindle checkpoint.

The discovery of TAME's mechanism of action sheds new light on how Cdc20 binding to the APC is regulated. It has been found that Cdc20 associates with interphase APC in Xenopus extracts, conflicting with previous reports suggesting that APC must be mitotically phosphorylated to interact with Cdc20 (Kraft, C. et al. 2003. EMBO J. 22(24):6598; Kramer, E. R. et al. 2000. Mol Biol Cell. 11(5): 1555). One difference is that association of endogenous Xenopus Cdc20 rather than exogenous protein was examined in the present experiments (Kramer, E. R. et al. 2000. Mol Biol Cell. 11(5): 1555). Factors present in extracts or cells, such as chaperones involved in folding of Cdc20, may therefore be important for efficient loading of Cdc20 onto interphase APC. However, in agreement with others, it was observed that the steady state level of Cdc20 bound to the APC increases during mitosis Fang, G. et al. 1998. Genes Dev. 12(12):1871; Kallio, M. et al. 1998. J Cell Biol 141(6), 1393; Kramer, E. R. et al. 1998. Curr Biol. 8(22), 1207). Provided the results of the experiments described herein demonstrating that the rate of Cdc20 dissociation increases in mitosis, there must also be a corresponding increase in the rate of Cdc20 association with the APC during mitosis, which may require mitotic phosphorylation of APC or Cdc20 (Kraft, C. et al. 2003. EMBO J. 22(24):6598; Kramer, E. R. et al. 2000. Mol Biol Cell. 11(5): 1555). The observed dissociation phenomenon also explains why Cdc20 association with kinetochores during mitosis is also highly dynamic, and why Cdc20 exists predominantly in a high molecular weight complex during interphase with a free pool of Cdc20 appearing in mitosis.

Despite a common biochemical target, TAME induces mitotic arrest through distinct mechanisms in Xenopus extract and mammalian cells. Whereas mitotic arrest in Xenopus extracts is a consequence of inhibition of Cdc20 association with the APC, the arrest in mammalian cells depends partially on the SAC, and occurs despite only a 30% reduction in Cdc20 bound to the APC.

APC Proteins

Pharmaceutical compositions and compounds of the invention comprise an analog of the C-terminal IR motif of an activator of an APC. Thus, analogs of the invention contact one or proteins of the APC. In one aspect of the invention, analogs bind one or proteins of the APC either reversibly or irreversibly. In another aspect of the invention, one or more analogs bind one or proteins of the APC either reversibly or irreversibly. Alternatively or in addition, analogs of the invention contact or bind multiple proteins of the APC. In a preferred embodiment of the invention, analogs contact or bind discrete three dimensional surfaces that are exposed to the C-terminal IR motif of an activator of an APC. Contemplated exposed three dimensional surfaces are comprised of sequences that are either contiguous or not contiguous within the amino acid sequences provided below.

Essential amino acids required for binding to a C-terminal IR motif of an activator of an APC or analog of the invention thereof are determined by deletion or substitution analysis, wherein the elimination of binding between an analog or APC activator and at least one APC protein indicates that the eliminated or substituted amino acid is essential to the binding of that analog or activator of the APC. Methods of deleting and substituting amino acids within the APC polypeptide sequences below and determining the binding efficacy of an activator of the APC or analog thereof can be performed by routine methods known to those of ordinary skill in the art. Finally, all polynucleotide sequences that encode the polypeptide sequences provided herein, are encompassed by the invention.

Human APC3/CDC27, isoform 1, is encoded by the following amino acid sequence (NCBI Accession No. NP_001107563 and SEQ ID NO: 1):

```
  1 mtvlqepvqa aiwqalnhya yrdavflaer lyaevhseea lfllatcyyr sgkaykayrl
 61 lkghscttpq ckyllakccv dlsklaegeq ilsggvfnkq kshddivtef gdsacftlsl
121 lghvycktdr lakgsecyqk slslnpflws pfeslceige kpdpdqtfkf tslqnfsncl
181 pnscttqvpn hslshrqpet vltetpqdti elnrlnless nskyslntds svsyidsavi
241 spdtvplgtg tsilskqvqn kpktgrsllg gpaalspltp sfgilpletp spgdgsylqn
301 ytntppvidv pstgapskkt frvlqsvari gqtgtksvfs qsgnsrevtp ilaqtqssgp
361 qtsttpqvls ptitsppnal prrssrlfts dssttkensk klkmkfppki pnrktksktn
421 kggitqpnin dsleitklds siisegkist itpqiqafnl qkaaaeglms llremgkgyl
481 alcsynckea inilshlpsh hyntgwvlcq igrayfelse ymqaerifse vrrienyrve
541 gmeiysttlw hlqkdvalsv lskdltdmdk nspeawcaag ncfslqrehd iaikffqrai
601 qvdpnyayay tllghefvlt eeldkalacf rnairvnprh ynawyglgmi yykqekfsla
661 emhfqkaldi npqssvllch igvvqhalkk sekaldtlnk aividpknpl ckfhrasvlf
721 anekyksalq eleelkqivp keslvyflig kvykklgqth lalmnfswam dldpkgannq
781 ikeaidkryl pddeepitqe eqimgtdesq essmtdaddt qlhaaesdef
```

Human APC3/CDC27, isoform 2, is encoded by the following amino acid sequence (NCBI Accession No. NP_001247 and SEQ ID NO: 2):

```
  1 mtvlqepvqa aiwqalnhya yrdavflaer lyaevhseea lfllatcyyr sgkaykayrl
 61 lkghscttpq ckyllakccv dlsklaegeq ilsggvfnkq kshddivtef gdsacftlsl
121 lghvycktdr lakgsecyqk slslnpflws pfeslceige kpdpdqtfkf tslqnfsncl
181 pnscttqvpn hslshrqpet vltetpqdti elnrlnless nskyslntds svsyidsavi
241 spdtvplgtg tsilskqvqn kpktgrsllg gpaalspltp sfgilpletp spgdgsylqn
301 ytntppvidv pstgapskks varigqtgtk svfsqsgnsr evtpilaqtq ssgpqtsttp
361 qvlsptitsp pnalprrssr lftsdssttk enskklkmkf ppkipnrktk sktnkggitq
421 pnindsleit kldssiiseg kistitpqiq afnlqkaaae glmsllremg kgylalcsyn
481 ckeainilsh lpshhyntgw vlcqigrayf elseymqaer ifsevrrien yrvegmeiys
541 ttlwhlqkdv alsvlskdlt dmdknspeaw caagncfslq rehdiaikff qraiqvdpny
601 ayaytllghe fvlteeldka lacfrnairv nprhynawyg lgmiyykqek fslaemhfqk
661 aldinpqssv llchigvvqh alkksekald tlnkaividp knplckfhra svlfanekyk
721 salqeleelk qivpkeslvy fligkvykkl gqthlalmnf swamdldpkg annqikeaid
781 krylpddeep itqeeqimgt desqessmtd addtqlhaae sdef
```

Human APC3/CDC27 is encoded by the following amino acid sequence (NCBI Accession No. AAH11656 and SEQ ID NO: 3):

```
  1 mtvlqepvqa aiwqalnhya yrdavflaer lyaevhseea lfllatcyyr sgkaykayrl
 61 lkghscttpq ckyllakccv dlsklaegeq ilsggvfnkq kshddivtef gdsacftlsl
121 lghvycktdr lakgsecyqk slslnpflws pfeslceige kpdpdqtfkf tslqnfsncl
181 pnscttqvpn hslshrqpet vltetpqdti elnrlnless nskyslntds svsyidsavi
241 spdtvplgtg tsilskqvqn kpktgrsllg gpaalspltp sfgilpletp spgdgsylqn
301 ytntppvidv pstgapskkt frvlqsvari gqtgtksvfs qsgnsrevtp ilaqtqssgp
361 qtsttpqvls ptitsppnal prrssrlfts dssttkensk klkmkfppei pnrktksktn
421 kggitqpnin dsleitklds siisegkist itpqiqafnl qkaaaeglms llremgkgyl
481 alcsynckea inilslhpsh hyntgwvlcq igrayfelse ymqaerifse vrrienyrve
541 gmeiyssttlw hlqkdvalsv lskdltdmdk nspeawcaag ncfslqrehd iaikffqrai
601 qvdpnyayay tllghefvlt eeldkalacf rnairvnprh ynawyglgmi yykqekfsla
661 emhfqkaldi npqssvllch igvvqhalkk sekaldtlnk aividpknpl ckfhrasvlf
721 anekyksalq eleelkqivp keslvyflig kvykklgqth lalmnfswam dldpkgannq
781 ikeaidkryl pddeepitqe eqimgtdesq essmtdaddt qlhaaesdef
```

Human APC6/CDC16 is encoded by the following amino acid sequence (NCBI Accession No. AAH10875 and SEQ ID NO: 4):

```
  1 meepinkrlf ekylkdesgf kdpssdwems qssikssicl lrgkiydald nrtlatysyk
 61 ealkldvycf eafdlltshh mltaqeekel leslplsklc neeqellrfl fenklkkynk
121 psetvipesv dglqenldvv vslaerhyyn cdfkmcyklt svvmekdpfh asclpvhigt
181 lvelnkanel fylshklvdl ypsnpvswfa vgcyylmvgh kneharryls kattlektyg
241 pawiayghsf avesehdqam aayftaaqlm kgchlpmlyi gleygltnns klaerffsqa
301 lsiapedpfv mhevgvvafq ngewktaekw fldalekika ignevtvdkw epllnnlghv
361 crklkkyaea ldyhrqalvl ipqnastysa igyihslmgn fenavdyfht alglrrddtf
421 svtmlghcie myigdseayi gadikdklkc ydfdvhtmkt lkniisppwd frefevekqt
481 aeetgltple tsrktpdsrp sleetfeiem nesdmmlets msdhst
```

Human APC6/CDC16 is encoded by the following amino acid sequence (NCBI Accession No. NP_001072113 and SEQ ID NO: 5):

```
  1 mnlerlrkrv rqyldqqqyq salfwadkva slsreepqdi ywlaqclylt aqyhraahal
 61 rsrkldklye acrylaarch yaakehqqal dvldmeepin krlfekylkd esgfkdpssd
121 wemsqssiks sicllrgkiy daldnrtlat ysykealkld vycfeafdll tshhmltaqe
181 ekelleslpl sklcneeqel lrflfenklk kynkpsetvi pesvdglqen ldvvvslaer
241 hyyncdfkmc ykltsvvmek dpfhasclpv higtivelnk anelfylshk lvdlypsnpv
301 swfavgcyyl mvghknehar rylskattle ktygpawiay ghsfaveseh dqamaayfta
361 aqlmkgchlp mlyigleygl tnnsklaerf fsqalsiape dpfvmhevgv vafqngewkt
421 aekwfldale kikaignevt vdkwepllnn lghvcrklkk yaealdyhrq alvlipqnas
481 tysaigyihs lmgnfenavd yfhtalglrr ddtfsvtmlg hciemyigds eayigadikd
```

```
541 klkcydfdvh tmktlkniis ppwdfrefev ekqtaeetgl tpletsrktp dsrpsleetf 601 eiemnesdmm letsmsdhst
```

Human APC6/CDC16 is encoded by the following amino acid sequence (NCBI Accession No. NP_003894 and SEQ ID NO: 6):

```
  1 mnlerlrkrv rqyldqqqyq salfwadkva slsreepqdi ywlaqclylt aqyhraahal 61 rsrkldklye acrylaarch yaakehqqal dvldmeepin krlfekylkd esgfkdpssd 121 wemsqssiks sicllrgkiy daldnrtlat ysykealkld vycfeafdll tshhmltaqe 181 ekelleslpl sklcneeqel lrflfenklk kynkpsetvi pesvdglqen ldvvvslaer 241 hyyncdfkmc ykltsvvmek dpfhasclpv higtlvelnk anelfylshk lvdlypsnpv 301 swfavgcyyl mvghknehar rylskattle ktygpawiay ghsfaveseh dqamaayfta 361 aqlmkgchlp mlyigleygl tnnsklaerf fsqalsiape dpfvmhevgv vafqngewkt 421 aekwfldale kikaignevt vdkwepllnn lghvcrklkk yaealdyhrq alvlipqnas 481 tysaigyihs lmgnfenavd yfhtalglrr ddtfsvtmlg hciemyigds eayigadikd 541 klkcydfdvh tmktlkniis ppwdfrefev ekqtaeetgl tpletsrktp dsrpsleetf 601 eiemnesdmm letsmsdhst
```

Human APC6/CDC16 is encoded by the following amino acid sequence (NCBI Accession No. Q13042 and SEQ ID NO: 7):

```
  1 mnlerlrkrv rqyldqqqyq salfwadkva slsreepqdi ywlaqclylt aqyhraahal 61 rsrkldklye acrylaarch yaakehqqal dvldmeepin krlfekylkd esgfkdpssd 121 wemsqssiks sicllrgkiy daldnrtlat ysykealkld vycfeafdll tshhmltaqe 181 ekelleslpl sklcneeqel lrflfenklk kynkpsetvi pesvdglqen ldvvvslaer 241 hyyncdfkmc ykltsvvmek dpfhasclpv higtivelnk anelfylshk lvdlypsnpv 301 swfavgcyyl mvghknehar rylskattle ktygpawiay ghsfaveseh dqamaayfta 361 aqlmkgchlp mlyigleygl tnnsklaerf fsqalsiape dpfvmhevgv vafqngewkt 421 aekwfldale kikaignevt vdkwepllnn lghvcrklkk yaealdyhrq alvlipqnas 481 tysaigyihs lmgnfenavd yfhtalglrr ddtfsvtmlg hciemyigds eayigadikd 541 klkcydfdvh tmktlkniis ppwdfrefev ekqtaeetgl tpletsrktp dsrpsleetf 601 eiemnesdmm letsmsdhst
```

Human APC7 is encoded by the following amino acid sequence (NCBI Accession No. AAH98362 and SEQ ID NO: 8):

```
  1 nvidhvrdma aaglhsnvrl lsslllltmsn nnpelfsppq kyqllvyhad slfhdkeyrn 61 ayskytmalq qkkalsktsk vrpstgnsas tpqsqclpse ievkykmaec ytmlkqdkda 121 iaildgipsr qrtpkinmml anlykkagqe rpsvtsykev lrqcplalda ilgllslsvk 181 gaevasmtmn viqtvpnldw lsvwikayaf vhtgdnsrai sticslekks llrdnvdllg 241 sladlyfrag dnknsvlkfe qaqmldpyli kgmdvygyll aregrledve nlgcrlfnis 301 dqhaepwvvs gchsfyskry sralylgaka iqlnsnsvqa lllkgaalrn mgrvqeaiih
```

```
361 freairlapc rldcyeglie cylasnsire amvmannvyk tlganaqtlt llatvcledp 421 vtgekaktll dkaltqrpdy ikavvkkael lsreqkyedg iallrnalan qsdcvlhril 481 gdflvavney qeamdqysia lsldpndqks legmqkmeke esptdatqee dvddmegsge 541 egdlegsdse aaqwadqeqw fgmq
```

Human APC7 is encoded by the following amino acid sequence (NCBI Accession No. AAH98264 and SEQ ID NO: 10 X):

```
  1 nvidhvrdma aaglhsnvrl lssllltmsn nnpelfsppq kyqllvyhad slfhdkeyrn 61 ayskytmalq qkkalsktsk vrpstgnsas tpqsqclpse ievkykmaec ytmlkqdkda 121 iaildgipsr qrtpkinmml anlykkagqe rpsvtsykev lrqcplalda ilgllslsvk 181 gaevasmtmn viqtvpnldw lsvwikayaf vhtgdnsrai sticslekks llrdnvdllg 241 sladlyfrag dnknsvlkfe qaqmldpyli kgmdvygyll aregrledve nlgcrlfnis 301 dqhaepwvvs gchsfyskry sralylgaka iqlnsnsvqa lllkgaalrn mgrvqeaiih 361 freairlapc rldcyeglie cylasnsire amvmannvyk tlganaqtlt llatvcledp 421 vtgekaktll dkaltqrpdy ikavvkkael lsreqkyedg iallrnalan qsdcvlhril 481 gdflvavney qeamdqysia lsldpndqks legmqkmeke esptdatqee dvddmegsge 541 egdlegsdse aaqwadqeqw fgmq
```

Human APC7 is encoded by the following amino acid sequence (NCBI Accession No. AAH98295 and SEQ ID NO: 10):

```
  1 nvidhvrdma aaglhsnvrl lssllltmsn nnpelfsppq kyqllvyhad slfhdkeyrn 61 avskytmalq qkkalsktsk vrpstgnsas tpqsqclpse ievkykmaec ytmlkqdkda 121 iaildgipsr qrtpkinmml anlykkagqe rpsvtsykev lrqcplalda ilgllslsvk 181 gaevasmtmn viqtvpnldw lsvwikayaf vhtgdnsrai sticslekks llrdnvdllg 241 sladlyfrag dnknsvlkfe qaqmldpyli kgmdvygyll aregrledve nlgcrlfnis 301 dqhaepwvvs gchsfyskry sralylgaka iqlnsnsvqa lllkgaalrn mgrvqeaiih 361 freairlapc rldcyeglie cylasnsire amvmannvyk tlganaqtlt llatvcledp 421 vtgekaktll dkaltqrpdy ikavvkkael lsreqkyedg iallrnalan qsdcvlhril 481 gdflvavney qeamdqysia lsldpndqks legmqkmeke esptdatqee dvddmegsge 541 egdlegsdse aaqwadqeqw fgmq
```

Human APC7 is encoded by the following amino acid sequence (NCBI Accession No. AAH99732 and SEQ ID NO: 11):

```
  1 nvidhvrdma aaglhsnvrl lssllltmsn nnpelfsppq kyqllvyhad slfhdkeyrn 61 avskytmalq qkkalsktsk vrpstgnsas tpqsqclpse ievkykmaec ytmlkqdkda 121 iaildgipsr qrtpkinmml anlykkagqe rpsvtsykev lrqcplalda ilgllslsvk 181 gaevasmtmn viqtvpnldw lsvwikayaf vhtgdnsrai sticslekks llrdnvdllg 241 sladlyfrag dnknsvlkfe qaqmldpyli kgmdvygyll aregrledve nlgcrlfnis 301 dqhaepwvvs gchsfyskry sralylgaka iqlnsnsvqa lllkgaalrn mgrvqeaiih 361 freairlapc rldcyeglie cylasnsire amvmannvyk tlganaqtlt llatvcledp
```

-continued

```
421 vtqekaktll dkaltqrpdy ikavvkkael lsreqkyedg iallrnalan qsdcvlhril 481 gdflvavney qeamdqysia lsldpndqks legmqkmeke esptdatqee dvddmegsge 541 egdlegsdse aaqwadqeqw fgmq
```

Human APC7 is encoded by the following amino acid sequence (NCBI Accession No. AAI41849 and SEQ ID NO: 12):

```
  1 mnvidhvrdm aaaglhsnvr llsslllltms nnnpelfspp qkyqllvyha dslfhdkeyr 61 navskytmal qqkkalskts kvrpstgnsa stpqsqclps eievkykmae cytmlkqdkd 121 aiaildgips rqrtpkinmm lanlykkagq erpsvtsyke vlrqcplald ailgllslsv 181 kgaevasmtm nviqtvpnld wlsvwikaya fvhtgdnsra isticslekk sllrdnvdll 241 gsladlyfra gdnknsvlkf eqaqmldpyl ikgmdvygyl laregrledv enlgcrlfni 301 sdqhaepwvv sgchsfyskr ysralylgak aiqlnsnsvq alllkgaalr nmgrvqeaii 361 hfreairlap crldcyegli ecylasnsir eamviannvy ktlganaqtl tllatvcled 421 pvtqekaktl ldkaltqrpd yikavvkkae llsreqkyed giallrnala nqsdcvlhri 481 lgdflvavne yqeamdqysi alsldpndqk slegmqkmek eesptdatqe edvddmegsg 541 eegdlegsds eaaqwadqeq wfgmq
```

Human APC7 is encoded by the following amino acid sequence (NCBI Accession No. AAI11799 and SEQ ID NO: 13):

```
  1 nvidhvrdma aaglhsnvrl lsslllltmsn nnpelfsppq kyqllvyhad slfhdkeyrn 61 avskytmalq qkkalsktsk vrpstgnsas tpqsqclpse ievkykmaec ytmlkqdkda 121 iaildgipsr qrtpkinmml anlykkagqe rpsvtsykev lrqcplalda ilgllslsvk 181 gaevasmtmn viqtvpnldw lsvwikayaf vhtgdnsrai sticslekks llqdnvdllg 241 sladlyfrag dnknsvlkfe qaqmldpyli kgmdvygyll aregrledve nlgcrlfnis 301 dqhaepwvvs gchsfyskry sralylgaka iqlnsnsvqa lllkgaalrn mgrvqeaiih 361 freairlapc rldcyeglie cylasnsire amvmannvyk tlganaqtlt llatvcledp 421 vtqekaktll dkaltqrpdy ikavvkkael lsreqkyedg iallrnalan qsdcvlhril 481 gdflvavney qeamdqysia lsldpndqks legmqkmeke esptdatqee dvddmegsge 541 egdlegsdse aaqwadqeqw fgm
```

Human APC7 is encoded by the following amino acid sequence (NCBI Accession No. AAI48237 and SEQ ID NO: 14):

```
  1 mnvidhvrdm aaaglhsnvr llsslllltms nnnpelfspp qkyqllvyha dslfhdkeyr 61 navskytmal qqkkalskts kvrpstgnsa stpqsqclps eievkykmae cytmlkqdkd 121 aiaildgips rqrtpkinmm lanlykkagq erpsvtsyke vlrqcplald ailgllslsv 181 kgaevasmtm nviqtvpnld wlsvwikaya fvhtgdnsra isticslekk sllqdnvdll 241 gsladlyfra gdnknsvlkf eqaqmldpyl ikgmdvygyl laregrledv enlgcrlfni 301 sdqhaepwvv sgchsfyskr ysralylgak aiqlnsnsvq alllkgaalr nmgrvqeaii 361 hfreairlap crldcyegli ecylasnsir eamvmannvy ktlganaqtl tllatvcled
```

-continued

```
421 pvtqekaktl ldkaltqrpd yikavvkkae llsreqkyed giallrnala nqsdcvlhri 481 lgdflvavne yqeamdqysi alsldpndqk slegmqkmek eesptdatqe edvddmegsg 541 eegdlegsds eaaqwadqeq wfgm
```

Human APC7 is encoded by the following amino acid sequence (NCBI Accession No. NP_057322 and SEQ ID NO: 15):

```
  1 mnvidhvrdm aaaglhsnvr llsslllltms nnnpelfspp qkyqllvyha dslfhdkeyr 61 navskytmal qqkkalskts kvrpstgnsa stpqsqclps eievkykmae cytmlkqdkd 121 aiaildgips rqrtpkinmm lanlykkagr erpsvtsyke vlrqcplald ailgllslsv 181 kgaevasmtm nviqtvpnld wlsvwikaya fvhtgdnsra isticslekk sllrdnvdll 241 gsladlyfra gdnknsvlkf eqaqmldlyl ikgmdvygyl laregrledv enlgcrlfni 301 sdqhaepwvv sgchsfyskr ysralylgak aiqlnsnsvq alllkgaalr nmgrvqeaii 361 hfreairlap crldcyegli ecylasnsir eamvmannvy ktlganaqtl tllatvcled 421 pvtqekaktl ldkaltqrpd yikavvkkae llsreqkyed giallrnala nqsdcvlhri 481 lgdflvavne yqeamdqysi alsldpndqk slegmqkmek eesptdatqe edvddmegsg 541 eegdlegsds eaaqwadqeq wfgmq
```

Human APC7 is encoded by the following amino acid sequence (NCBI Accession No. Q9UJX3 and SEQ ID NO: 16):

```
  1 mnvidhvrdm aaaglhsnvr llsslllltms nnnpelfspp qkyqllvyha dslfhdkeyr 61 navskytmal qqkkalskts kvrpstgnsa stpqsqclps eievkykmae cytmlkqdkd 121 aiaildgips rqrtpkinmm lanlykkagq erpsvtsyke vlrqcplald ailgllslsv 181 kgaevasmtm nviqtvpnld wlsvwikaya fvhtgdnsra isticslekk sllrdnvdll 241 gsladlyfra gdnknsvlkf eqaqmldpyl ikgmdvygyl laregrledv enlgcrlfni 301 sdqhaepwvv sgchsfyskr ysralylgak aiqlnsnsvq alllkgaalr nmgrvqeaii 361 hfreairlap crldcyegli ecylasnsir eamvmannvy ktlganaqtl tllatvcled 421 pvtqekaktl ldkaltqrpd yikavvkkae llsreqkyed giallrnala nqsdcvlhri 481 lgdflvavne yqeamdqysi alsldpndqk slegmqkmek eesptdatqe edvddmegsg 541 eegdlegsds eaaqwadqeq wfgmq
```

Human APC7 is encoded by the following amino acid sequence (NCBI Accession No. AAF05754 and SEQ ID NO: 17):

```
  1 mnvidhvrdm aaaglhsnvr llsslllltms nnnpelfspp qkyqllvyha dslfhdkeyr 61 navskytmal qqkkalskts kvrpstgnsa stpqsqclps eievkykmae cytmlkqdkd 121 aiaildgips rqrtpkinmm lanlykkagr erpsvtsyke vlrqcplald ailgllslsv 181 kgaevasmtm nviqtvpnld wlsvwikaya fvhtgdnsra isticslekk sllrdnvdll 241 gsladlyfra gdnknsvlkf eqaqmldlyl ikgmdvygyl laregrledv enlgcrlfni 301 sdqhaepwvv sgchsfyskr ysralylgak aiqlnsnsvq alllkgaalr nmgrvqeaii 361 hfreairlap crldcyegli ecylasnsir eamvmannvy ktlganaqtl tllatvcled 421 pvtqekaktl ldkaltqrpd yikavvkkae llsreqkyed giallrnala nqsdcvlhri
```

-continued

```
481 lgdflvavne yqeamdqysi alsldpndqk slegmqkmek eesptdatqe edvddmegsg 541 eegdlegsds eaaqwadqeq wfgmq
```

Human APC7 is encoded by the following amino acid sequence (NCBI Accession No. AAH02941 and SEQ ID NO: 18):

```
  1 dnknsvlkfe qaqmldpyli kgmdvygyll aregrledve nlgcrlfnis dqhaepwvvs 61 gchsfyskry sralylgaka iqlnsnsvqa lllkgaalrn mgrvqeaiih freairlapc 121 rldcyeglie cylasnsire amvmannvyk tlganaqtlt llatvcledp vtqekaktll 181 dkaltqrpdy ikavvkkael lsreqkyedg iallrnalan qsdcvlhril gdflvavney 241 qeamdqysia lsldpndqks legmqkmeke esptdatqee dvddmegsge egdlegsdse 301 aaqwadqeqw fgmq
```

Human APC7 is encoded by the following amino acid sequence (NCBI Accession No. AAH09498 and SEQ ID NO: 19):

```
  1 ecytmlkqdk daiaildgip srqrtpkinm mlanlykkag qerpsvtsyk evlrqcplal 61 dailgllsls vkgaevasmt mnviqtvpnl dwlsvwikay afvhtgdnsr aisticslek 121 ksllrdnvdl lgsladlyfr agdnknsvlk feqaqmldpy likgmdvygy llaregrled 181 venlgcrlfn isdqhaepwv vsgchsfysk rysralylga kaiqlnsnsv qalllkgaal 241 rnmgrvqeai ihfreairla pcrldcyegl iecylasnsi reamvmannv yktlganaqt 301 ltllatvcle dpvtqekakt lldkaltqrp dyikavvkka ellsreqkye dgiallrnal 361 anqsdcvlhr ilgdflvavn eyqeamdqys ialsldpndq kslegmqkme keesptdatq 421 eedvddmegs geegdlegsd seaaqwadqe qwfgmq
```

Human APC8/CDC23 is encoded by the following amino acid sequence (NCBI Accession No. AAF05755 and SEQ ID NO: 20):

```
  1 mvpvavtaav apvlsinsdf sdlreikkql lliagltrer gllhsskwsa elafslpalp 61 laelqppppi teedaqdmda ytlakayfdv keydraahfl hgcnskkayf lymysrylsg 121 ekkkddetvd slgplekgqv knealrelrv elskkhqare ldgfglylyg vvlrkldlvk 181 eaidvfveat hvlplhwgaw lelcnlitdk emlkflslpd twmkefflah iytelqliee 241 alqkyqnlid vgfskssyiv sqiavayhni rdidkalsif nelrkqdpyr ienmdtfsnl 301 lyvrsmksel sylahnlcei dkyrvetccv ignyyslrsq hekaalyfqr alklnprylg 361 awtlmgheym emkntsaaiq ayrhaievnk rdyrawyglg qtyeilkmpf yclyyyrrah 421 qlrpndsrml valgecyekl nqlveakkcy wrayavgdve kmalvklakl heqlteseqa 481 aqcyikyiqd iyscgeiveh leestafryl aqyyfkcklw deastcaqkc cafndtreeg 541 kallrqilql rnqgetptte vpapfflpas lsanntptrr vfpinlssvt p
```

Human APC8/CDC23 is encoded by the following amino acid sequence (NCBI Accession No. AAH10944 and SEQ ID NO: 21):

```
  1 mvpvavtaav apvlsinsdf sdlreikkql lliagltrer gllhsskwsa elafslpalp 61 laelqppppi teedaqdmda ytlakayfdv keydraahfl hgcnskkayf lymysrylvr 121 ailkchsafs etsifrtngk vksfk
```

Human APC8/CDC23 is encoded by the following amino acid sequence (NCBI Accession No. AAH05258 and SEQ ID NO: 22):

```
  1 mvpvavtaav apvlsinsdf sdlreikkql lliagltrer gllhsskwsa elafslpalp
 61 laelqppppi teedaqdmda ytlakayfdv keydraahfl hgcnskkayf lymysrylvr
121 ailkchsafs etsifrtngk vksfk
```

Human APC8/CDC23 is encoded by the following amino acid sequence (NCBI Accession No. AAH17713 and SEQ ID NO: 23):

```
  1 mvpvavtaav apvlsinsdf sdlreikkql lliagltrer gllhsskwsa elafslpalp
 61 laelqppppi teedaqdmda ytlakayfdv keydraahfl hgcnskkayf lymysrylsg
121 ekkkddetvd slgplekgqv knealrelrv elskkhqare ldgfglylyg vvlrkldlvk
181 eaidvfveat hvlplhwgaw lelcnlitdk emlkflslpd twmkefflah iytelqliee
241 alqkyqnlid vgfskssyiv sqiavayhni rdidkalsif nelrkqdpyr ienmdtfsnl
301 lyvrsmksel sylahnlcei dkyrvetccv ignyyslrsq hekaalyfqr alklnprylg
361 awtlmgheym emkntsaaiq ayrhaievnk rdyrawyglg qtyeilkmpf yclyyyrrah
421 qlrpndsrml valgecyekl nqlveakkcy wrayavgdve kmalvklakl heqlteseqa
481 aqcyikyiqd iyscgeiveh leestafryl aqyyfkcklw deastcaqkc cafndtreeg
541 kallrqilql rnqgetptte vpapfflpas lsanntptrr vspinlssvt p
```

Human APC8/CDC23 is encoded by the following amino acid sequence (NCBI Accession No. NP_004652 and SEQ ID NO: 24):

```
  1 maastsmvpv avtaavapvl sinsdfsdlr eikkqlllia gltrergllh sskwsaelaf
 61 slpalplael qppppiteed aqdmdaytla kayfdvkeyd raahflhgcn skkayflymy
121 srylsgekkk ddetvdslgp lekgqvknea lrelrvelsk khqareldgf glylygvvlr
181 kldlvkeaid vfveathvlp lhwgawlelc nlitdkemlk flslpdtwmk efflahiyte
241 lqlieealqk yqnlidvgfs kssyivsqia vayhnirdid kalsifnelr kqdpyrienm
301 dtfsnllyvr smkselsyla hnlceidkyr vetccvigny yslrsqheka alyfqralkl
361 nprylgawtl mgheymemkn tsaaiqayrh aievnkrdyr awyglgqtye ilkmpfycly
421 yyrrahqlrp ndsrmlvalg ecyeklnqlv eakkcywray avgdvekmal vklaklheql
481 teseqaaqcy ikyiqdiysc geivehlees tafrylaqyy fkcklwdeas tcaqkccafn
541 dtreegkall rqilqlrnqg etpttevpap fflpaslsan ntptrrvspl nlssvtp
```

Human APC8/CDC23 is encoded by the following amino acid sequence (NCBI Accession No. Q9UJX2 and SEQ ID NO: 25):

```
  1 mvpvavtaav apvlsinsdf sdlreikkql lliagltrer gllhsskwsa elafslpalp
 61 laelqppppi teedaqdmda ytlakayfdv keydraahfl hgcnskkayf lymysrylsg
121 ekkkddetvd slgplekgqv knealrelrv elskkhqare ldgfglylyg vvlrkldlvk
181 eaidvfveat hvlplhwgaw lelcnlitdk emlkflslpd twmkefflah iytelqliee
241 alqkyqnlid vgfskssyiv sqiavayhni rdidkalsif nelrkqdpyr ienmdtfsnl
301 lyvrsmksel sylahnlcei dkyrvetccv ignyyslrsq hekaalyfqr alklnprylg
```

```
361 awtlmgheym emkntsaaiq ayrhaievnk rdyrawyglg qtyeilkmpf yclyyyrrah 421 qlrpndsrml valgecyekl nqlveakkcy wrayavgdve kmalvklakl heqlteseqa 481 aqcyikyiqd iyscgeiveh leestafryl aqyyfkcklw deastcaqkc cafndtreeg 541 kallrqilql rnqgetptte vpapfflpas lsanntptrr vspinlssvt p
```

EXAMPLES

Example 1

TAME Inhibits APC Activation

Figure 2:
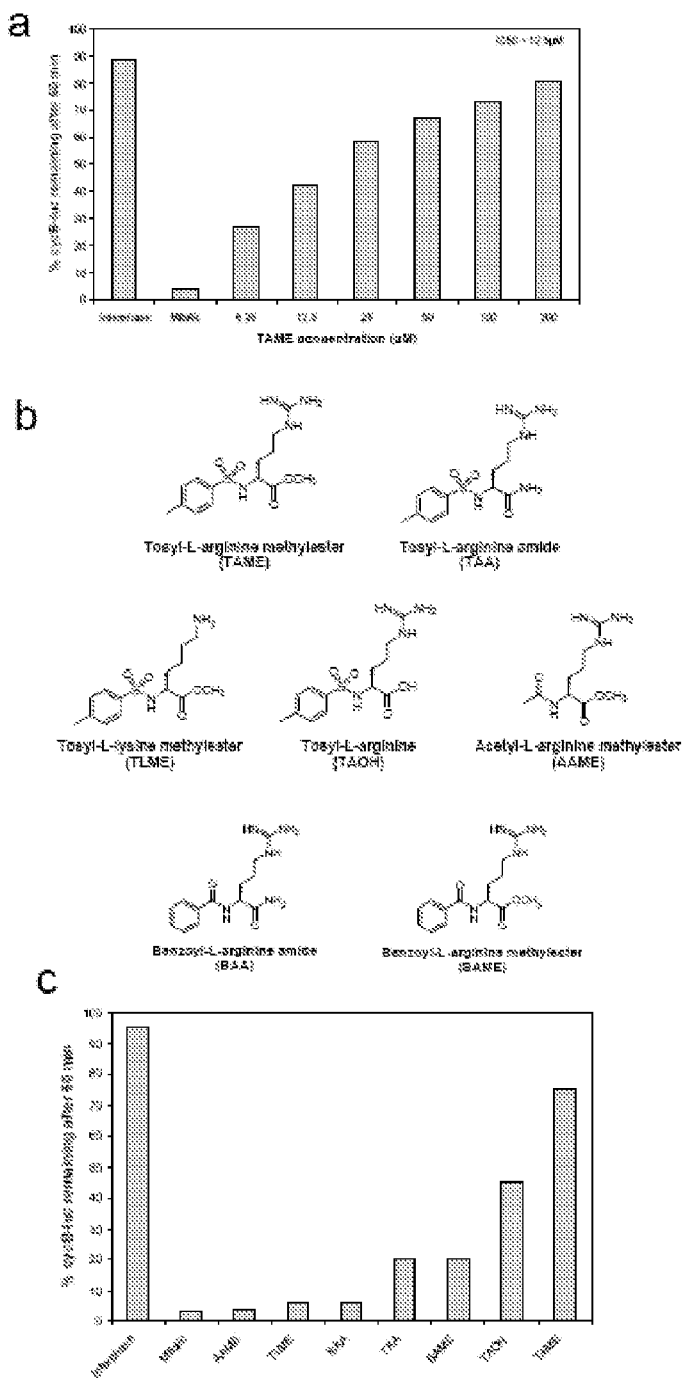
FIG. 2A is a graph of the results of a luciferase assay showing the dose-dependent inhibition of cyclin B-luciferase degradation in mitotic extract by TAME. Different concentrations of TAME were added to mitotic *Xenopus* extract containing a cyclin B-luciferase reporter. Samples were collected at 60 minutes and the remaining reporter level was measured by luminescence. Interphase extract was used as a negative control.
FIG. 2B is a series of schematic diagrams representing the structures of TAME derivatives.
FIG. 2C is a graph showing the results of a luciferase assay in which the derivatives shown in FIG. 2B were tested at 200 μM

A library of 110,000 compounds was screened for inhibitors of APC-dependent proteolysis in mitotic *Xenopus* egg extract, as previously reported (Verna, R. et al. 2004. Science 306(5693):117). Tosyl-L-Arginine Methyl Ester (TAME; FIG. 1A) was identified as one of the most potent hits, with an IC50 of approximately 12 µM (FIG. 2A). TAME also inhibited cyclin-luciferase proteolysis stimulated by addition of Cdh1 to interphase extract, but did not inhibit β-catenin-luciferase proteolysis stimulated by addition of axin (Verna, R. et al. 2004. Science 306(5693):117), indicating that TAME is not a general inhibitor of the ubiquitin-proteasome system. A series of TAME derivatives were tested to establish a structure-activity relationship (FIG. 2B, C). Acetyl-L-Arginine Methyl Ester (AAME; FIG. 1A) emerged as the derivative with the lowest activity, and this compound was used as a negative control in subsequent experiments.

It was next determined whether TAME is sufficient to induce mitotic arrest in *Xenopus* extract. Purified cyclin B1/cdc2 complex (MPF) was added to interphase extract in the presence of DMSO, AAME, or TAME. All extracts entered mitosis within 15 min of MPF addition, as indicated by decreased mobility of the APC subunit Cdc27, a consequence of Cdc27 phosphorylation (FIG. 1B). In the presence of DMSO or AAME, cyclin B1 was degraded by 30 min, resulting in MPF inactivation and dephosphorylation of Cdc27. In the presence of 200 µM TAME, however, cyclin B1 and Cdc27 phosphorylation remained stable, indicating that TAME is capable of inducing mitotic arrest in *Xenopus* extract. Another APC substrate, cyclin A, was also stabilized by TAME in *Xenopus* extract.

Figure 3:
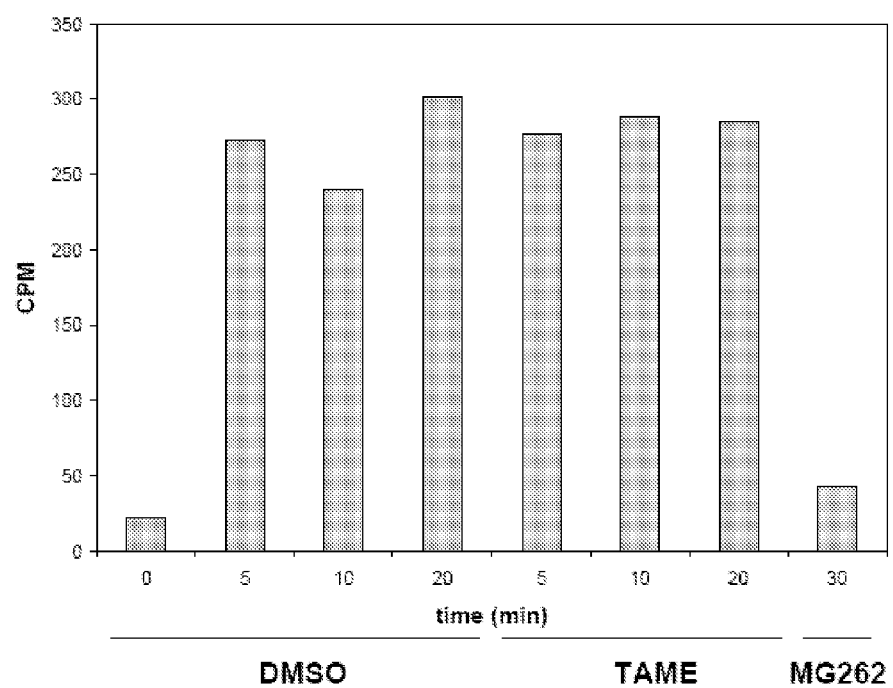
FIG. 3 is a graph showing the counts per minute (cpm) of all protein precipitated from *Xenopus* extract supplemented with DMSO or 200 μM TAME and baculovirus-expressed and purified $^{35}$S-labeled Cyclin B, which was first ubiquitinated by APC in an in vitro ubiquitination system. At indicated time points, all protein was precipitated and the level of radioactivity in supernatant was measured by scintillation counting. MG262 was used as a positive control.

To identify the molecular target of TAME, it was determined whether TAME interferes with ubiquitination of cyclin B1, or with the subsequent step of targeting ubiquitinated cyclin B1 to the proteasome. A purified MPF complex containing 35S-labeled cyclin B1 was ubiquitinated by APC in a reconstituted ubiquitination system, and then added to interphase *Xenopus* extract in the presence or absence of inhibitors. Degradation of pre-ubiquitinated cyclin B1 was equally efficient in the presence of DMSO or TAME, but was strongly inhibited by the proteasome inhibitor MG262 (FIG. 3), indicating that TAME does not inhibit proteasomal degradation of ubiquitinated cyclin B1.

Figure 4:
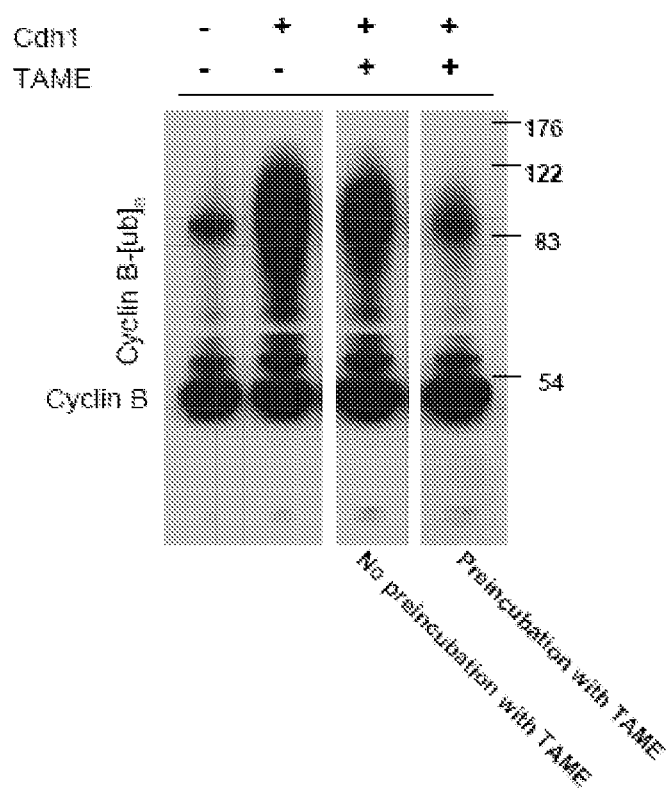
FIG. 4 is a ubiquitization assay in which recombinant Cdh1 was added into interphase extract with or without preincubation with 200 μM TAME for 1.5 h followed by APC immunoprecipitation.

To test if TAME inhibits APC activity, APC was immunopurified from mitotic *Xenopus* extract and added the compound directly to a reconstituted ubiquitination assay. Surprisingly, TAME showed no activity in this assay (FIG. 1C), indicating that it is not an inhibitor of the ligase activity per se. However, if TAME was added to mitotic *Xenopus* extract during immunoprecipitation, the isolated APC showed a dramatic loss of activity (FIG. 1C), suggesting that TAME acts as an inhibitor of APC activation. Because TAME is capable of stabilizing cyclin B1 in interphase extracts treated with Cdh1, it was also determined whether TAME could inhibit interphase APC activated by Cdh1. Again, TAME did not inhibit APC-Cdh1 when added directly to a reconstituted assay; however, if TAME was added to interphase extract 30 minutes prior to the addition of Cdh1, considerable reduction in the level of cyclin B1 ubiquitination was observed (FIG. 1D). Interestingly, if TAME and Cdh1 were added simultaneously, TAME was less effective in blocking APC activation (FIG. 4). Together these findings indicate that TAME is capable of inhibiting activation of the APC mediated by either Cdc20 or Cdh1.

Example 2

TAME Inhibits Activator Protein Binding to the APC

Figure 5:
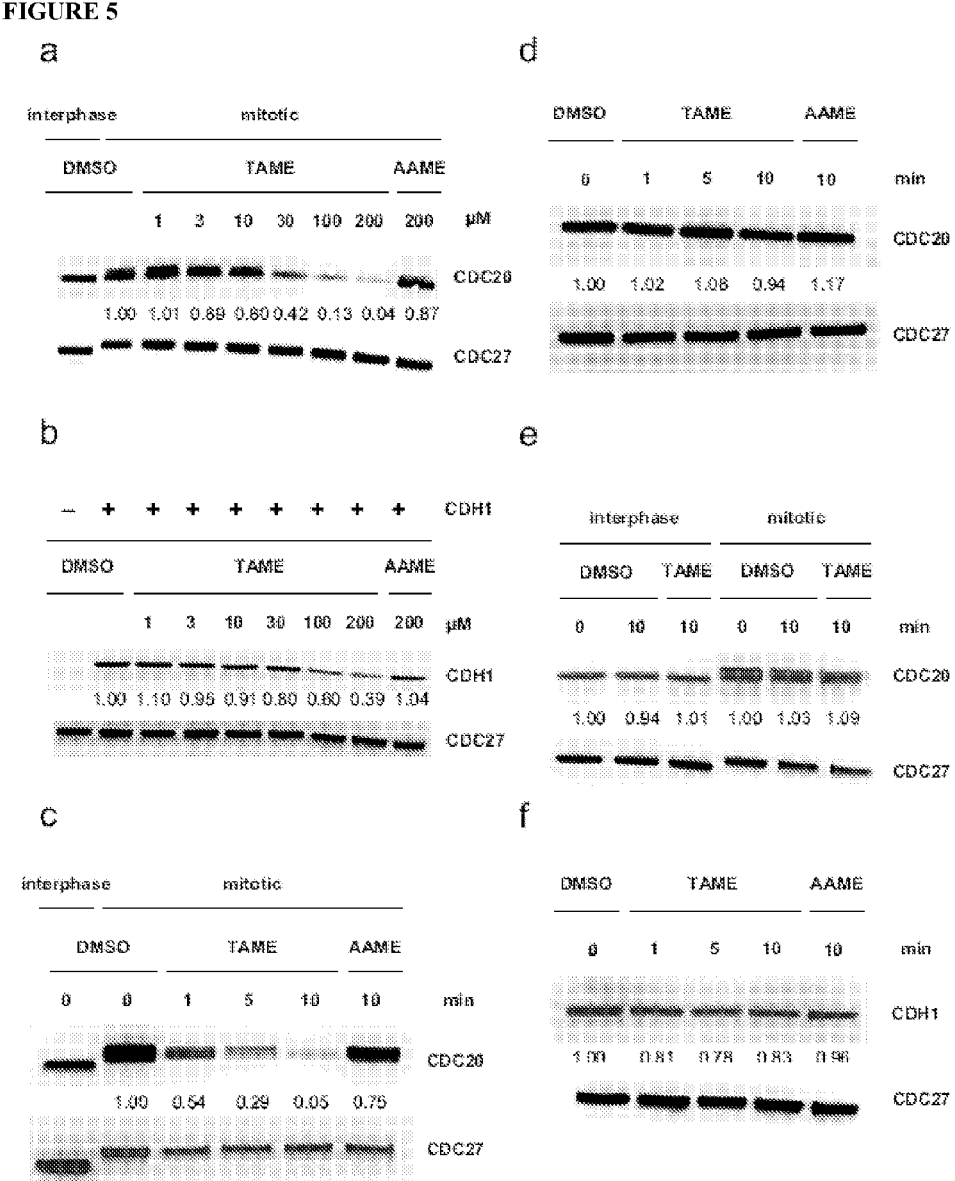
FIG. 5A TAME inhibits Cdc20 association with mitotic APC in a dose-dependent manner. APC was immunoprecipitated from mitotic extract supplemented with different concentrations of TAME as indicated and the amount of Cdc27 and Cdc20 was analyzed by Western blot. Numbers indicate the relative amount of Cdc20 normalized to that of Cdc27.
FIG. 5B TAME inhibits Cdh1 association with interphase APC in a dose-dependent manner. Interphase extract was pre-incubated with different concentrations of TAME as indicated for 30 min before addition of recombinant Cdh1. APC was then immunoprecipitated and the amount of Cdc27 and Cdh1 was analyzed by Western blot. Numbers indicate the relative amount of Cdh1 normalized to that of Cdc27.
FIG. 5C Cdc20 binding to mitotic APC is highly dynamic. APC-Cdc20 was first immunoprecipitated from mitotic extract and then resuspended in extract containing 200 μM TAME or AAME. Beads were re-isolated, washed and blotted for Cdc27 and Cdc20.
FIG. 5D Cdc20 binding to interphase APC is not dynamic. APC-Cdc20 was first immunoprecipitated from interphase extract and then resuspended in extract containing 200 μM TAME or AAME. Beads were re-isolated, washed and blotted for Cdc27 and Cdc20.
FIG. 5E APC-Cdc20 is a stable complex in XB buffer. APC-Cdc20 was first immunoprecipitated from interphase or mitotic extract and then resuspended in XB containing 200 μM TAME or AAME or 1% DMSO. Beads were re-isolated, washed and blotted for Cdc27 and Cdc20.
FIG. 5F Cdh1 binding to interphase APC is not dynamic. Recombinant Cdh1 was added into interphase extract. APC-Cdh1 was then immunoprecipitated and resuspended in extract containing 200 μM TAME or AAME. Beads were re-isolated, washed and blotted for Cdc27 and Cdh1.

Because TAME inhibits APC activation, it was next determined whether TAME acts by interfering with activator protein association. APC was immunoprecipitated from mitotic *Xenopus* extract containing different concentrations of TAME and observed a dose-dependent reduction in the amount of Cdc20 associated with the APC (FIG. 5A). Similarly, TAME inhibited Cdh1 binding to the APC, although the reduction was not as dramatic (FIG. 5B).

Current models of APC regulation suggest that Cdc20 associates with the APC weakly during interphase and becomes more strongly associated with the APC as the complex becomes phosphorylated during mitosis (Kraft, C. et al. 2003. EMBO J. 22(24):6598; Kramer, E. R. et al. 2000. Mol Biol Cell. 11(5): 1555). However, TAME is an effective inhibitor of cyclin proteolysis and Cdc20 association even when added to mitotic extracts in which Cdc20 is presumably stably bound to the APC. To understand the basis of this discrepancy, the dynamics of Cdc20 association with the APC were measured in interphase and mitotic extracts, using TAME as a tool to block reassociation of Cdc20 with the APC. APC was immunoprecipitated from mitotic extract and then resuspended the complex in mitotic extract containing TAME. It was found that Cdc20 dissociated from the APC very rapidly in mitotic extract, with a half-life of approximately 1 min (FIG. 5C). In contrast, although Cdc20 was capable of binding interphase Cdc20, its association was not dynamic (FIG. 5D). Dissociation of Cdc20 from mitotic APC appears to require an activity in the extract, as Cdc20 binding to mitotic APC remained stable in buffer (FIG. 5E). Finally, it was found that Cdh1 binding to interphase APC is also not dynamic (FIG. 5F), explaining why pre-incubation enhances the ability of TAME to block Cdh1 binding to the APC. In contrast, the high rate of Cdc20 dissociation from the APC during mitosis appears to render the system highly sensitive to the inhibitory effects of TAME, regardless of the timing of compound addition.

Example 3

TAME Binds to the APC and Blocks IR-tail Interactions

Figure 6:
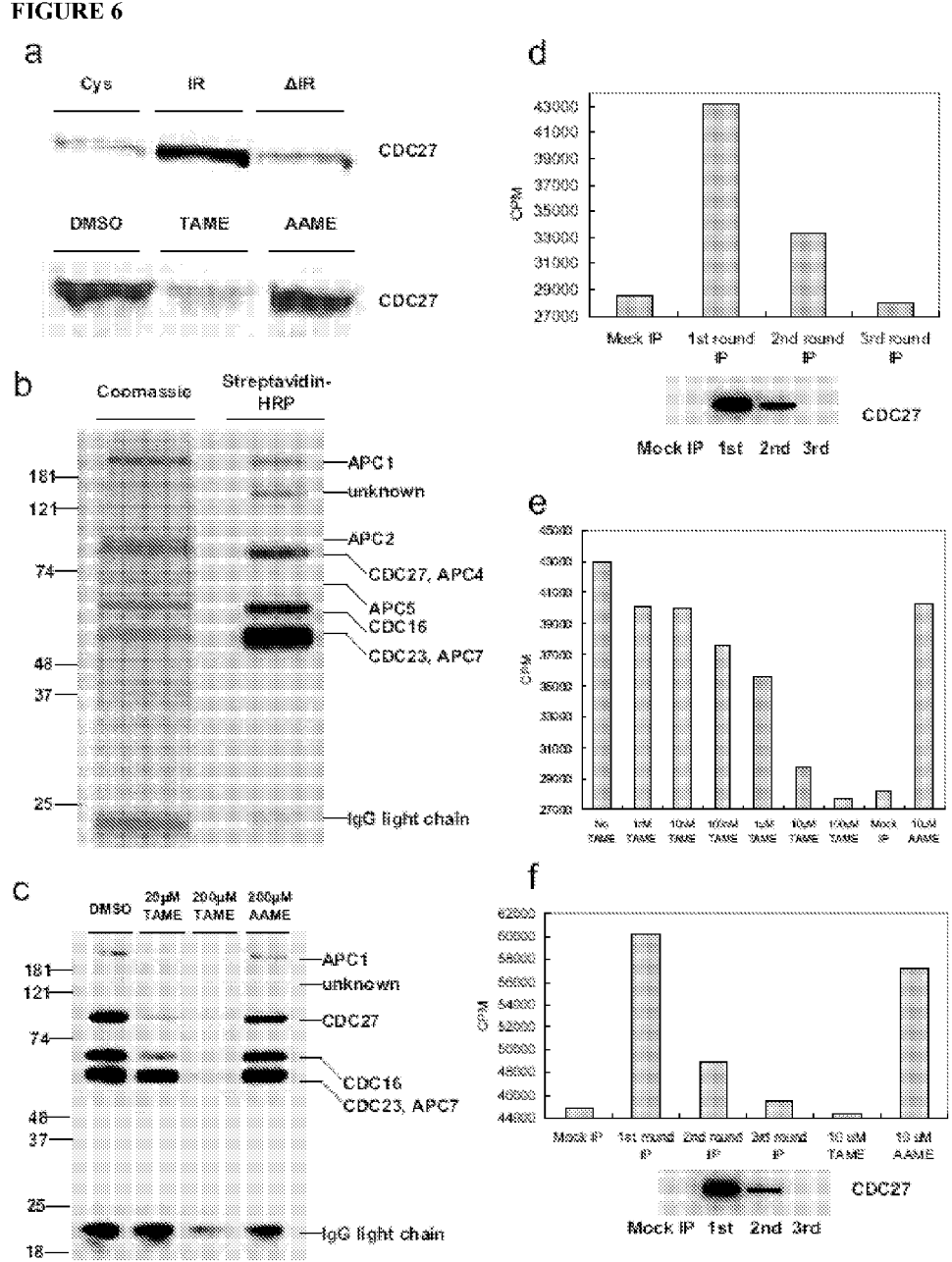
FIG. 6A TAME inhibits the interaction between APC and an IR peptide resin. Top panel: Iodoacetyl resin was coupled with cysteine, a 21aa C-terminal peptide of Cdh1 or a 19aa peptide missing the C-terminal IR tail. The resin was incubated with interphase extract and the amount of Cdc27 bound on resin was analyzed. Bottom panel: Iodoacetyl resin coupled with the 21aa IR peptide was incubated with interphase extract supplemented with DMSO, 200 μM TAME or AAME and the amount of Cdc27 bound on resin was analyzed.
FIG. 6B IR peptide labeled with a photoactive crosslinker crosslinks to a specific subset of APC subunits. Left: Coomassie stain of APC immunopurified from interphase extract with Cdc27 antibody. Right: APC subunits that got crosslinked by the labeled IR peptide visualized by streptavidin-HRP blot.
FIG. 6C TAME inhibits IR peptide crosslinking to APC subunits. Crosslinking was performed in the presence of different concentrations of TAME or AAME as indicated.
FIG. 6D $^3$H TAME directly binds to *Xenopus* APC. Interphase extract was subjected to three rounds of immunoprecipitation with Cdc27 antibody. The amount of Cdc27 pulled down at each round was shown by Western blot. 200 nM of $^3$H TAME was added into extract that had undergone zero, one or two rounds of immunoprecipitation before another round of Cdc27 immunoprecipitation. The specific counts associated with the beads were determined by scintillation counting.
FIG. 6E Unlabeled TAME but not AAME can compete with $^3$H TAME for binding to *Xenopus* APC. 200 nM $^3$H TAME was added into interphase extract with different concentrations of unlabeled TAME or AAME as indicated before Cdc27 immunoprecipitation. The specific counts associated with the beads were determined by scintillation counting.
FIG. 6F $^3$H TAME directly binds to human APC. The same experiment was done as described in 3C using asynchronous Hela cell lysate.

Because TAME has a striking structural resemblance to Cdc20 and Cdh1's IR tail, TAME may inhibit the binding of activator proteins to the APC by competing with the binding of the IR tail. To demonstrate this mechanism, a 21 amino acid C-terminal peptide of Cdh1 was synthesized, which was previously used to recruit APC from HeLa cell lysate in an IR-dependent manner (Vodermaier, H. C. et al. 2003. Curr Biol. 13(17):1459). It was found that this peptide could also recruit APC from interphase *Xenopus* extract in an IR-dependent manner (FIG. 6A). It was found that TAME could efficiently inhibit APC recruitment, whereas DMSO or AAME had no effect (FIG. 6A), suggesting that TAME can inhibit interactions between an IR tail-containing peptide and the APC.

Figure 7:
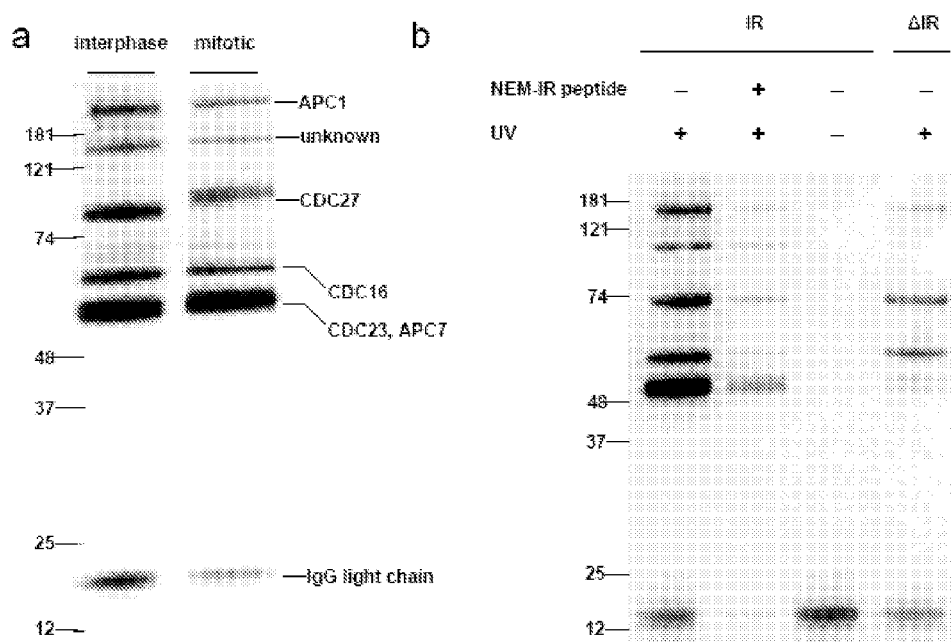
FIG. 7A Cdc27 but not Apc4 is crosslinked by labeled IR peptide labeled with a photoactive crosslinker. Crosslinking assay was performed with interphase and mitotic APC and crosslinked subunits were visualized by streptavidin-HRP blot. The shifted band represents mitotic phosphorylation of Cdc27.
FIG. 7B Crosslinking is IR tail specific. Crosslinking assay was performed in the presence of excess unlabeled IR peptide (lane 2), no UV illumination (lane 3) or with labeled ΔIR peptide.

To identify APC subunits that interact with TAME and the IR peptide, the IR peptide was conjugated to a photo-affinity reagent that covalently transfers biotin to proteins in the proximity of the labeled peptide. APC was immunoprecipitated from interphase *Xenopus* extract, incubated with the labeled peptide, and then induced to crosslink by UV illumination. Crosslinked proteins containing biotin were visualized by streptavidin-HRP blot. To identify specific subunits, the blot was aligned with a coomassie stain of purified APC, in which individual subunits were identified by mass spectrometry. It was found that while Apc1 was weakly labeled, proteins in the TPR subcomplex, namely Cdc27, Cdc16, Cdc23 and Apc7, were strongly crosslinked (FIG. 6B). This result is consistent with previous reports that the TPR subunits mediate Cdh1 binding to the APC (Vodermaier, H. C. et al. 2003. Curr Biol. 13(17):1459; Thornton, B. R. et al. 2006. Genes Dev. 20(4):449). Simliar studies were performed with mitotic APC, in which the mobility of Cdc27 is shifted due to phosphorylation 17 and confirmed that the peptide crosslinked to Cdc27 but not Apc4 (FIG. 7A). Crosslinking to the TPR subunits was strictly UV dependent and could be competed by excess unlabeled IR peptide (FIG. 7B). Furthermore, a labeled ΔIR peptide showed dramatically reduced crosslinking to APC subunits, indicating that crosslinking is IR-specific (FIG. 7B). The ability of TAME to block crosslinking of the IR-containing peptide to the APC was next determined. It was found that 20 μM TAME efficiently inhibited Cdc27 and Cdc16 labeling, but only slightly reduced Cdc23 and Apc7 labeling (FIG. 6C). At 200 μM, TAME strongly inhibited crosslinking to all APC subunits. The differential sensitivity to TAME suggests that different TPR subunits may have distinct affinities for the IR tail or for TAME. However, it is worth noting that the biotin label can be transferred to any subunit within close proximity of the peptide binding site, not necessarily only the subunit to which the IR tail is bound. For example, we observed some biotin transfer to the IgG light chain of the Cdc27 antibody, which could be inhibited by a high concentration of TAME. Nevertheless, the data strongly suggest that TAME antagonizes crosslinking by competing for binding to IR tail binding sites present in the TPR subcomplex of the APC.

Figure 8:
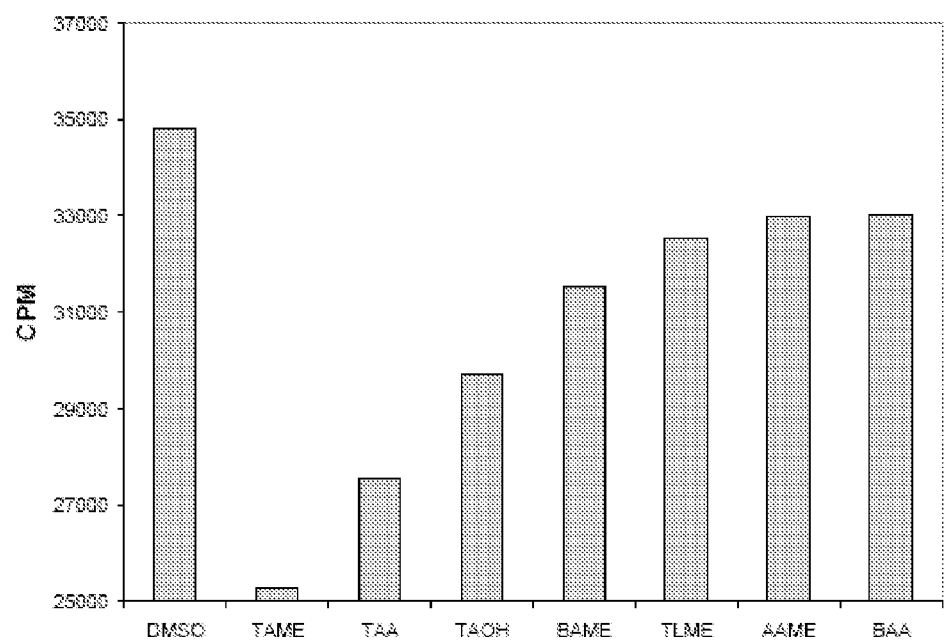
FIG. 8 The ability of unlabeled TAME derivates to compete with $^3$H TAME for binding to APC agrees with the structure-activity relationship. 200 nM $^3$H TAME was added into interphase extract with 10 μM of unlabeled TAME derivatives as indicated before Cdc27 immunoprecipitation. The specific counts associated with the beads were determined by scintillation counting. Their relative ability to compete largely agrees with their relative activity in the luciferase assay as shown in FIG. 2C.

To directly determine whether TAME binds to the APC, 3H-TAME was added to interphase *Xenopus* extract, or to extract that had been partially or completely immunodepleted of the APC. The remaining APC was immunoprecipitated with Cdc27 antibody and the amount of bound TAME was measured by scintillation counting. In parallel, the amount of immunoprecipitated Cdc27 was determined by immunoblot. It was found that specific binding of 3H-TAME correlated with the amount of Cdc27 isolated from the extract (FIG. 6D). Moreover, unlabeled TAME competitively inhibited specific binding of 3H-TAME, whereas AAME did not (FIG. 6E). The ability of other TAME derivatives to compete with 3H-TAME for APC binding correlated with their ability to inhibit degradation of cyclin B-luciferase in *Xenopus* extract (FIG. 8). Together these experiments indicate that TAME is capable of binding directly to *Xenopus* APC.

It was next determined that TAME also binds to human APC. 3H-TAME was added to lysates from asynchronous HeLa cells partially or completely immunodepleted of APC, and again found that the specific binding of 3H-TAME correlated with the amount of APC that was isolated (FIG. 6F). Moreover, cold TAME competed efficiently with specific 3H-TAME binding but AAME did not (FIG. 6F).

Taken together, these results indicate that TAME is capable of binding to both *Xenopus* and human APC, where it antagonizes IR tail interactions to inhibit Cdc20 or Cdh1 binding to the APC.

Other Embodiments

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for inhibiting a ubiquitination activity of an APC in a mammalian cell comprising a spindle assembly checkpoint (SAC), comprising administering an effective amount of a non-peptide analog of a C-terminal IR motif of an activator of an APC to a mammalian cell to inhibit a degradation of a substrate of an APC.

2. A method for inhibiting a ubiquitination activity of an APC in a mammalian cell comprising a spindle assembly checkpoint (SAC), comprising administering an effective amount of a non-peptide analog of a C-terminal IR motif of an activator of an APC to a mammalian cell to induce a cell cycle checkpoint.

3. The method of claim 1 or 2, wherein said analog is tosyl-L-arginine methylester (TAME).

4. The method of claim 1 or 2, wherein said analog is tosyl-L-arginine methylester (TAME), tosyl-L-arginine amide (TAA), tosyl-L-lysine methylester (TLME), tosyl-L-arginine (TAOH), acetyl-L-arginine methylester (AAME), Benzoyl-L-arginine amide (BAA), tosyl-L-arginine t-butyl-ester (TATE), or Benzoyl-L-arginine methylester (BAME).

5. The method of claim 1, wherein said cell is human.

6. The method of claim 1, wherein said analog contacts a component of a tetratricopeptide repeats (TPR) subcomplex of an APC.

7. The method of claim 6, wherein said component of a TPR subcomplex is APC3/Cdc27, APC6, APC7, or APC8.

8. The method of claim 2, wherein said cell cycle checkpoint is a spindle assembly checkpoint (SAC).

9. The method of claim 1 or 2, wherein said activator of an APC is Cdc20 or Cdh1.

* * * * *

SEQUENCE LISTING

<160> NUMBER OF SEQ ID NOS: 26

<210> SEQ ID NO 1
<211> LENGTH: 830
<212> TYPE: PRT
<213> ORGANISM: Homo sapiens

<400> SEQUENCE: 1

Met Thr Val Leu Gln Glu Pro Val Gln Ala Ala Ile Trp Gln Ala Leu
1               5                   10                  15

Asn His Tyr Ala Tyr Arg Asp Ala Val Phe Leu Ala Glu Arg Leu Tyr
            20                  25                  30

Ala Glu Val His Ser Glu Glu Ala Leu Phe Leu Leu Ala Thr Cys Tyr
        35                  40                  45

Tyr Arg Ser Gly Lys Ala Tyr Lys Ala Tyr Arg Leu Leu Lys Gly His
    50                  55                  60

Ser Cys Thr Thr Pro Gln Cys Leu Tyr Leu Leu Ala Lys Cys Cys Val
65                  70                  75                  80

Asp Leu Ser Lys Leu Ala Glu Gly Gln Ile Leu Ser Gly Gly Val
            85                  90                  95

Phe Asn Lys Gln Lys Ser His Asp Asp Ile Val Thr Glu Phe Gly Asp
            100                 105                 110

Ser Ala Cys Phe Thr Leu Ser Leu Leu Gly His Val Tyr Cys Lys Thr
        115                 120                 125

Asp Arg Leu Ala Lys Gly Ser Glu Cys Tyr Gln Lys Ser Leu Ser Leu
    130                 135                 140

Asn Pro Phe Leu Trp Ser Pro Phe Glu Ser Leu Cys Glu Ile Gly Glu
145                 150                 155                 160

Lys Pro Asp Pro Asp Gln Thr Phe Lys Phe Thr Ser Leu Gln Asn Phe
            165                 170                 175

Ser Asn Cys Leu Pro Asn Ser Cys Thr Thr Gln Val Pro Asn His Ser
        180                 185                 190

Leu Ser His Arg Gln Pro Glu Thr Val Leu Thr Glu Thr Pro Gln Asp
    195                 200                 205

Thr Ile Glu Leu Asn Arg Leu Asn Leu Glu Ser Ser Asn Ser Lys Tyr
210                 215                 220

Ser Leu Asn Thr Asp Ser Ser Val Ser Tyr Ile Asp Ser Ala Val Ile
225                 230                 235                 240

Ser Pro Asp Thr Val Pro Leu Gly Thr Gly Thr Ser Ile Leu Ser Lys
            245                 250                 255

Gln Val Gln Asn Lys Pro Lys Thr Gly Arg Ser Leu Leu Gly Gly Pro
        260                 265                 270

Ala Ala Leu Ser Pro Leu Thr Pro Ser Phe Gly Ile Leu Pro Leu Glu
    275                 280                 285

Thr Pro Ser Pro Gly Asp Gly Ser Tyr Leu Gln Asn Tyr Thr Asn Thr
290                 295                 300

Pro Pro Val Ile Asp Val Pro Ser Thr Gly Ala Pro Ser Lys Lys Thr
305                 310                 315                 320

Phe Arg Val Leu Gln Ser Val Ala Arg Ile Gly Gln Thr Gly Thr Lys
            325                 330                 335

Ser Val Phe Ser Gln Ser Gly Asn Ser Arg Glu Val Thr Pro Ile Leu
        340                 345                 350

Ala Gln Thr Gln Ser Ser Gly Pro Gln Thr Ser Thr Pro Gln Val
    355                 360                 365

```
Leu Ser Pro Thr Ile Thr Ser Pro Pro Asn Ala Leu Pro Arg Arg Ser
370                 375                 380

Ser Arg Leu Phe Thr Ser Asp Ser Ser Thr Thr Lys Glu Asn Ser Lys
385                 390                 395                 400

Lys Leu Lys Met Lys Phe Pro Pro Lys Ile Pro Asn Arg Lys Thr Lys
                405                 410                 415

Ser Lys Thr Asn Lys Gly Gly Ile Thr Gln Pro Asn Ile Asn Asp Ser
                420                 425                 430

Leu Glu Ile Thr Lys Leu Asp Ser Ile Ile Ser Glu Gly Lys Ile
            435                 440                 445

Ser Thr Ile Thr Pro Gln Ile Gln Ala Phe Asn Leu Gln Lys Ala Ala
450                 455                 460

Ala Glu Gly Leu Met Ser Leu Leu Arg Glu Met Gly Lys Gly Tyr Leu
465                 470                 475                 480

Ala Leu Cys Ser Tyr Asn Cys Lys Glu Ala Ile Asn Ile Leu Ser His
                485                 490                 495

Leu Pro Ser His His Tyr Asn Thr Gly Trp Val Leu Cys Gln Ile Gly
                500                 505                 510

Arg Ala Tyr Phe Glu Leu Ser Glu Tyr Met Gln Ala Glu Arg Ile Phe
                515                 520                 525

Ser Glu Val Arg Arg Ile Glu Asn Tyr Arg Val Glu Gly Met Glu Ile
530                 535                 540

Tyr Ser Thr Thr Leu Trp His Leu Gln Lys Asp Val Ala Leu Ser Val
545                 550                 555                 560

Leu Ser Lys Asp Leu Thr Asp Met Asp Lys Asn Ser Pro Glu Ala Trp
                565                 570                 575

Cys Ala Ala Gly Asn Cys Phe Ser Leu Gln Arg Glu His Asp Ile Ala
                580                 585                 590

Ile Lys Phe Phe Gln Arg Ala Ile Gln Val Asp Pro Asn Tyr Ala Tyr
                595                 600                 605

Ala Tyr Thr Leu Leu Gly His Glu Phe Val Leu Thr Glu Glu Leu Asp
                610                 615                 620

Lys Ala Leu Ala Cys Phe Arg Asn Ala Ile Arg Val Asn Pro Arg His
625                 630                 635                 640

Tyr Asn Ala Trp Tyr Gly Leu Gly Met Ile Tyr Tyr Lys Gln Glu Lys
                645                 650                 655

Phe Ser Leu Ala Glu Met His Phe Gln Lys Ala Leu Asp Ile Asn Pro
                660                 665                 670

Gln Ser Ser Val Leu Leu Cys His Ile Gly Val Val Gln His Ala Leu
                675                 680                 685

Lys Lys Ser Glu Lys Ala Leu Asp Thr Leu Asn Lys Ala Ile Val Ile
690                 695                 700

Asp Pro Lys Asn Pro Leu Cys Lys Phe His Arg Ala Ser Val Leu Phe
705                 710                 715                 720

Ala Asn Glu Lys Tyr Lys Ser Ala Leu Gln Glu Leu Glu Glu Leu Lys
                725                 730                 735

Gln Ile Val Pro Lys Glu Ser Leu Val Tyr Phe Leu Ile Gly Lys Val
                740                 745                 750

Tyr Lys Lys Leu Gly Gln Thr His Leu Ala Leu Met Asn Phe Ser Trp
                755                 760                 765

Ala Met Asp Leu Asp Pro Lys Gly Ala Asn Asn Gln Ile Lys Glu Ala
                770                 775                 780

Ile Asp Lys Arg Tyr Leu Pro Asp Asp Glu Glu Pro Ile Thr Gln Glu
```

```
                785                 790                 795                 800
Glu Gln Ile Met Gly Thr Asp Glu Ser Gln Glu Ser Ser Met Thr Asp
                    805                 810                 815

Ala Asp Asp Thr Gln Leu His Ala Ala Glu Ser Asp Glu Phe
                    820                 825                 830

<210> SEQ ID NO 2
<211> LENGTH: 824
<212> TYPE: PRT
<213> ORGANISM: Homo sapiens

<400> SEQUENCE: 2

Met Thr Val Leu Gln Glu Pro Val Gln Ala Ala Ile Trp Gln Ala Leu
1               5                   10                  15

Asn His Tyr Ala Tyr Arg Asp Ala Val Phe Leu Ala Glu Arg Leu Tyr
            20                  25                  30

Ala Glu Val His Ser Glu Glu Ala Leu Phe Leu Leu Ala Thr Cys Tyr
        35                  40                  45

Tyr Arg Ser Gly Lys Ala Tyr Lys Ala Tyr Arg Leu Leu Lys Gly His
    50                  55                  60

Ser Cys Thr Thr Pro Gln Cys Lys Tyr Leu Leu Ala Lys Cys Cys Val
65                  70                  75                  80

Asp Leu Ser Lys Leu Ala Glu Gly Gln Ile Leu Ser Gly Val
                85                  90                  95

Phe Asn Lys Gln Lys Ser His Asp Asp Ile Val Thr Glu Phe Gly Asp
                100                 105                 110

Ser Ala Cys Phe Thr Leu Ser Leu Leu Gly His Val Tyr Cys Lys Thr
            115                 120                 125

Asp Arg Leu Ala Lys Gly Ser Glu Cys Tyr Gln Lys Ser Leu Ser Leu
        130                 135                 140

Asn Pro Phe Leu Trp Ser Pro Phe Glu Ser Leu Cys Glu Ile Gly Glu
145                 150                 155                 160

Lys Pro Asp Pro Asp Gln Thr Phe Lys Phe Thr Ser Leu Gln Asn Phe
                165                 170                 175

Ser Asn Cys Leu Pro Asn Ser Cys Thr Thr Gln Val Pro Asn His Ser
            180                 185                 190

Leu Ser His Arg Gln Pro Glu Thr Val Leu Thr Glu Thr Pro Gln Asp
        195                 200                 205

Thr Ile Glu Leu Asn Arg Leu Asn Leu Glu Ser Ser Asn Ser Lys Tyr
    210                 215                 220

Ser Leu Asn Thr Asp Ser Ser Val Ser Tyr Ile Asp Ser Ala Val Ile
225                 230                 235                 240

Ser Pro Asp Thr Val Pro Leu Gly Thr Gly Thr Ser Ile Leu Ser Lys
                245                 250                 255

Gln Val Gln Asn Lys Pro Lys Thr Gly Arg Ser Leu Leu Gly Gly Pro
            260                 265                 270

Ala Ala Leu Ser Pro Leu Thr Pro Ser Phe Gly Ile Leu Pro Leu Glu
        275                 280                 285

Thr Pro Ser Pro Gly Asp Gly Ser Tyr Leu Gln Asn Tyr Thr Asn Thr
    290                 295                 300

Pro Pro Val Ile Asp Val Pro Ser Thr Gly Ala Pro Ser Lys Lys Ser
305                 310                 315                 320

Val Ala Arg Ile Gly Gln Thr Gly Thr Lys Ser Val Phe Ser Gln Ser
                325                 330                 335
```

```
Gly Asn Ser Arg Glu Val Thr Pro Ile Leu Ala Gln Thr Gln Ser Ser
                340                 345                 350

Gly Pro Gln Thr Ser Thr Thr Pro Gln Val Leu Ser Pro Thr Ile Thr
            355                 360                 365

Ser Pro Pro Asn Ala Leu Pro Arg Arg Ser Ser Arg Leu Phe Thr Ser
        370                 375                 380

Asp Ser Ser Thr Thr Lys Glu Asn Ser Lys Lys Leu Lys Met Lys Phe
385                 390                 395                 400

Pro Pro Lys Ile Pro Asn Arg Lys Thr Lys Ser Lys Thr Asn Lys Gly
                405                 410                 415

Gly Ile Thr Gln Pro Asn Ile Asn Asp Ser Leu Glu Ile Thr Lys Leu
            420                 425                 430

Asp Ser Ser Ile Ile Ser Glu Gly Lys Ile Ser Thr Ile Thr Pro Gln
        435                 440                 445

Ile Gln Ala Phe Asn Leu Gln Lys Ala Ala Glu Gly Leu Met Ser
450                 455                 460

Leu Leu Arg Glu Met Gly Lys Gly Tyr Leu Ala Leu Cys Ser Tyr Asn
465                 470                 475                 480

Cys Lys Glu Ala Ile Asn Ile Leu Ser His Leu Pro Ser His His Tyr
                485                 490                 495

Asn Thr Gly Trp Val Leu Cys Gln Ile Gly Arg Ala Tyr Phe Glu Leu
            500                 505                 510

Ser Glu Tyr Met Gln Ala Glu Arg Ile Phe Ser Glu Val Arg Arg Ile
        515                 520                 525

Glu Asn Tyr Arg Val Gly Met Glu Ile Tyr Ser Thr Thr Leu Trp
530                 535                 540

His Leu Gln Lys Asp Val Ala Leu Ser Val Leu Ser Lys Asp Leu Thr
545                 550                 555                 560

Asp Met Asp Lys Asn Ser Pro Glu Ala Trp Cys Ala Ala Gly Asn Cys
                565                 570                 575

Phe Ser Leu Gln Arg Glu His Asp Ile Ala Ile Lys Phe Phe Gln Arg
            580                 585                 590

Ala Ile Gln Val Asp Pro Asn Tyr Ala Tyr Ala Tyr Thr Leu Leu Gly
        595                 600                 605

His Glu Phe Val Leu Thr Glu Glu Leu Asp Lys Ala Leu Ala Cys Phe
610                 615                 620

Arg Asn Ala Ile Arg Val Asn Pro Arg His Tyr Asn Ala Trp Tyr Gly
625                 630                 635                 640

Leu Gly Met Ile Tyr Tyr Lys Gln Glu Lys Phe Ser Leu Ala Glu Met
                645                 650                 655

His Phe Gln Lys Ala Leu Asp Ile Asn Pro Gln Ser Ser Val Leu Leu
            660                 665                 670

Cys His Ile Gly Val Val Gln His Ala Leu Lys Lys Ser Glu Lys Ala
        675                 680                 685

Leu Asp Thr Leu Asn Lys Ala Ile Val Ile Asp Pro Lys Asn Pro Leu
690                 695                 700

Cys Lys Phe His Arg Ala Ser Val Leu Phe Ala Asn Glu Lys Tyr Lys
705                 710                 715                 720

Ser Ala Leu Gln Glu Leu Glu Glu Leu Lys Gln Ile Val Pro Lys Glu
                725                 730                 735

Ser Leu Val Tyr Phe Leu Ile Gly Lys Val Tyr Lys Lys Leu Gly Gln
            740                 745                 750

Thr His Leu Ala Leu Met Asn Phe Ser Trp Ala Met Asp Leu Asp Pro
```

```
                755                 760                 765
Lys Gly Ala Asn Asn Gln Ile Lys Glu Ala Ile Asp Lys Arg Tyr Leu
    770                 775                 780

Pro Asp Asp Glu Glu Pro Ile Thr Gln Glu Glu Gln Ile Met Gly Thr
785                 790                 795                 800

Asp Glu Ser Gln Glu Ser Ser Met Thr Asp Ala Asp Asp Thr Gln Leu
                805                 810                 815

His Ala Ala Glu Ser Asp Glu Phe
            820

<210> SEQ ID NO 3
<211> LENGTH: 830
<212> TYPE: PRT
<213> ORGANISM: Homo sapiens

<400> SEQUENCE: 3

Met Thr Val Leu Gln Glu Pro Val Gln Ala Ala Ile Trp Gln Ala Leu
1               5                   10                  15

Asn His Tyr Ala Tyr Arg Asp Ala Val Phe Leu Ala Glu Arg Leu Tyr
                20                  25                  30

Ala Glu Val His Ser Glu Ala Leu Phe Leu Leu Ala Thr Cys Tyr
                35                  40                  45

Tyr Arg Ser Gly Lys Ala Tyr Lys Ala Tyr Arg Leu Leu Lys Gly His
    50                  55                  60

Ser Cys Thr Thr Pro Gln Cys Lys Tyr Leu Leu Ala Lys Cys Cys Val
65                  70                  75                  80

Asp Leu Ser Lys Leu Ala Glu Gly Glu Gln Ile Leu Ser Gly Gly Val
                85                  90                  95

Phe Asn Lys Gln Lys Ser His Asp Asp Ile Val Thr Glu Phe Gly Asp
            100                 105                 110

Ser Ala Cys Phe Thr Leu Ser Leu Leu Gly His Val Tyr Cys Lys Thr
        115                 120                 125

Asp Arg Leu Ala Lys Gly Ser Glu Cys Tyr Gln Lys Ser Leu Ser Leu
    130                 135                 140

Asn Pro Phe Leu Trp Ser Pro Phe Glu Ser Leu Cys Glu Ile Gly Glu
145                 150                 155                 160

Lys Pro Asp Pro Asp Gln Thr Phe Lys Phe Thr Ser Leu Gln Asn Phe
                165                 170                 175

Ser Asn Cys Leu Pro Asn Ser Cys Thr Thr Gln Val Pro Asn His Ser
            180                 185                 190

Leu Ser His Arg Gln Pro Glu Thr Val Leu Thr Glu Thr Pro Gln Asp
        195                 200                 205

Thr Ile Glu Leu Asn Arg Leu Asn Leu Glu Ser Ser Asn Ser Lys Tyr
    210                 215                 220

Ser Leu Asn Thr Asp Ser Ser Val Ser Tyr Ile Asp Ser Ala Val Ile
225                 230                 235                 240

Ser Pro Asp Thr Val Pro Leu Gly Thr Gly Thr Ser Ile Leu Ser Lys
                245                 250                 255

Gln Val Gln Asn Lys Pro Lys Thr Gly Arg Ser Leu Leu Gly Gly Pro
            260                 265                 270

Ala Ala Leu Ser Pro Leu Thr Pro Ser Phe Gly Ile Leu Pro Leu Glu
        275                 280                 285

Thr Pro Ser Pro Gly Asp Gly Ser Tyr Leu Gln Asn Tyr Thr Asn Thr
    290                 295                 300
```

```
Pro Pro Val Ile Asp Val Pro Ser Thr Gly Ala Pro Ser Lys Lys Thr
305                 310                 315                 320

Phe Arg Val Leu Gln Ser Val Ala Arg Ile Gly Gln Thr Gly Thr Lys
                325                 330                 335

Ser Val Phe Ser Gln Ser Gly Asn Ser Arg Glu Val Thr Pro Ile Leu
            340                 345                 350

Ala Gln Thr Gln Ser Ser Gly Pro Gln Thr Ser Thr Pro Gln Val
        355                 360                 365

Leu Ser Pro Thr Ile Thr Ser Pro Pro Asn Ala Leu Pro Arg Arg Ser
    370                 375                 380

Ser Arg Leu Phe Thr Ser Asp Ser Ser Thr Thr Lys Glu Asn Ser Lys
385                 390                 395                 400

Lys Leu Lys Met Lys Phe Pro Pro Glu Ile Pro Asn Arg Lys Thr Lys
                405                 410                 415

Ser Lys Thr Asn Lys Gly Gly Ile Thr Gln Pro Asn Ile Asn Asp Ser
            420                 425                 430

Leu Glu Ile Thr Lys Leu Asp Ser Ser Ile Ile Ser Glu Gly Lys Ile
        435                 440                 445

Ser Thr Ile Thr Pro Gln Ile Gln Ala Phe Asn Leu Gln Lys Ala Ala
    450                 455                 460

Ala Glu Gly Leu Met Ser Leu Leu Arg Glu Met Gly Lys Gly Tyr Leu
465                 470                 475                 480

Ala Leu Cys Ser Tyr Asn Cys Lys Glu Ala Ile Asn Ile Leu Ser His
                485                 490                 495

Leu Pro Ser His His Tyr Asn Thr Gly Trp Val Leu Cys Gln Ile Gly
            500                 505                 510

Arg Ala Tyr Phe Glu Leu Ser Glu Tyr Met Gln Ala Glu Arg Ile Phe
        515                 520                 525

Ser Glu Val Arg Arg Ile Glu Asn Tyr Arg Val Glu Gly Met Glu Ile
    530                 535                 540

Tyr Ser Thr Thr Leu Trp His Leu Gln Lys Asp Val Ala Leu Ser Val
545                 550                 555                 560

Leu Ser Lys Asp Leu Thr Asp Met Asp Lys Asn Ser Pro Glu Ala Trp
                565                 570                 575

Cys Ala Ala Gly Asn Cys Phe Ser Leu Gln Arg Glu His Asp Ile Ala
            580                 585                 590

Ile Lys Phe Phe Gln Arg Ala Ile Gln Val Asp Pro Asn Tyr Ala Tyr
        595                 600                 605

Ala Tyr Thr Leu Leu Gly His Glu Phe Val Leu Thr Glu Glu Leu Asp
610                 615                 620

Lys Ala Leu Ala Cys Phe Arg Asn Ala Ile Arg Val Asn Pro Arg His
625                 630                 635                 640

Tyr Asn Ala Trp Tyr Gly Leu Gly Met Ile Tyr Tyr Lys Gln Glu Lys
                645                 650                 655

Phe Ser Leu Ala Glu Met His Phe Gln Lys Ala Leu Asp Ile Asn Pro
            660                 665                 670

Gln Ser Ser Val Leu Leu Cys His Ile Gly Val Val Gln His Ala Leu
        675                 680                 685

Lys Lys Ser Glu Lys Ala Leu Asp Thr Leu Asn Lys Ala Ile Val Ile
        690                 695                 700

Asp Pro Lys Asn Pro Leu Cys Lys Phe His Arg Ala Ser Val Leu Phe
705                 710                 715                 720

Ala Asn Glu Lys Tyr Lys Ser Ala Leu Gln Glu Leu Glu Glu Leu Lys
```

```
                        725                 730                 735
Gln Ile Val Pro Lys Glu Ser Leu Val Tyr Phe Leu Ile Gly Lys Val
            740                 745                 750

Tyr Lys Lys Leu Gly Gln Thr His Leu Ala Leu Met Asn Phe Ser Trp
        755                 760                 765

Ala Met Asp Leu Asp Pro Lys Gly Ala Asn Asn Gln Ile Lys Glu Ala
    770                 775                 780

Ile Asp Lys Arg Tyr Leu Pro Asp Asp Glu Glu Pro Ile Thr Gln Glu
785                 790                 795                 800

Glu Gln Ile Met Gly Thr Asp Glu Ser Gln Glu Ser Ser Met Thr Asp
                805                 810                 815

Ala Asp Asp Thr Gln Leu His Ala Ala Glu Ser Asp Glu Phe
            820                 825                 830

<210> SEQ ID NO 4
<211> LENGTH: 526
<212> TYPE: PRT
<213> ORGANISM: Homo sapiens

<400> SEQUENCE: 4

Met Glu Glu Pro Ile Asn Lys Arg Leu Phe Glu Lys Tyr Leu Lys Asp
1               5                   10                  15

Glu Ser Gly Phe Lys Asp Pro Ser Ser Asp Trp Glu Met Ser Gln Ser
            20                  25                  30

Ser Ile Lys Ser Ser Ile Cys Leu Leu Arg Gly Lys Ile Tyr Asp Ala
        35                  40                  45

Leu Asp Asn Arg Thr Leu Ala Thr Tyr Ser Tyr Lys Glu Ala Leu Lys
    50                  55                  60

Leu Asp Val Tyr Cys Phe Glu Ala Phe Asp Leu Leu Thr Ser His His
65                  70                  75                  80

Met Leu Thr Ala Gln Glu Lys Glu Leu Leu Glu Ser Leu Pro Leu
                85                  90                  95

Ser Lys Leu Cys Asn Glu Glu Gln Glu Leu Leu Arg Phe Leu Phe Glu
            100                 105                 110

Asn Lys Leu Lys Lys Tyr Asn Lys Pro Ser Glu Thr Val Ile Pro Glu
        115                 120                 125

Ser Val Asp Gly Leu Gln Glu Asn Leu Asp Val Val Val Ser Leu Ala
    130                 135                 140

Glu Arg His Tyr Tyr Asn Cys Asp Phe Lys Met Cys Tyr Lys Leu Thr
145                 150                 155                 160

Ser Val Val Met Glu Lys Asp Pro Phe His Ala Ser Cys Leu Pro Val
                165                 170                 175

His Ile Gly Thr Leu Val Glu Leu Asn Lys Ala Asn Glu Leu Phe Tyr
            180                 185                 190

Leu Ser His Lys Leu Val Asp Leu Tyr Pro Ser Asn Pro Val Ser Trp
        195                 200                 205

Phe Ala Val Gly Cys Tyr Tyr Leu Met Val Gly His Lys Asn Glu His
    210                 215                 220

Ala Arg Arg Tyr Leu Ser Lys Ala Thr Thr Leu Glu Lys Thr Tyr Gly
225                 230                 235                 240

Pro Ala Trp Ile Ala Tyr Gly His Ser Phe Ala Val Glu Ser Glu His
                245                 250                 255

Asp Gln Ala Met Ala Ala Tyr Phe Thr Ala Ala Gln Leu Met Lys Gly
            260                 265                 270
```

```
Cys His Leu Pro Met Leu Tyr Ile Gly Leu Glu Tyr Gly Leu Thr Asn
            275                 280                 285

Asn Ser Lys Leu Ala Glu Arg Phe Phe Ser Gln Ala Leu Ser Ile Ala
        290                 295                 300

Pro Glu Asp Pro Phe Val Met His Glu Val Gly Val Ala Phe Gln
305                 310                 315                 320

Asn Gly Glu Trp Lys Thr Ala Glu Lys Trp Phe Leu Asp Ala Leu Glu
                325                 330                 335

Lys Ile Lys Ala Ile Gly Asn Glu Val Thr Val Asp Lys Trp Glu Pro
                340                 345                 350

Leu Leu Asn Asn Leu Gly His Val Cys Arg Lys Leu Lys Lys Tyr Ala
                355                 360                 365

Glu Ala Leu Asp Tyr His Arg Gln Ala Leu Val Leu Ile Pro Gln Asn
        370                 375                 380

Ala Ser Thr Tyr Ser Ala Ile Gly Tyr Ile His Ser Leu Met Gly Asn
385                 390                 395                 400

Phe Glu Asn Ala Val Asp Tyr Phe His Thr Ala Leu Gly Leu Arg Arg
                405                 410                 415

Asp Asp Thr Phe Ser Val Thr Met Leu Gly His Cys Ile Glu Met Tyr
                420                 425                 430

Ile Gly Asp Ser Glu Ala Tyr Ile Gly Ala Asp Ile Lys Asp Lys Leu
        435                 440                 445

Lys Cys Tyr Asp Phe Asp Val His Thr Met Lys Thr Leu Lys Asn Ile
        450                 455                 460

Ile Ser Pro Pro Trp Asp Phe Arg Glu Phe Glu Val Glu Lys Gln Thr
465                 470                 475                 480

Ala Glu Glu Thr Gly Leu Thr Pro Leu Glu Thr Ser Arg Lys Thr Pro
                485                 490                 495

Asp Ser Arg Pro Ser Leu Glu Glu Thr Phe Glu Ile Glu Met Asn Glu
                500                 505                 510

Ser Asp Met Met Leu Glu Thr Ser Met Ser Asp His Ser Thr
            515                 520                 525

<210> SEQ ID NO 5
<211> LENGTH: 620
<212> TYPE: PRT
<213> ORGANISM: Homo sapiens

<400> SEQUENCE: 5

Met Asn Leu Glu Arg Leu Arg Lys Arg Val Arg Gln Tyr Leu Asp Gln
1               5                   10                  15

Gln Gln Tyr Gln Ser Ala Leu Phe Trp Ala Asp Lys Val Ala Ser Leu
            20                  25                  30

Ser Arg Glu Glu Pro Gln Asp Ile Tyr Trp Leu Ala Gln Cys Leu Tyr
        35                  40                  45

Leu Thr Ala Gln Tyr His Arg Ala Ala His Ala Leu Arg Ser Arg Lys
    50                  55                  60

Leu Asp Lys Leu Tyr Glu Ala Cys Arg Tyr Leu Ala Ala Arg Cys His
65              70                  75                  80

Tyr Ala Ala Lys Glu His Gln Gln Ala Leu Asp Val Leu Asp Met Glu
                85                  90                  95

Glu Pro Ile Asn Lys Arg Leu Phe Glu Lys Tyr Leu Lys Asp Glu Ser
            100                 105                 110

Gly Phe Lys Asp Pro Ser Ser Asp Trp Glu Met Ser Gln Ser Ser Ile
        115                 120                 125
```

```
Lys Ser Ser Ile Cys Leu Leu Arg Gly Lys Ile Tyr Asp Ala Leu Asp
    130                 135                 140

Asn Arg Thr Leu Ala Thr Tyr Ser Tyr Lys Glu Ala Leu Lys Leu Asp
145                 150                 155                 160

Val Tyr Cys Phe Glu Ala Phe Asp Leu Leu Thr Ser His His Met Leu
                165                 170                 175

Thr Ala Gln Glu Glu Lys Glu Leu Leu Glu Ser Leu Pro Leu Ser Lys
            180                 185                 190

Leu Cys Asn Glu Glu Gln Glu Leu Leu Arg Phe Leu Phe Glu Asn Lys
        195                 200                 205

Leu Lys Lys Tyr Asn Lys Pro Ser Glu Thr Val Ile Pro Glu Ser Val
210                 215                 220

Asp Gly Leu Gln Glu Asn Leu Asp Val Val Ser Leu Ala Glu Arg
225                 230                 235                 240

His Tyr Tyr Asn Cys Asp Phe Lys Met Cys Tyr Lys Leu Thr Ser Val
                245                 250                 255

Val Met Glu Lys Asp Pro Phe His Ala Ser Cys Leu Pro Val His Ile
            260                 265                 270

Gly Thr Leu Val Glu Leu Asn Lys Ala Asn Glu Leu Phe Tyr Leu Ser
        275                 280                 285

His Lys Leu Val Asp Leu Tyr Pro Ser Asn Pro Val Ser Trp Phe Ala
290                 295                 300

Val Gly Cys Tyr Tyr Leu Met Val Gly His Lys Asn Glu His Ala Arg
305                 310                 315                 320

Arg Tyr Leu Ser Lys Ala Thr Thr Leu Glu Lys Thr Tyr Gly Pro Ala
                325                 330                 335

Trp Ile Ala Tyr Gly His Ser Phe Ala Val Glu Ser Glu His Asp Gln
            340                 345                 350

Ala Met Ala Ala Tyr Phe Thr Ala Ala Gln Leu Met Lys Gly Cys His
        355                 360                 365

Leu Pro Met Leu Tyr Ile Gly Leu Glu Tyr Gly Leu Thr Asn Asn Ser
370                 375                 380

Lys Leu Ala Glu Arg Phe Phe Ser Gln Ala Leu Ser Ile Ala Pro Glu
385                 390                 395                 400

Asp Pro Phe Val Met His Glu Val Gly Val Val Ala Phe Gln Asn Gly
                405                 410                 415

Glu Trp Lys Thr Ala Glu Lys Trp Phe Leu Asp Ala Leu Glu Lys Ile
            420                 425                 430

Lys Ala Ile Gly Asn Glu Val Thr Val Asp Lys Trp Glu Pro Leu Leu
        435                 440                 445

Asn Asn Leu Gly His Val Cys Arg Lys Leu Lys Lys Tyr Ala Glu Ala
450                 455                 460

Leu Asp Tyr His Arg Gln Ala Leu Val Leu Ile Pro Gln Asn Ala Ser
465                 470                 475                 480

Thr Tyr Ser Ala Ile Gly Tyr Ile His Ser Leu Met Gly Asn Phe Glu
                485                 490                 495

Asn Ala Val Asp Tyr Phe His Thr Ala Leu Gly Leu Arg Arg Asp Asp
            500                 505                 510

Thr Phe Ser Val Thr Met Leu Gly His Cys Ile Glu Met Tyr Ile Gly
        515                 520                 525

Asp Ser Glu Ala Tyr Ile Gly Ala Asp Ile Lys Asp Lys Leu Lys Cys
530                 535                 540
```

```
Tyr Asp Phe Asp Val His Thr Met Lys Thr Leu Lys Asn Ile Ile Ser
545                 550                 555                 560

Pro Pro Trp Asp Phe Arg Glu Phe Glu Val Glu Lys Gln Thr Ala Glu
            565                 570                 575

Glu Thr Gly Leu Thr Pro Leu Glu Thr Ser Arg Lys Thr Pro Asp Ser
        580                 585                 590

Arg Pro Ser Leu Glu Glu Thr Phe Glu Ile Glu Met Asn Glu Ser Asp
    595                 600                 605

Met Met Leu Glu Thr Ser Met Ser Asp His Ser Thr
            610                 615                 620

<210> SEQ ID NO 6
<211> LENGTH: 620
<212> TYPE: PRT
<213> ORGANISM: Homo sapiens

<400> SEQUENCE: 6

Met Asn Leu Glu Arg Leu Arg Lys Arg Val Arg Gln Tyr Leu Asp Gln
1               5                   10                  15

Gln Gln Tyr Gln Ser Ala Leu Phe Trp Ala Asp Lys Val Ala Ser Leu
            20                  25                  30

Ser Arg Glu Glu Pro Gln Asp Ile Tyr Trp Leu Ala Gln Cys Leu Tyr
        35                  40                  45

Leu Thr Ala Gln Tyr His Arg Ala Ala His Ala Leu Arg Ser Arg Lys
50                  55                  60

Leu Asp Lys Leu Tyr Glu Ala Cys Arg Tyr Leu Ala Ala Arg Cys His
65                  70                  75                  80

Tyr Ala Ala Lys Glu His Gln Gln Ala Leu Asp Val Leu Asp Met Glu
                85                  90                  95

Glu Pro Ile Asn Lys Arg Leu Phe Glu Lys Tyr Leu Lys Asp Glu Ser
            100                 105                 110

Gly Phe Lys Asp Pro Ser Ser Asp Trp Glu Met Ser Gln Ser Ser Ile
        115                 120                 125

Lys Ser Ser Ile Cys Leu Leu Arg Gly Lys Ile Tyr Asp Ala Leu Asp
130                 135                 140

Asn Arg Thr Leu Ala Thr Tyr Ser Tyr Lys Glu Ala Leu Lys Leu Asp
145                 150                 155                 160

Val Tyr Cys Phe Glu Ala Phe Asp Leu Leu Thr Ser His His Met Leu
                165                 170                 175

Thr Ala Gln Glu Glu Lys Glu Leu Leu Glu Ser Leu Pro Leu Ser Lys
            180                 185                 190

Leu Cys Asn Glu Glu Gln Glu Leu Leu Arg Phe Leu Phe Glu Asn Lys
        195                 200                 205

Leu Lys Lys Tyr Asn Lys Pro Ser Glu Thr Val Ile Pro Glu Ser Val
210                 215                 220

Asp Gly Leu Gln Glu Asn Leu Asp Val Val Ser Leu Ala Glu Arg
225                 230                 235                 240

His Tyr Asn Cys Asp Phe Lys Met Cys Tyr Lys Leu Thr Ser Val
                245                 250                 255

Val Met Glu Lys Asp Pro Phe His Ala Ser Cys Leu Pro Val His Ile
            260                 265                 270

Gly Thr Leu Val Glu Leu Asn Lys Ala Asn Glu Leu Phe Tyr Leu Ser
        275                 280                 285

His Lys Leu Val Asp Leu Tyr Pro Ser Asn Pro Val Ser Trp Phe Ala
    290                 295                 300
```

Val Gly Cys Tyr Tyr Leu Met Val Gly His Lys Asn Glu His Ala Arg
305                 310                 315                 320

Arg Tyr Leu Ser Lys Ala Thr Thr Leu Glu Lys Thr Tyr Gly Pro Ala
            325                 330                 335

Trp Ile Ala Tyr Gly His Ser Phe Ala Val Glu Ser Glu His Asp Gln
        340                 345                 350

Ala Met Ala Ala Tyr Phe Thr Ala Ala Gln Leu Met Lys Gly Cys His
    355                 360                 365

Leu Pro Met Leu Tyr Ile Gly Leu Glu Tyr Gly Leu Thr Asn Asn Ser
370                 375                 380

Lys Leu Ala Glu Arg Phe Phe Ser Gln Ala Leu Ser Ile Ala Pro Glu
385                 390                 395                 400

Asp Pro Phe Val Met His Glu Val Gly Val Val Ala Phe Gln Asn Gly
                405                 410                 415

Glu Trp Lys Thr Ala Glu Lys Trp Phe Leu Asp Ala Leu Glu Lys Ile
            420                 425                 430

Lys Ala Ile Gly Asn Glu Val Thr Val Asp Lys Trp Glu Pro Leu Leu
        435                 440                 445

Asn Asn Leu Gly His Val Cys Arg Lys Leu Lys Lys Tyr Ala Glu Ala
    450                 455                 460

Leu Asp Tyr His Arg Gln Ala Leu Val Leu Ile Pro Gln Asn Ala Ser
465                 470                 475                 480

Thr Tyr Ser Ala Ile Gly Tyr Ile His Ser Leu Met Gly Asn Phe Glu
                485                 490                 495

Asn Ala Val Asp Tyr Phe His Thr Ala Leu Gly Leu Arg Arg Asp Asp
            500                 505                 510

Thr Phe Ser Val Thr Met Leu Gly His Cys Ile Glu Met Tyr Ile Gly
        515                 520                 525

Asp Ser Glu Ala Tyr Ile Gly Ala Asp Ile Lys Asp Lys Leu Lys Cys
    530                 535                 540

Tyr Asp Phe Asp Val His Thr Met Lys Thr Leu Lys Asn Ile Ile Ser
545                 550                 555                 560

Pro Pro Trp Asp Phe Arg Glu Phe Glu Val Glu Lys Gln Thr Ala Glu
                565                 570                 575

Glu Thr Gly Leu Thr Pro Leu Glu Thr Ser Arg Lys Thr Pro Asp Ser
            580                 585                 590

Arg Pro Ser Leu Glu Glu Thr Phe Glu Ile Glu Met Asn Glu Ser Asp
        595                 600                 605

Met Met Leu Glu Thr Ser Met Ser Asp His Ser Thr
    610                 615                 620

<210> SEQ ID NO 7
<211> LENGTH: 620
<212> TYPE: PRT
<213> ORGANISM: Homo sapiens

<400> SEQUENCE: 7

Met Asn Leu Glu Arg Leu Arg Lys Arg Val Arg Gln Tyr Leu Asp Gln
1               5                   10                  15

Gln Gln Tyr Gln Ser Ala Leu Phe Trp Ala Asp Lys Val Ala Ser Leu
            20                  25                  30

Ser Arg Glu Glu Pro Gln Asp Ile Tyr Trp Leu Ala Gln Cys Leu Tyr
        35                  40                  45

Leu Thr Ala Gln Tyr His Arg Ala Ala His Ala Leu Arg Ser Arg Lys

```
            50                  55                  60
Leu Asp Lys Leu Tyr Glu Ala Cys Arg Tyr Leu Ala Ala Arg Cys His
 65                  70                  75                  80

Tyr Ala Ala Lys Glu His Gln Gln Ala Leu Asp Val Leu Asp Met Glu
                 85                  90                  95

Glu Pro Ile Asn Lys Arg Leu Phe Glu Lys Tyr Leu Lys Asp Glu Ser
                100                 105                 110

Gly Phe Lys Asp Pro Ser Ser Asp Trp Glu Met Ser Gln Ser Ser Ile
            115                 120                 125

Lys Ser Ser Ile Cys Leu Leu Arg Gly Lys Ile Tyr Asp Ala Leu Asp
130                 135                 140

Asn Arg Thr Leu Ala Thr Tyr Ser Tyr Lys Glu Ala Leu Lys Leu Asp
145                 150                 155                 160

Val Tyr Cys Phe Glu Ala Phe Asp Leu Leu Thr Ser His His Met Leu
                165                 170                 175

Thr Ala Gln Glu Glu Lys Glu Leu Leu Glu Ser Leu Pro Leu Ser Lys
            180                 185                 190

Leu Cys Asn Glu Glu Gln Glu Leu Leu Arg Phe Leu Phe Glu Asn Lys
            195                 200                 205

Leu Lys Lys Tyr Asn Lys Pro Ser Glu Thr Val Ile Pro Glu Ser Val
210                 215                 220

Asp Gly Leu Gln Glu Asn Leu Asp Val Val Ser Leu Ala Glu Arg
225                 230                 235                 240

His Tyr Tyr Asn Cys Asp Phe Lys Met Cys Tyr Lys Leu Thr Ser Val
                245                 250                 255

Val Met Glu Lys Asp Pro Phe His Ala Ser Cys Leu Pro Val His Ile
            260                 265                 270

Gly Thr Leu Val Glu Leu Asn Lys Ala Asn Glu Leu Phe Tyr Leu Ser
            275                 280                 285

His Lys Leu Val Asp Leu Tyr Pro Ser Asn Pro Val Ser Trp Phe Ala
290                 295                 300

Val Gly Cys Tyr Tyr Leu Met Val Gly His Lys Asn Glu His Ala Arg
305                 310                 315                 320

Arg Tyr Leu Ser Lys Ala Thr Thr Leu Glu Lys Thr Tyr Gly Pro Ala
                325                 330                 335

Trp Ile Ala Tyr Gly His Ser Phe Ala Val Glu Ser Glu His Asp Gln
            340                 345                 350

Ala Met Ala Ala Tyr Phe Thr Ala Ala Gln Leu Met Lys Gly Cys His
            355                 360                 365

Leu Pro Met Leu Tyr Ile Gly Leu Glu Tyr Gly Leu Thr Asn Asn Ser
370                 375                 380

Lys Leu Ala Glu Arg Phe Phe Ser Gln Ala Leu Ser Ile Ala Pro Glu
385                 390                 395                 400

Asp Pro Phe Val Met His Glu Val Gly Val Val Ala Phe Gln Asn Gly
                405                 410                 415

Glu Trp Lys Thr Ala Glu Lys Trp Phe Leu Asp Ala Leu Glu Lys Ile
            420                 425                 430

Lys Ala Ile Gly Asn Glu Val Thr Val Asp Lys Trp Glu Pro Leu Leu
            435                 440                 445

Asn Asn Leu Gly His Val Cys Arg Lys Leu Lys Lys Tyr Ala Glu Ala
450                 455                 460

Leu Asp Tyr His Arg Gln Ala Leu Val Leu Ile Pro Gln Asn Ala Ser
465                 470                 475                 480
```

```
Thr Tyr Ser Ala Ile Gly Tyr Ile His Ser Leu Met Gly Asn Phe Glu
            485                 490                 495

Asn Ala Val Asp Tyr Phe His Thr Ala Leu Gly Leu Arg Arg Asp Asp
        500                 505                 510

Thr Phe Ser Val Thr Met Leu Gly His Cys Ile Glu Met Tyr Ile Gly
        515                 520                 525

Asp Ser Glu Ala Tyr Ile Gly Ala Asp Ile Lys Asp Lys Leu Lys Cys
        530                 535                 540

Tyr Asp Phe Asp Val His Thr Met Lys Thr Leu Lys Asn Ile Ile Ser
545                 550                 555                 560

Pro Pro Trp Asp Phe Arg Glu Phe Glu Val Lys Gln Thr Ala Glu
            565                 570                 575

Glu Thr Gly Leu Thr Pro Leu Glu Thr Ser Arg Lys Thr Pro Asp Ser
        580                 585                 590

Arg Pro Ser Leu Glu Glu Thr Phe Glu Ile Glu Met Asn Glu Ser Asp
        595                 600                 605

Met Met Leu Glu Thr Ser Met Ser Asp His Ser Thr
        610                 615                 620

<210> SEQ ID NO 8
<211> LENGTH: 564
<212> TYPE: PRT
<213> ORGANISM: Homo sapiens

<400> SEQUENCE: 8

Asn Val Ile Asp His Val Arg Asp Met Ala Ala Gly Leu His Ser
1               5                   10                  15

Asn Val Arg Leu Leu Ser Ser Leu Leu Leu Thr Met Ser Asn Asn Asn
            20                  25                  30

Pro Glu Leu Phe Ser Pro Pro Gln Lys Tyr Gln Leu Val Tyr His
        35                  40                  45

Ala Asp Ser Leu Phe His Asp Lys Glu Tyr Arg Asn Ala Val Ser Lys
    50                  55                  60

Tyr Thr Met Ala Leu Gln Gln Lys Lys Ala Leu Ser Lys Thr Ser Lys
65                  70                  75                  80

Val Arg Pro Ser Thr Gly Asn Ser Ala Ser Thr Pro Gln Ser Gln Cys
                85                  90                  95

Leu Pro Ser Glu Ile Glu Val Lys Tyr Lys Met Ala Glu Cys Tyr Thr
            100                 105                 110

Met Leu Lys Gln Asp Lys Asp Ala Ile Ala Ile Leu Asp Gly Ile Pro
        115                 120                 125

Ser Arg Gln Arg Thr Pro Lys Ile Asn Met Met Leu Ala Asn Leu Tyr
    130                 135                 140

Lys Lys Ala Gly Gln Glu Arg Pro Ser Val Thr Ser Tyr Lys Glu Val
145                 150                 155                 160

Leu Arg Gln Cys Pro Leu Ala Leu Asp Ala Ile Leu Gly Leu Leu Ser
                165                 170                 175

Leu Ser Val Lys Gly Ala Glu Val Ala Ser Met Thr Met Asn Val Ile
            180                 185                 190

Gln Thr Val Pro Asn Leu Asp Trp Leu Ser Val Trp Ile Lys Ala Tyr
        195                 200                 205

Ala Phe Val His Thr Gly Asp Asn Ser Arg Ala Ile Ser Thr Ile Cys
    210                 215                 220

Ser Leu Glu Lys Lys Ser Leu Leu Arg Asp Asn Val Asp Leu Leu Gly
```

```
            225                 230                 235                 240
    Ser Leu Ala Asp Leu Tyr Phe Arg Ala Gly Asp Asn Lys Asn Ser Val
                    245                 250                 255

Leu Lys Phe Glu Gln Ala Gln Met Leu Asp Pro Tyr Leu Ile Lys Gly
                260                 265                 270

Met Asp Val Tyr Gly Tyr Leu Ala Arg Glu Gly Arg Leu Glu Asp
                275                 280                 285

Val Glu Asn Leu Gly Cys Arg Leu Phe Asn Ile Ser Asp Gln His Ala
                290                 295                 300

Glu Pro Trp Val Val Ser Gly Cys His Ser Phe Tyr Ser Lys Arg Tyr
    305                 310                 315                 320

Ser Arg Ala Leu Tyr Leu Gly Ala Lys Ala Ile Gln Leu Asn Ser Asn
                    325                 330                 335

Ser Val Gln Ala Leu Leu Leu Lys Gly Ala Ala Leu Arg Asn Met Gly
                340                 345                 350

Arg Val Gln Glu Ala Ile Ile His Phe Arg Glu Ala Ile Arg Leu Ala
                355                 360                 365

Pro Cys Arg Leu Asp Cys Tyr Glu Gly Leu Ile Glu Cys Tyr Leu Ala
                370                 375                 380

Ser Asn Ser Ile Arg Glu Ala Met Val Met Ala Asn Asn Val Tyr Lys
    385                 390                 395                 400

Thr Leu Gly Ala Asn Ala Gln Thr Leu Thr Leu Leu Ala Thr Val Cys
                    405                 410                 415

Leu Glu Asp Pro Val Thr Gln Glu Lys Ala Lys Thr Leu Leu Asp Lys
                420                 425                 430

Ala Leu Thr Gln Arg Pro Asp Tyr Ile Lys Ala Val Val Lys Lys Ala
                435                 440                 445

Glu Leu Leu Ser Arg Glu Gln Lys Tyr Glu Asp Gly Ile Ala Leu Leu
                450                 455                 460

Arg Asn Ala Leu Ala Asn Gln Ser Asp Cys Val Leu His Arg Ile Leu
    465                 470                 475                 480

Gly Asp Phe Leu Val Ala Val Asn Glu Tyr Gln Glu Ala Met Asp Gln
                    485                 490                 495

Tyr Ser Ile Ala Leu Ser Leu Asp Pro Asn Asp Gln Lys Ser Leu Glu
                500                 505                 510

Gly Met Gln Lys Met Glu Lys Glu Glu Ser Pro Thr Asp Ala Thr Gln
                515                 520                 525

Glu Glu Asp Val Asp Asp Met Glu Gly Ser Gly Glu Glu Gly Asp Leu
                530                 535                 540

Glu Gly Ser Asp Ser Glu Ala Ala Gln Trp Ala Asp Gln Glu Gln Trp
    545                 550                 555                 560

Phe Gly Met Gln

<210> SEQ ID NO 9
<211> LENGTH: 564
<212> TYPE: PRT
<213> ORGANISM: Homo sapiens

<400> SEQUENCE: 9

Asn Val Ile Asp His Val Arg Asp Met Ala Ala Ala Gly Leu His Ser
    1               5                   10                  15

Asn Val Arg Leu Leu Ser Ser Leu Leu Leu Thr Met Ser Asn Asn Asn
                20                  25                  30

Pro Glu Leu Phe Ser Pro Pro Gln Lys Tyr Gln Leu Leu Val Tyr His
```

```
                35                  40                  45
Ala Asp Ser Leu Phe His Asp Lys Glu Tyr Arg Asn Ala Val Ser Lys
 50                  55                  60

Tyr Thr Met Ala Leu Gln Gln Lys Lys Ala Leu Ser Lys Thr Ser Lys
 65                  70                  75                  80

Val Arg Pro Ser Thr Gly Asn Ser Ala Ser Thr Pro Gln Ser Gln Cys
                 85                  90                  95

Leu Pro Ser Glu Ile Glu Val Lys Tyr Lys Met Ala Glu Cys Tyr Thr
                100                 105                 110

Met Leu Lys Gln Asp Lys Asp Ala Ile Ala Ile Leu Asp Gly Ile Pro
                115                 120                 125

Ser Arg Gln Arg Thr Pro Lys Ile Asn Met Met Leu Ala Asn Leu Tyr
130                 135                 140

Lys Lys Ala Gly Gln Glu Arg Pro Ser Val Thr Ser Tyr Lys Glu Val
145                 150                 155                 160

Leu Arg Gln Cys Pro Leu Ala Leu Asp Ala Ile Leu Gly Leu Leu Ser
                165                 170                 175

Leu Ser Val Lys Gly Ala Glu Val Ala Ser Met Thr Met Asn Val Ile
                180                 185                 190

Gln Thr Val Pro Asn Leu Asp Trp Leu Ser Val Trp Ile Lys Ala Tyr
                195                 200                 205

Ala Phe Val His Thr Gly Asp Asn Ser Arg Ala Ile Ser Thr Ile Cys
210                 215                 220

Ser Leu Glu Lys Lys Ser Leu Leu Arg Asp Asn Val Asp Leu Leu Gly
225                 230                 235                 240

Ser Leu Ala Asp Leu Tyr Phe Arg Ala Gly Asp Asn Lys Asn Ser Val
                245                 250                 255

Leu Lys Phe Glu Gln Ala Gln Met Leu Asp Pro Tyr Leu Ile Lys Gly
                260                 265                 270

Met Asp Val Tyr Gly Tyr Leu Leu Ala Arg Glu Gly Arg Leu Glu Asp
                275                 280                 285

Val Glu Asn Leu Gly Cys Arg Leu Phe Asn Ile Ser Asp Gln His Ala
290                 295                 300

Glu Pro Trp Val Val Ser Gly Cys His Ser Phe Tyr Ser Lys Arg Tyr
305                 310                 315                 320

Ser Arg Ala Leu Tyr Leu Gly Ala Lys Ala Ile Gln Leu Asn Ser Asn
                325                 330                 335

Ser Val Gln Ala Leu Leu Leu Lys Gly Ala Ala Leu Arg Asn Met Gly
                340                 345                 350

Arg Val Gln Glu Ala Ile Ile His Phe Arg Glu Ala Ile Arg Leu Ala
                355                 360                 365

Pro Cys Arg Leu Asp Cys Tyr Glu Gly Leu Ile Glu Cys Tyr Leu Ala
                370                 375                 380

Ser Asn Ser Ile Arg Glu Ala Met Val Met Ala Asn Asn Val Tyr Lys
385                 390                 395                 400

Thr Leu Gly Ala Asn Ala Gln Thr Leu Thr Leu Leu Ala Thr Val Cys
                405                 410                 415

Leu Glu Asp Pro Val Thr Gln Glu Lys Ala Lys Thr Leu Leu Asp Lys
                420                 425                 430

Ala Leu Thr Gln Arg Pro Asp Tyr Ile Lys Ala Val Val Lys Lys Ala
                435                 440                 445

Glu Leu Leu Ser Arg Glu Gln Lys Tyr Glu Asp Gly Ile Ala Leu Leu
450                 455                 460
```

Arg Asn Ala Leu Ala Asn Gln Ser Asp Cys Val Leu His Arg Ile Leu
465                 470                 475                 480

Gly Asp Phe Leu Val Ala Val Asn Glu Tyr Gln Glu Ala Met Asp Gln
                485                 490                 495

Tyr Ser Ile Ala Leu Ser Leu Asp Pro Asn Asp Gln Lys Ser Leu Glu
            500                 505                 510

Gly Met Gln Lys Met Glu Lys Glu Ser Pro Thr Asp Ala Thr Gln
        515                 520                 525

Glu Glu Asp Val Asp Asp Met Glu Gly Ser Gly Glu Gly Asp Leu
    530                 535                 540

Glu Gly Ser Asp Ser Glu Ala Ala Gln Trp Ala Asp Glu Gln Trp
545                 550                 555                 560

Phe Gly Met Gln

<210> SEQ ID NO 10
<211> LENGTH: 564
<212> TYPE: PRT
<213> ORGANISM: Homo sapiens

<400> SEQUENCE: 10

Asn Val Ile Asp His Val Arg Asp Met Ala Ala Gly Leu His Ser
1               5                   10                  15

Asn Val Arg Leu Leu Ser Ser Leu Leu Leu Thr Met Ser Asn Asn
                20                  25                  30

Pro Glu Leu Phe Ser Pro Pro Gln Lys Tyr Gln Leu Leu Val Tyr His
                35                  40                  45

Ala Asp Ser Leu Phe His Asp Lys Glu Tyr Arg Asn Ala Val Ser Lys
50                  55                  60

Tyr Thr Met Ala Leu Gln Gln Lys Lys Ala Leu Ser Lys Thr Ser Lys
65                  70                  75                  80

Val Arg Pro Ser Thr Gly Asn Ser Ala Ser Thr Pro Gln Ser Gln Cys
                85                  90                  95

Leu Pro Ser Glu Ile Glu Val Lys Tyr Lys Met Ala Glu Cys Tyr Thr
                100                 105                 110

Met Leu Lys Gln Asp Lys Asp Ala Ile Ala Ile Leu Asp Gly Ile Pro
            115                 120                 125

Ser Arg Gln Arg Thr Pro Lys Ile Asn Met Met Leu Ala Asn Leu Tyr
130                 135                 140

Lys Lys Ala Gly Gln Glu Arg Pro Ser Val Thr Ser Tyr Lys Glu Val
145                 150                 155                 160

Leu Arg Gln Cys Pro Leu Ala Leu Asp Ala Ile Leu Gly Leu Leu Ser
                165                 170                 175

Leu Ser Val Lys Gly Ala Glu Val Ala Ser Met Thr Met Asn Val Ile
            180                 185                 190

Gln Thr Val Pro Asn Leu Asp Trp Leu Ser Val Trp Ile Lys Ala Tyr
        195                 200                 205

Ala Phe Val His Thr Gly Asp Asn Ser Arg Ala Ile Ser Thr Ile Cys
210                 215                 220

Ser Leu Glu Lys Lys Ser Leu Arg Asp Asn Val Asp Leu Leu Gly
225                 230                 235                 240

Ser Leu Ala Asp Leu Tyr Phe Arg Ala Gly Asp Asn Lys Asn Ser Val
                245                 250                 255

Leu Lys Phe Glu Gln Ala Gln Met Leu Asp Pro Tyr Leu Ile Lys Gly
            260                 265                 270

```
Met Asp Val Tyr Gly Tyr Leu Leu Ala Arg Glu Gly Arg Leu Glu Asp
        275                 280                 285

Val Glu Asn Leu Gly Cys Arg Leu Phe Asn Ile Ser Asp Gln His Ala
    290                 295                 300

Glu Pro Trp Val Val Ser Gly Cys His Ser Phe Tyr Ser Lys Arg Tyr
305                 310                 315                 320

Ser Arg Ala Leu Tyr Leu Gly Ala Lys Ala Ile Gln Leu Asn Ser Asn
                325                 330                 335

Ser Val Gln Ala Leu Leu Lys Gly Ala Ala Leu Arg Asn Met Gly
                340                 345                 350

Arg Val Gln Glu Ala Ile Ile His Phe Arg Glu Ala Ile Arg Leu Ala
                355                 360                 365

Pro Cys Arg Leu Asp Cys Tyr Glu Gly Leu Ile Glu Cys Tyr Leu Ala
            370                 375                 380

Ser Asn Ser Ile Arg Glu Ala Met Val Met Ala Asn Asn Val Tyr Lys
385                 390                 395                 400

Thr Leu Gly Ala Asn Ala Gln Thr Leu Thr Leu Ala Thr Val Cys
                405                 410                 415

Leu Glu Asp Pro Val Thr Gln Glu Lys Ala Lys Thr Leu Leu Asp Lys
            420                 425                 430

Ala Leu Thr Gln Arg Pro Asp Tyr Ile Lys Ala Val Val Lys Lys Ala
                435                 440                 445

Glu Leu Leu Ser Arg Glu Gln Lys Tyr Glu Asp Gly Ile Ala Leu Leu
                450                 455                 460

Arg Asn Ala Leu Ala Asn Gln Ser Asp Cys Val Leu His Arg Ile Leu
465                 470                 475                 480

Gly Asp Phe Leu Val Ala Val Asn Glu Tyr Gln Glu Ala Met Asp Gln
                485                 490                 495

Tyr Ser Ile Ala Leu Ser Leu Asp Pro Asn Asp Gln Lys Ser Leu Glu
                500                 505                 510

Gly Met Gln Lys Met Glu Lys Glu Glu Ser Pro Thr Asp Ala Thr Gln
            515                 520                 525

Glu Glu Asp Val Asp Met Glu Gly Ser Gly Glu Glu Gly Asp Leu
            530                 535                 540

Glu Gly Ser Asp Ser Glu Ala Ala Gln Trp Ala Asp Gln Glu Gln Trp
545                 550                 555                 560

Phe Gly Met Gln

<210> SEQ ID NO 11
<211> LENGTH: 564
<212> TYPE: PRT
<213> ORGANISM: Homo sapiens

<400> SEQUENCE: 11

Asn Val Ile Asp His Val Arg Asp Met Ala Ala Gly Leu His Ser
1               5                   10                  15

Asn Val Arg Leu Leu Ser Ser Leu Leu Leu Thr Met Ser Asn Asn Asn
                20                  25                  30

Pro Glu Leu Phe Ser Pro Pro Gln Lys Tyr Gln Leu Leu Val Tyr His
            35                  40                  45

Ala Asp Ser Leu Phe His Asp Lys Glu Tyr Arg Asn Ala Val Ser Lys
        50                  55                  60

Tyr Thr Met Ala Leu Gln Gln Lys Lys Ala Leu Ser Lys Thr Ser Lys
65              70                  75                  80
```

```
Val Arg Pro Ser Thr Gly Asn Ser Ala Ser Thr Pro Gln Ser Gln Cys
                85                  90                  95

Leu Pro Ser Glu Ile Glu Val Lys Tyr Lys Met Ala Glu Cys Tyr Thr
            100                 105                 110

Met Leu Lys Gln Asp Lys Asp Ala Ile Ala Ile Leu Asp Gly Ile Pro
        115                 120                 125

Ser Arg Gln Arg Thr Pro Lys Ile Asn Met Met Leu Ala Asn Leu Tyr
    130                 135                 140

Lys Lys Ala Gly Gln Glu Arg Pro Ser Val Thr Ser Tyr Lys Glu Val
145                 150                 155                 160

Leu Arg Gln Cys Pro Leu Ala Leu Asp Ala Ile Leu Gly Leu Leu Ser
                165                 170                 175

Leu Ser Val Lys Gly Ala Glu Val Ala Ser Met Thr Met Asn Val Ile
            180                 185                 190

Gln Thr Val Pro Asn Leu Asp Trp Leu Ser Val Trp Ile Lys Ala Tyr
        195                 200                 205

Ala Phe Val His Thr Gly Asp Asn Ser Arg Ala Ile Ser Thr Ile Cys
    210                 215                 220

Ser Leu Glu Lys Lys Ser Leu Arg Asp Asn Val Asp Leu Leu Gly
225                 230                 235                 240

Ser Leu Ala Asp Leu Tyr Phe Arg Ala Gly Asp Asn Lys Asn Ser Val
                245                 250                 255

Leu Lys Phe Glu Gln Ala Gln Met Leu Asp Pro Tyr Leu Ile Lys Gly
            260                 265                 270

Met Asp Val Tyr Gly Tyr Leu Leu Ala Arg Gly Arg Leu Glu Asp
        275                 280                 285

Val Glu Asn Leu Gly Cys Arg Leu Phe Asn Ile Ser Asp Gln His Ala
    290                 295                 300

Glu Pro Trp Val Val Ser Gly Cys His Ser Phe Tyr Ser Lys Arg Tyr
305                 310                 315                 320

Ser Arg Ala Leu Tyr Leu Gly Ala Lys Ala Ile Gln Leu Asn Ser Asn
                325                 330                 335

Ser Val Gln Ala Leu Leu Leu Lys Gly Ala Ala Leu Arg Asn Met Gly
            340                 345                 350

Arg Val Gln Glu Ala Ile Ile His Phe Arg Glu Ala Ile Arg Leu Ala
        355                 360                 365

Pro Cys Arg Leu Asp Cys Tyr Glu Gly Leu Ile Glu Cys Tyr Leu Ala
    370                 375                 380

Ser Asn Ser Ile Arg Glu Ala Met Val Met Ala Asn Asn Val Tyr Lys
385                 390                 395                 400

Thr Leu Gly Ala Asn Ala Gln Thr Leu Thr Leu Leu Ala Thr Val Cys
                405                 410                 415

Leu Glu Asp Pro Val Thr Gln Glu Lys Ala Lys Thr Leu Leu Asp Lys
            420                 425                 430

Ala Leu Thr Gln Arg Pro Asp Tyr Ile Lys Ala Val Val Lys Lys Ala
        435                 440                 445

Glu Leu Leu Ser Arg Glu Gln Lys Tyr Glu Asp Gly Ile Ala Leu Leu
    450                 455                 460

Arg Asn Ala Leu Ala Asn Gln Ser Asp Cys Val Leu His Arg Ile Leu
465                 470                 475                 480

Gly Asp Phe Leu Val Ala Val Asn Glu Tyr Gln Glu Ala Met Asp Gln
                485                 490                 495
```

```
Tyr Ser Ile Ala Leu Ser Leu Asp Pro Asn Asp Gln Lys Ser Leu Glu
            500                 505                 510

Gly Met Gln Lys Met Glu Lys Glu Ser Pro Thr Asp Ala Thr Gln
        515                 520                 525

Glu Glu Asp Val Asp Asp Met Glu Gly Ser Gly Glu Glu Gly Asp Leu
    530                 535                 540

Glu Gly Ser Asp Ser Glu Ala Ala Gln Trp Ala Asp Gln Glu Gln Trp
545                 550                 555                 560

Phe Gly Met Gln

<210> SEQ ID NO 12
<211> LENGTH: 565
<212> TYPE: PRT
<213> ORGANISM: Homo sapiens

<400> SEQUENCE: 12

Met Asn Val Ile Asp His Val Arg Asp Met Ala Ala Ala Gly Leu His
1               5                   10                  15

Ser Asn Val Arg Leu Leu Ser Ser Leu Leu Thr Met Ser Asn Asn
            20                  25                  30

Asn Pro Glu Leu Phe Ser Pro Pro Gln Lys Tyr Gln Leu Leu Val Tyr
        35                  40                  45

His Ala Asp Ser Leu Phe His Asp Lys Glu Tyr Arg Asn Ala Val Ser
    50                  55                  60

Lys Tyr Thr Met Ala Leu Gln Gln Lys Lys Ala Leu Ser Lys Thr Ser
65                  70                  75                  80

Lys Val Arg Pro Ser Thr Gly Asn Ser Ala Ser Thr Pro Gln Ser Gln
                85                  90                  95

Cys Leu Pro Ser Glu Ile Glu Val Lys Tyr Lys Met Ala Glu Cys Tyr
            100                 105                 110

Thr Met Leu Lys Gln Asp Lys Asp Ala Ile Ala Ile Leu Asp Gly Ile
        115                 120                 125

Pro Ser Arg Gln Arg Thr Pro Lys Ile Asn Met Met Leu Ala Asn Leu
    130                 135                 140

Tyr Lys Lys Ala Gly Gln Glu Arg Pro Ser Val Thr Ser Tyr Lys Glu
145                 150                 155                 160

Val Leu Arg Gln Cys Pro Leu Ala Leu Asp Ala Ile Leu Gly Leu Leu
                165                 170                 175

Ser Leu Ser Val Lys Gly Ala Glu Val Ala Ser Met Thr Met Asn Val
            180                 185                 190

Ile Gln Thr Val Pro Asn Leu Asp Trp Leu Ser Val Trp Ile Lys Ala
        195                 200                 205

Tyr Ala Phe Val His Thr Gly Asp Asn Ser Arg Ala Ile Ser Thr Ile
    210                 215                 220

Cys Ser Leu Glu Lys Lys Ser Leu Leu Arg Asp Asn Val Asp Leu Leu
225                 230                 235                 240

Gly Ser Leu Ala Asp Leu Tyr Phe Arg Ala Gly Asp Asn Lys Asn Ser
                245                 250                 255

Val Leu Lys Phe Glu Gln Ala Gln Met Leu Asp Pro Tyr Leu Ile Lys
            260                 265                 270

Gly Met Asp Val Tyr Gly Tyr Leu Leu Ala Arg Glu Gly Arg Leu Glu
        275                 280                 285

Asp Val Glu Asn Leu Gly Cys Arg Leu Phe Asn Ile Ser Asp Gln His
    290                 295                 300
```

```
Ala Glu Pro Trp Val Val Ser Gly Cys His Ser Phe Tyr Ser Lys Arg
305                 310                 315                 320

Tyr Ser Arg Ala Leu Tyr Leu Gly Ala Lys Ala Ile Gln Leu Asn Ser
            325                 330                 335

Asn Ser Val Gln Ala Leu Leu Lys Gly Ala Ala Leu Arg Asn Met
        340                 345                 350

Gly Arg Val Gln Glu Ala Ile Ile His Phe Arg Glu Ala Ile Arg Leu
        355                 360                 365

Ala Pro Cys Arg Leu Asp Cys Tyr Glu Gly Leu Ile Glu Cys Tyr Leu
        370                 375                 380

Ala Ser Asn Ser Ile Arg Glu Ala Met Val Ile Ala Asn Asn Val Tyr
385                 390                 395                 400

Lys Thr Leu Gly Ala Asn Ala Gln Thr Leu Thr Leu Ala Thr Val
            405                 410                 415

Cys Leu Glu Asp Pro Val Thr Gln Glu Lys Ala Lys Thr Leu Leu Asp
            420                 425                 430

Lys Ala Leu Thr Gln Arg Pro Asp Tyr Ile Lys Ala Val Val Lys Lys
            435                 440                 445

Ala Glu Leu Leu Ser Arg Glu Gln Lys Tyr Glu Asp Gly Ile Ala Leu
450                 455                 460

Leu Arg Asn Ala Leu Ala Asn Gln Ser Asp Cys Val Leu His Arg Ile
465                 470                 475                 480

Leu Gly Asp Phe Leu Val Ala Val Asn Glu Tyr Gln Glu Ala Met Asp
                485                 490                 495

Gln Tyr Ser Ile Ala Leu Ser Leu Asp Pro Asn Asp Gly Lys Ser Leu
            500                 505                 510

Glu Gly Met Gln Lys Met Glu Lys Glu Ser Pro Thr Asp Ala Thr
        515                 520                 525

Gln Glu Glu Asp Val Asp Asp Met Glu Gly Ser Gly Glu Glu Gly Asp
        530                 535                 540

Leu Glu Gly Ser Asp Ser Glu Ala Ala Gln Trp Ala Asp Gln Glu Gln
545                 550                 555                 560

Trp Phe Gly Met Gln
                565

<210> SEQ ID NO 13
<211> LENGTH: 563
<212> TYPE: PRT
<213> ORGANISM: Homo sapiens

<400> SEQUENCE: 13

Asn Val Ile Asp His Val Arg Asp Met Ala Ala Ala Gly Leu His Ser
1               5                   10                  15

Asn Val Arg Leu Leu Ser Ser Leu Leu Thr Met Ser Asn Asn Asn
            20                  25                  30

Pro Glu Leu Phe Ser Pro Pro Gln Lys Tyr Gln Leu Leu Val Tyr His
        35                  40                  45

Ala Asp Ser Leu Phe His Asp Lys Glu Tyr Arg Asn Ala Val Ser Lys
50                  55                  60

Tyr Thr Met Ala Leu Gln Gln Lys Lys Ala Leu Ser Lys Thr Ser Lys
65                  70                  75                  80

Val Arg Pro Ser Thr Gly Asn Ser Ala Ser Thr Pro Gln Ser Gln Cys
                85                  90                  95

Leu Pro Ser Glu Ile Glu Val Lys Tyr Lys Met Ala Glu Cys Tyr Thr
            100                 105                 110
```

```
Met Leu Lys Gln Asp Lys Asp Ala Ile Ala Ile Leu Asp Gly Ile Pro
            115                 120                 125

Ser Arg Gln Arg Thr Pro Lys Ile Asn Met Met Leu Ala Asn Leu Tyr
        130                 135                 140

Lys Lys Ala Gly Gln Glu Arg Pro Ser Val Thr Ser Tyr Lys Glu Val
145                 150                 155                 160

Leu Arg Gln Cys Pro Leu Ala Leu Asp Ala Ile Leu Gly Leu Leu Ser
                165                 170                 175

Leu Ser Val Lys Gly Ala Glu Val Ala Ser Met Thr Met Asn Val Ile
            180                 185                 190

Gln Thr Val Pro Asn Leu Asp Trp Leu Ser Val Trp Ile Lys Ala Tyr
        195                 200                 205

Ala Phe Val His Thr Gly Asp Asn Ser Arg Ala Ile Ser Thr Ile Cys
    210                 215                 220

Ser Leu Glu Lys Lys Ser Leu Leu Gln Asp Asn Val Asp Leu Leu Gly
225                 230                 235                 240

Ser Leu Ala Asp Leu Tyr Phe Arg Ala Gly Asp Asn Lys Asn Ser Val
                245                 250                 255

Leu Lys Phe Glu Gln Ala Gln Met Leu Asp Pro Tyr Leu Ile Lys Gly
            260                 265                 270

Met Asp Val Tyr Gly Tyr Leu Leu Ala Arg Glu Gly Arg Leu Glu Asp
        275                 280                 285

Val Glu Asn Leu Gly Cys Arg Leu Phe Asn Ile Ser Asp Gln His Ala
290                 295                 300

Glu Pro Trp Val Val Ser Gly Cys His Ser Phe Tyr Ser Lys Arg Tyr
305                 310                 315                 320

Ser Arg Ala Leu Tyr Leu Gly Ala Lys Ala Ile Gln Leu Asn Ser Asn
                325                 330                 335

Ser Val Gln Ala Leu Leu Leu Lys Gly Ala Ala Leu Arg Asn Met Gly
            340                 345                 350

Arg Val Gln Glu Ala Ile Ile His Phe Arg Glu Ala Ile Arg Leu Ala
        355                 360                 365

Pro Cys Arg Leu Asp Cys Tyr Glu Gly Leu Ile Glu Cys Tyr Leu Ala
    370                 375                 380

Ser Asn Ser Ile Arg Glu Ala Met Val Met Ala Asn Asn Val Tyr Lys
385                 390                 395                 400

Thr Leu Gly Ala Asn Ala Gln Thr Leu Thr Leu Leu Ala Thr Val Cys
                405                 410                 415

Leu Glu Asp Pro Val Thr Gln Glu Lys Ala Lys Thr Leu Leu Asp Lys
            420                 425                 430

Ala Leu Thr Gln Arg Pro Asp Tyr Ile Lys Ala Val Lys Lys Ala
        435                 440                 445

Glu Leu Leu Ser Arg Glu Gln Lys Tyr Glu Asp Gly Ile Ala Leu Leu
    450                 455                 460

Arg Asn Ala Leu Ala Asn Gln Ser Asp Cys Val Leu His Arg Ile Leu
465                 470                 475                 480

Gly Asp Phe Leu Val Ala Val Asn Glu Tyr Gln Glu Ala Met Asp Gln
                485                 490                 495

Tyr Ser Ile Ala Leu Ser Leu Asp Pro Asn Asp Gln Lys Ser Leu Glu
            500                 505                 510

Gly Met Gln Lys Met Glu Lys Glu Ser Pro Thr Asp Ala Thr Gln
        515                 520                 525
```

```
Glu Glu Asp Val Asp Asp Met Glu Gly Ser Gly Glu Gly Asp Leu
            530                 535                 540
Glu Gly Ser Asp Ser Glu Ala Ala Gln Trp Ala Asp Gln Glu Gln Trp
545                 550                 555                 560
Phe Gly Met
```

<210> SEQ ID NO 14
<211> LENGTH: 564
<212> TYPE: PRT
<213> ORGANISM: Homo sapiens

<400> SEQUENCE: 14

```
Met Asn Val Ile Asp His Val Arg Asp Met Ala Ala Gly Leu His
1               5                   10                  15
Ser Asn Val Arg Leu Leu Ser Ser Leu Leu Thr Met Ser Asn Asn
                20                  25                  30
Asn Pro Glu Leu Phe Ser Pro Pro Gln Lys Tyr Gln Leu Leu Val Tyr
                35                  40                  45
His Ala Asp Ser Leu Phe His Asp Lys Glu Tyr Arg Asn Ala Val Ser
        50                  55                  60
Lys Tyr Thr Met Ala Leu Gln Gln Lys Ala Leu Ser Lys Thr Ser
65                  70                  75                  80
Lys Val Arg Pro Ser Thr Gly Asn Ser Ala Ser Thr Pro Gln Ser Gln
                85                  90                  95
Cys Leu Pro Ser Glu Ile Glu Val Lys Tyr Lys Met Ala Glu Cys Tyr
                100                 105                 110
Thr Met Leu Lys Gln Asp Lys Asp Ala Ile Ala Ile Leu Asp Gly Ile
                115                 120                 125
Pro Ser Arg Gln Arg Thr Pro Lys Ile Asn Met Met Leu Ala Asn Leu
        130                 135                 140
Tyr Lys Lys Ala Gly Gln Glu Arg Pro Ser Val Thr Ser Tyr Lys Glu
145                 150                 155                 160
Val Leu Arg Gln Cys Pro Leu Ala Leu Asp Ala Ile Leu Gly Leu Leu
                165                 170                 175
Ser Leu Ser Val Lys Gly Ala Glu Val Ala Ser Met Thr Met Asn Val
                180                 185                 190
Ile Gln Thr Val Pro Asn Leu Asp Trp Leu Ser Val Trp Ile Lys Ala
                195                 200                 205
Tyr Ala Phe Val His Thr Gly Asp Asn Ser Arg Ala Ile Ser Thr Ile
        210                 215                 220
Cys Ser Leu Glu Lys Lys Ser Leu Leu Gln Asp Asn Val Asp Leu Leu
225                 230                 235                 240
Gly Ser Leu Ala Asp Leu Tyr Phe Arg Ala Gly Asp Asn Lys Asn Ser
                245                 250                 255
Val Leu Lys Phe Glu Gln Ala Gln Met Leu Asp Pro Tyr Leu Ile Lys
                260                 265                 270
Gly Met Asp Val Tyr Gly Tyr Leu Leu Ala Arg Glu Gly Arg Leu Glu
                275                 280                 285
Asp Val Glu Asn Leu Gly Cys Arg Leu Phe Asn Ile Ser Asp Gln His
        290                 295                 300
Ala Glu Pro Trp Val Val Ser Gly Cys His Ser Phe Tyr Ser Lys Arg
305                 310                 315                 320
Tyr Ser Arg Ala Leu Tyr Leu Gly Ala Lys Ala Ile Gln Leu Asn Ser
                325                 330                 335
```

```
Asn Ser Val Gln Ala Leu Leu Leu Lys Gly Ala Ala Leu Arg Asn Met
            340                 345                 350

Gly Arg Val Gln Glu Ala Ile Ile His Phe Arg Glu Ala Ile Arg Leu
        355                 360                 365

Ala Pro Cys Arg Leu Asp Cys Tyr Glu Gly Leu Ile Glu Cys Tyr Leu
370                 375                 380

Ala Ser Asn Ser Ile Arg Glu Ala Met Val Met Ala Asn Asn Val Tyr
385                 390                 395                 400

Lys Thr Leu Gly Ala Asn Ala Gln Thr Thr Leu Thr Leu Ala Thr Val
                405                 410                 415

Cys Leu Glu Asp Pro Val Thr Gln Glu Lys Ala Lys Thr Leu Leu Asp
            420                 425                 430

Lys Ala Leu Thr Gln Arg Pro Asp Tyr Ile Lys Ala Val Val Lys Lys
        435                 440                 445

Ala Glu Leu Leu Ser Arg Glu Gln Lys Tyr Glu Asp Gly Ile Ala Leu
    450                 455                 460

Leu Arg Asn Ala Leu Ala Asn Gln Ser Asp Cys Val Leu His Arg Ile
465                 470                 475                 480

Leu Gly Asp Phe Leu Val Ala Val Asn Glu Tyr Gln Glu Ala Met Asp
                485                 490                 495

Gln Tyr Ser Ile Ala Leu Ser Leu Asp Pro Asn Asp Gln Lys Ser Leu
            500                 505                 510

Glu Gly Met Gln Lys Met Glu Glu Ser Pro Thr Asp Ala Thr
        515                 520                 525

Gln Glu Glu Asp Val Asp Met Glu Gly Ser Glu Glu Gly Asp
    530                 535                 540

Leu Glu Gly Ser Asp Ser Glu Ala Ala Gln Trp Ala Asp Gln Glu Gln
545                 550                 555                 560

Trp Phe Gly Met

<210> SEQ ID NO 15
<211> LENGTH: 565
<212> TYPE: PRT
<213> ORGANISM: Homo sapiens

<400> SEQUENCE: 15

Met Asn Val Ile Asp His Val Arg Asp Met Ala Ala Gly Leu His
1               5                   10                  15

Ser Asn Val Arg Leu Leu Ser Ser Leu Leu Thr Met Ser Asn Asn
            20                  25                  30

Asn Pro Glu Leu Phe Ser Pro Gln Lys Tyr Gln Leu Val Tyr
        35                  40                  45

His Ala Asp Ser Leu Phe His Asp Lys Glu Tyr Arg Asn Ala Val Ser
    50                  55                  60

Lys Tyr Thr Met Ala Leu Gln Gln Lys Lys Ala Leu Ser Lys Thr Ser
65                  70                  75                  80

Lys Val Arg Pro Ser Thr Gly Asn Ser Ala Ser Thr Pro Gln Ser Gln
                85                  90                  95

Cys Leu Pro Ser Glu Ile Glu Val Lys Tyr Lys Met Ala Glu Cys Tyr
            100                 105                 110

Thr Met Leu Lys Gln Asp Lys Asp Ala Ile Ala Ile Leu Asp Gly Ile
        115                 120                 125

Pro Ser Arg Gln Arg Thr Pro Lys Ile Asn Met Met Leu Ala Asn Leu
    130                 135                 140
```

```
Tyr Lys Lys Ala Gly Arg Glu Arg Pro Ser Val Thr Ser Tyr Lys Glu
145                 150                 155                 160

Val Leu Arg Gln Cys Pro Leu Ala Leu Asp Ala Ile Leu Gly Leu Leu
            165                 170                 175

Ser Leu Ser Val Lys Gly Ala Glu Val Ala Ser Met Thr Met Asn Val
            180                 185                 190

Ile Gln Thr Val Pro Asn Leu Asp Trp Leu Ser Val Trp Ile Lys Ala
        195                 200                 205

Tyr Ala Phe Val His Thr Gly Asp Asn Ser Arg Ala Ile Ser Thr Ile
210                 215                 220

Cys Ser Leu Glu Lys Lys Ser Leu Leu Arg Asp Asn Val Asp Leu Leu
225                 230                 235                 240

Gly Ser Leu Ala Asp Leu Tyr Phe Arg Ala Gly Asp Asn Lys Asn Ser
            245                 250                 255

Val Leu Lys Phe Glu Gln Ala Gln Met Leu Asp Leu Tyr Leu Ile Lys
            260                 265                 270

Gly Met Asp Val Tyr Gly Tyr Leu Leu Ala Arg Glu Gly Arg Leu Glu
        275                 280                 285

Asp Val Glu Asn Leu Gly Cys Arg Leu Phe Asn Ile Ser Asp Gln His
        290                 295                 300

Ala Glu Pro Trp Val Val Ser Gly Cys His Ser Phe Tyr Ser Lys Arg
305                 310                 315                 320

Tyr Ser Arg Ala Leu Tyr Leu Gly Ala Lys Ala Ile Gln Leu Asn Ser
            325                 330                 335

Asn Ser Val Gln Ala Leu Leu Leu Lys Gly Ala Ala Leu Arg Asn Met
            340                 345                 350

Gly Arg Val Gln Glu Ala Ile Ile His Phe Arg Glu Ala Ile Arg Leu
        355                 360                 365

Ala Pro Cys Arg Leu Asp Cys Tyr Glu Gly Leu Ile Glu Cys Tyr Leu
        370                 375                 380

Ala Ser Asn Ser Ile Arg Glu Ala Met Val Met Ala Asn Asn Val Tyr
385                 390                 395                 400

Lys Thr Leu Gly Ala Asn Ala Gln Thr Leu Thr Leu Leu Ala Thr Val
            405                 410                 415

Cys Leu Glu Asp Pro Val Thr Gln Glu Lys Ala Lys Thr Leu Leu Asp
            420                 425                 430

Lys Ala Leu Thr Gln Arg Pro Asp Tyr Ile Lys Ala Val Val Lys Lys
        435                 440                 445

Ala Glu Leu Leu Ser Arg Glu Gln Lys Tyr Glu Asp Gly Ile Ala Leu
        450                 455                 460

Leu Arg Asn Ala Leu Ala Asn Gln Ser Asp Cys Val Leu His Arg Ile
465                 470                 475                 480

Leu Gly Asp Phe Leu Val Ala Val Asn Glu Tyr Gln Glu Ala Met Asp
            485                 490                 495

Gln Tyr Ser Ile Ala Leu Ser Leu Asp Pro Asn Asp Gln Lys Ser Leu
            500                 505                 510

Glu Gly Met Gln Lys Met Glu Lys Glu Glu Ser Pro Thr Asp Ala Thr
        515                 520                 525

Gln Glu Glu Asp Val Asp Met Glu Gly Ser Gly Glu Glu Gly Asp
        530                 535                 540

Leu Glu Gly Ser Asp Ser Glu Ala Ala Gln Trp Ala Asp Gln Glu Gln
545                 550                 555                 560

Trp Phe Gly Met Gln
```

-continued

565

<210> SEQ ID NO 16
<211> LENGTH: 565
<212> TYPE: PRT
<213> ORGANISM: Homo sapiens

<400> SEQUENCE: 16

Met Asn Val Ile Asp His Val Arg Asp Met Ala Ala Gly Leu His
1               5                  10                  15

Ser Asn Val Arg Leu Leu Ser Ser Leu Leu Thr Met Ser Asn Asn
            20                  25                  30

Asn Pro Glu Leu Phe Ser Pro Gln Lys Tyr Gln Leu Leu Val Tyr
            35                  40                  45

His Ala Asp Ser Leu Phe His Asp Lys Glu Tyr Arg Asn Ala Val Ser
            50                  55                  60

Lys Tyr Thr Met Ala Leu Gln Gln Lys Lys Ala Leu Ser Lys Thr Ser
65                  70                  75                  80

Lys Val Arg Pro Ser Thr Gly Asn Ser Ala Ser Thr Pro Gln Ser Gln
                85                  90                  95

Cys Leu Pro Ser Glu Ile Glu Val Lys Tyr Lys Met Ala Glu Cys Tyr
            100                 105                 110

Thr Met Leu Lys Gln Asp Lys Asp Ala Ile Ala Ile Leu Asp Gly Ile
            115                 120                 125

Pro Ser Arg Gln Arg Thr Pro Lys Ile Asn Met Met Leu Ala Asn Leu
130                 135                 140

Tyr Lys Lys Ala Gly Gln Glu Arg Pro Ser Val Thr Ser Tyr Lys Glu
145                 150                 155                 160

Val Leu Arg Gln Cys Pro Leu Ala Leu Asp Ala Ile Leu Gly Leu Leu
                165                 170                 175

Ser Leu Ser Val Lys Gly Ala Glu Val Ala Ser Met Thr Met Asn Val
            180                 185                 190

Ile Gln Thr Val Pro Asn Leu Asp Trp Leu Ser Val Trp Ile Lys Ala
            195                 200                 205

Tyr Ala Phe Val His Thr Gly Asp Asn Ser Arg Ala Ile Ser Thr Ile
            210                 215                 220

Cys Ser Leu Glu Lys Lys Ser Leu Leu Arg Asp Asn Val Asp Leu Leu
225                 230                 235                 240

Gly Ser Leu Ala Asp Leu Tyr Phe Arg Ala Gly Asp Asn Lys Asn Ser
                245                 250                 255

Val Leu Lys Phe Glu Gln Ala Gln Met Leu Asp Pro Tyr Leu Ile Lys
            260                 265                 270

Gly Met Asp Val Tyr Gly Tyr Leu Leu Ala Arg Glu Gly Arg Leu Glu
            275                 280                 285

Asp Val Glu Asn Leu Gly Cys Arg Leu Phe Asn Ile Ser Asp Gln His
            290                 295                 300

Ala Glu Pro Trp Val Val Ser Gly Cys His Ser Phe Tyr Ser Lys Arg
305                 310                 315                 320

Tyr Ser Arg Ala Leu Tyr Leu Gly Ala Lys Ala Ile Gln Leu Asn Ser
                325                 330                 335

Asn Ser Val Gln Ala Leu Leu Leu Lys Gly Ala Ala Leu Arg Asn Met
            340                 345                 350

Gly Arg Val Gln Glu Ala Ile Ile His Phe Arg Glu Ala Ile Arg Leu
            355                 360                 365

-continued

```
Ala Pro Cys Arg Leu Asp Cys Tyr Glu Gly Leu Ile Glu Cys Tyr Leu
    370                 375                 380
Ala Ser Asn Ser Ile Arg Glu Ala Met Val Met Ala Asn Asn Val Tyr
385                 390                 395                 400
Lys Thr Leu Gly Ala Asn Ala Gln Thr Leu Thr Leu Leu Ala Thr Val
                405                 410                 415
Cys Leu Glu Asp Pro Val Thr Gln Glu Lys Ala Lys Thr Leu Leu Asp
                420                 425                 430
Lys Ala Leu Thr Gln Arg Pro Asp Tyr Ile Lys Ala Val Lys Lys
                435                 440                 445
Ala Glu Leu Leu Ser Arg Glu Gln Lys Tyr Glu Asp Gly Ile Ala Leu
    450                 455                 460
Leu Arg Asn Ala Leu Ala Asn Gln Ser Asp Cys Val Leu His Arg Ile
465                 470                 475                 480
Leu Gly Asp Phe Leu Val Ala Val Asn Glu Tyr Gln Glu Ala Met Asp
                485                 490                 495
Gln Tyr Ser Ile Ala Leu Ser Leu Asp Pro Asn Asp Gln Lys Ser Leu
                500                 505                 510
Glu Gly Met Gln Lys Met Glu Lys Glu Glu Ser Pro Thr Asp Ala Thr
    515                 520                 525
Gln Glu Glu Asp Val Asp Asp Met Glu Gly Ser Gly Glu Glu Gly Asp
530                 535                 540
Leu Glu Gly Ser Asp Ser Glu Ala Ala Gln Trp Ala Asp Gln Glu Gln
545                 550                 555                 560
Trp Phe Gly Met Gln
                565
```

<210> SEQ ID NO 17
<211> LENGTH: 565
<212> TYPE: PRT
<213> ORGANISM: Homo sapiens
<400> SEQUENCE: 17

```
Met Asn Val Ile Asp His Val Arg Asp Met Ala Ala Ala Gly Leu His
1               5                   10                  15
Ser Asn Val Arg Leu Leu Ser Ser Leu Leu Thr Met Ser Asn Asn
                20                  25                  30
Asn Pro Glu Leu Phe Ser Pro Pro Gln Lys Tyr Gln Leu Leu Val Tyr
            35                  40                  45
His Ala Asp Ser Leu Phe His Asp Lys Glu Tyr Arg Asn Ala Val Ser
    50                  55                  60
Lys Tyr Thr Met Ala Leu Gln Gln Lys Lys Ala Leu Ser Lys Thr Ser
65              70                  75                  80
Lys Val Arg Pro Ser Thr Gly Asn Ser Ala Ser Thr Pro Gln Ser Gln
                85                  90                  95
Cys Leu Pro Ser Glu Ile Glu Val Lys Tyr Lys Met Ala Glu Cys Tyr
            100                 105                 110
Thr Met Leu Lys Gln Asp Lys Asp Ala Ile Ala Ile Leu Asp Gly Ile
        115                 120                 125
Pro Ser Arg Gln Arg Thr Pro Lys Ile Asn Met Met Leu Ala Asn Leu
    130                 135                 140
Tyr Lys Lys Ala Gly Arg Glu Arg Pro Ser Val Thr Ser Tyr Lys Glu
145                 150                 155                 160
Val Leu Arg Gln Cys Pro Leu Ala Leu Asp Ala Ile Leu Gly Leu Leu
                165                 170                 175
```

Ser Leu Ser Val Lys Gly Ala Glu Val Ala Ser Met Thr Met Asn Val
            180                 185                 190

Ile Gln Thr Val Pro Asn Leu Asp Trp Leu Ser Val Trp Ile Lys Ala
        195                 200                 205

Tyr Ala Phe Val His Thr Gly Asp Asn Ser Arg Ala Ile Ser Thr Ile
    210                 215                 220

Cys Ser Leu Glu Lys Lys Ser Leu Leu Arg Asp Asn Val Asp Leu Leu
225                 230                 235                 240

Gly Ser Leu Ala Asp Leu Tyr Phe Arg Ala Gly Asp Asn Lys Asn Ser
                245                 250                 255

Val Leu Lys Phe Glu Gln Ala Gln Met Leu Asp Leu Tyr Leu Ile Lys
            260                 265                 270

Gly Met Asp Val Tyr Gly Tyr Leu Leu Ala Arg Glu Gly Arg Leu Glu
        275                 280                 285

Asp Val Glu Asn Leu Gly Cys Arg Leu Phe Asn Ile Ser Asp Gln His
    290                 295                 300

Ala Glu Pro Trp Val Val Ser Gly Cys His Ser Phe Tyr Ser Lys Arg
305                 310                 315                 320

Tyr Ser Arg Ala Leu Tyr Leu Gly Ala Lys Ala Ile Gln Leu Asn Ser
                325                 330                 335

Asn Ser Val Gln Ala Leu Leu Leu Lys Gly Ala Ala Leu Arg Asn Met
            340                 345                 350

Gly Arg Val Gln Glu Ala Ile Ile His Phe Arg Glu Ala Ile Arg Leu
        355                 360                 365

Ala Pro Cys Arg Leu Asp Cys Tyr Glu Gly Leu Ile Glu Cys Tyr Leu
    370                 375                 380

Ala Ser Asn Ser Ile Arg Glu Ala Met Val Met Ala Asn Asn Val Tyr
385                 390                 395                 400

Lys Thr Leu Gly Ala Asn Ala Gln Thr Leu Thr Leu Leu Ala Thr Val
                405                 410                 415

Cys Leu Glu Asp Pro Val Thr Gln Glu Lys Ala Lys Thr Leu Leu Asp
            420                 425                 430

Lys Ala Leu Thr Gln Arg Pro Asp Tyr Ile Lys Ala Val Val Lys Lys
        435                 440                 445

Ala Glu Leu Leu Ser Arg Glu Gln Lys Tyr Glu Asp Gly Ile Ala Leu
    450                 455                 460

Leu Arg Asn Ala Leu Ala Asn Gln Ser Asp Cys Val Leu His Arg Ile
465                 470                 475                 480

Leu Gly Asp Phe Leu Val Ala Val Asn Glu Tyr Gln Glu Ala Met Asp
                485                 490                 495

Gln Tyr Ser Ile Ala Leu Ser Leu Asp Pro Asn Asp Gly Lys Ser Leu
            500                 505                 510

Glu Gly Met Gln Lys Met Glu Lys Glu Ser Pro Thr Asp Ala Thr
        515                 520                 525

Gln Glu Glu Asp Val Asp Asp Met Glu Gly Ser Gly Glu Glu Gly Asp
    530                 535                 540

Leu Glu Gly Ser Asp Ser Glu Ala Ala Gln Trp Ala Asp Gln Glu Gln
545                 550                 555                 560

Trp Phe Gly Met Gln
                565

<210> SEQ ID NO 18
<211> LENGTH: 314

```
<212> TYPE: PRT
<213> ORGANISM: Homo sapiens

<400> SEQUENCE: 18

Asp Asn Lys Asn Ser Val Leu Lys Phe Glu Gln Ala Gln Met Leu Asp
1               5                   10                  15

Pro Tyr Leu Ile Lys Gly Met Asp Val Tyr Gly Tyr Leu Leu Ala Arg
            20                  25                  30

Glu Gly Arg Leu Glu Asp Val Glu Asn Leu Gly Cys Arg Leu Phe Asn
        35                  40                  45

Ile Ser Asp Gln His Ala Glu Pro Trp Val Val Ser Gly Cys His Ser
    50                  55                  60

Phe Tyr Ser Lys Arg Tyr Ser Arg Ala Leu Tyr Leu Gly Ala Lys Ala
65                  70                  75                  80

Ile Gln Leu Asn Ser Asn Ser Val Gln Ala Leu Leu Lys Gly Ala
                85                  90                  95

Ala Leu Arg Asn Met Gly Arg Val Gln Glu Ala Ile Ile His Phe Arg
            100                 105                 110

Glu Ala Ile Arg Leu Ala Pro Cys Arg Leu Asp Cys Tyr Glu Gly Leu
        115                 120                 125

Ile Glu Cys Tyr Leu Ala Ser Asn Ser Ile Arg Glu Ala Met Val Met
130                 135                 140

Ala Asn Asn Val Tyr Lys Thr Leu Gly Ala Asn Ala Gln Thr Leu Thr
145                 150                 155                 160

Leu Leu Ala Thr Val Cys Leu Glu Asp Pro Val Thr Gln Glu Lys Ala
            165                 170                 175

Lys Thr Leu Leu Asp Lys Ala Leu Thr Gln Arg Pro Asp Tyr Ile Lys
        180                 185                 190

Ala Val Val Lys Lys Ala Glu Leu Leu Ser Arg Glu Gln Lys Tyr Glu
    195                 200                 205

Asp Gly Ile Ala Leu Leu Arg Asn Ala Leu Ala Asn Gln Ser Asp Cys
210                 215                 220

Val Leu His Arg Ile Leu Gly Asp Phe Leu Val Ala Val Asn Glu Tyr
225                 230                 235                 240

Gln Glu Ala Met Asp Gln Tyr Ser Ile Ala Leu Ser Leu Asp Pro Asn
            245                 250                 255

Asp Gln Lys Ser Leu Glu Gly Met Gln Lys Met Glu Lys Glu Glu Ser
        260                 265                 270

Pro Thr Asp Ala Thr Gln Glu Glu Asp Val Asp Asp Met Gly Gly Ser
    275                 280                 285

Gly Glu Glu Gly Asp Leu Glu Gly Ser Asp Ser Glu Ala Ala Gln Trp
290                 295                 300

Ala Asp Gln Glu Gln Trp Phe Gly Met Gln
305                 310

<210> SEQ ID NO 19
<211> LENGTH: 456
<212> TYPE: PRT
<213> ORGANISM: Homo sapiens

<400> SEQUENCE: 19

Glu Cys Tyr Thr Met Leu Lys Gln Asp Lys Asp Ala Ile Ala Ile Leu
1               5                   10                  15

Asp Gly Ile Pro Ser Arg Gln Arg Thr Pro Lys Ile Asn Met Met Leu
            20                  25                  30
```

```
Ala Asn Leu Tyr Lys Lys Ala Gly Gln Glu Arg Pro Ser Val Thr Ser
         35                  40                  45

Tyr Lys Glu Val Leu Arg Gln Cys Pro Leu Ala Leu Asp Ala Ile Leu
 50                  55                  60

Gly Leu Leu Ser Leu Ser Val Lys Gly Ala Glu Val Ala Ser Met Thr
 65                  70                  75                  80

Met Asn Val Ile Gln Thr Val Pro Asn Leu Asp Trp Leu Ser Val Trp
                 85                  90                  95

Ile Lys Ala Tyr Ala Phe Val His Thr Gly Asp Asn Ser Arg Ala Ile
                100                 105                 110

Ser Thr Ile Cys Ser Leu Glu Lys Lys Ser Leu Leu Arg Asp Asn Val
            115                 120                 125

Asp Leu Leu Gly Ser Leu Ala Asp Leu Tyr Phe Arg Ala Gly Asp Asn
130                 135                 140

Lys Asn Ser Val Leu Lys Phe Glu Gln Ala Gln Met Leu Asp Pro Tyr
145                 150                 155                 160

Leu Ile Lys Gly Met Asp Val Tyr Gly Tyr Leu Leu Ala Arg Glu Gly
                165                 170                 175

Arg Leu Glu Asp Val Glu Asn Leu Gly Cys Arg Leu Phe Asn Ile Ser
            180                 185                 190

Asp Gln His Ala Glu Pro Trp Val Val Ser Gly Cys His Ser Phe Tyr
        195                 200                 205

Ser Lys Arg Tyr Ser Arg Ala Leu Tyr Leu Gly Ala Lys Ala Ile Gln
        210                 215                 220

Leu Asn Ser Asn Ser Val Gln Ala Leu Leu Lys Gly Ala Ala Leu
225                 230                 235                 240

Arg Asn Met Gly Arg Val Gln Glu Ala Ile Ile His Phe Arg Glu Ala
                245                 250                 255

Ile Arg Leu Ala Pro Cys Arg Leu Asp Cys Tyr Glu Gly Leu Ile Glu
            260                 265                 270

Cys Tyr Leu Ala Ser Asn Ser Ile Arg Glu Ala Met Val Met Ala Asn
        275                 280                 285

Asn Val Tyr Lys Thr Leu Gly Ala Asn Ala Gln Thr Leu Thr Leu Leu
    290                 295                 300

Ala Thr Val Cys Leu Glu Asp Pro Val Thr Gln Glu Lys Ala Lys Thr
305                 310                 315                 320

Leu Leu Asp Lys Ala Leu Thr Gln Arg Pro Asp Tyr Ile Lys Ala Val
                325                 330                 335

Val Lys Lys Ala Glu Leu Leu Ser Arg Glu Gln Lys Tyr Glu Asp Gly
            340                 345                 350

Ile Ala Leu Leu Arg Asn Ala Leu Ala Asn Gln Ser Asp Cys Val Leu
        355                 360                 365

His Arg Ile Leu Gly Asp Phe Leu Val Ala Val Asn Glu Tyr Gln Glu
    370                 375                 380

Ala Met Asp Gln Tyr Ser Ile Ala Leu Ser Leu Asp Pro Asn Asp Gln
385                 390                 395                 400

Lys Ser Leu Glu Gly Met Gln Lys Met Glu Lys Glu Ser Pro Thr
                405                 410                 415

Asp Ala Thr Gln Glu Glu Asp Val Asp Asp Met Glu Gly Ser Gly Glu
            420                 425                 430

Glu Gly Asp Leu Glu Gly Ser Asp Ser Glu Ala Ala Gln Trp Ala Asp
        435                 440                 445

Gln Glu Gln Trp Phe Gly Met Gln
```

```
          450                 455
```

<210> SEQ ID NO 20
<211> LENGTH: 591
<212> TYPE: PRT
<213> ORGANISM: Homo sapiens

<400> SEQUENCE: 20

```
Met Val Pro Val Ala Val Thr Ala Ala Val Pro Val Leu Ser Ile
1               5                   10                  15

Asn Ser Asp Phe Ser Asp Leu Arg Glu Ile Lys Lys Gln Leu Leu
            20                  25                  30

Ile Ala Gly Leu Thr Arg Glu Arg Gly Leu Leu His Ser Ser Lys Trp
            35                  40                  45

Ser Ala Glu Leu Ala Phe Ser Leu Pro Ala Leu Pro Leu Ala Glu Leu
50                  55                  60

Gln Pro Pro Pro Ile Thr Glu Glu Asp Ala Gln Asp Met Asp Ala
65              70                  75                  80

Tyr Thr Leu Ala Lys Ala Tyr Phe Asp Val Lys Glu Tyr Asp Arg Ala
                85                  90                  95

Ala His Phe Leu His Gly Cys Asn Ser Lys Lys Ala Tyr Phe Leu Tyr
            100                 105                 110

Met Tyr Ser Arg Tyr Leu Ser Gly Glu Lys Lys Asp Asp Glu Thr
            115                 120                 125

Val Asp Ser Leu Gly Pro Leu Glu Lys Gly Gln Val Lys Asn Glu Ala
130                 135                 140

Leu Arg Glu Leu Arg Val Glu Leu Ser Lys Lys His Gln Ala Arg Glu
145                 150                 155                 160

Leu Asp Gly Phe Gly Leu Tyr Leu Tyr Gly Val Val Leu Arg Lys Leu
                165                 170                 175

Asp Leu Val Lys Glu Ala Ile Asp Val Phe Val Glu Ala Thr His Val
            180                 185                 190

Leu Pro Leu His Trp Gly Ala Trp Leu Glu Leu Cys Asn Leu Ile Thr
            195                 200                 205

Asp Lys Glu Met Leu Lys Phe Leu Ser Leu Pro Asp Thr Trp Met Lys
210                 215                 220

Glu Phe Phe Leu Ala His Ile Tyr Thr Glu Leu Gln Leu Ile Glu Glu
225                 230                 235                 240

Ala Leu Gln Lys Tyr Gln Asn Leu Ile Asp Val Gly Phe Ser Lys Ser
                245                 250                 255

Ser Tyr Ile Val Ser Gln Ile Ala Val Ala Tyr His Asn Ile Arg Asp
            260                 265                 270

Ile Asp Lys Ala Leu Ser Ile Phe Asn Glu Leu Arg Lys Gln Asp Pro
            275                 280                 285

Tyr Arg Ile Glu Asn Met Asp Thr Phe Ser Asn Leu Leu Tyr Val Arg
290                 295                 300

Ser Met Lys Ser Glu Leu Ser Tyr Leu Ala His Asn Leu Cys Glu Ile
305                 310                 315                 320

Asp Lys Tyr Arg Val Glu Thr Cys Cys Val Ile Gly Asn Tyr Tyr Ser
                325                 330                 335

Leu Arg Ser Gln His Glu Lys Ala Ala Leu Tyr Phe Gln Arg Ala Leu
            340                 345                 350

Lys Leu Asn Pro Arg Tyr Leu Gly Ala Trp Thr Leu Met Gly His Glu
            355                 360                 365
```

```
Tyr Met Glu Met Lys Asn Thr Ser Ala Ala Ile Gln Ala Tyr Arg His
    370             375                 380

Ala Ile Glu Val Asn Lys Arg Asp Tyr Arg Ala Trp Tyr Gly Leu Gly
385                 390                 395                 400

Gln Thr Tyr Glu Ile Leu Lys Met Pro Phe Tyr Cys Leu Tyr Tyr Tyr
                405                 410                 415

Arg Arg Ala His Gln Leu Arg Pro Asn Asp Ser Arg Met Leu Val Ala
                420                 425                 430

Leu Gly Glu Cys Tyr Glu Lys Leu Asn Gln Leu Val Glu Ala Lys Lys
            435                 440                 445

Cys Tyr Trp Arg Ala Tyr Ala Val Gly Asp Val Glu Lys Met Ala Leu
450                 455                 460

Val Lys Leu Ala Lys Leu His Glu Gln Leu Thr Glu Ser Glu Gln Ala
465                 470                 475                 480

Ala Gln Cys Tyr Ile Lys Tyr Ile Gln Asp Ile Tyr Ser Cys Gly Glu
                485                 490                 495

Ile Val Glu His Leu Glu Glu Ser Thr Ala Phe Arg Tyr Leu Ala Gln
                500                 505                 510

Tyr Tyr Phe Lys Cys Lys Leu Trp Asp Glu Ala Ser Thr Cys Ala Gln
                515                 520                 525

Lys Cys Cys Ala Phe Asn Asp Thr Arg Glu Glu Gly Lys Ala Leu Leu
            530                 535                 540

Arg Gln Ile Leu Gln Leu Arg Asn Gln Gly Glu Thr Pro Thr Thr Glu
545                 550                 555                 560

Val Pro Ala Pro Phe Phe Leu Pro Ala Ser Leu Ser Ala Asn Asn Thr
                565                 570                 575

Pro Thr Arg Arg Val Phe Pro Leu Asn Leu Ser Ser Val Thr Pro
                580                 585                 590

<210> SEQ ID NO 21
<211> LENGTH: 145
<212> TYPE: PRT
<213> ORGANISM: Homo sapiens

<400> SEQUENCE: 21

Met Val Pro Val Ala Val Thr Ala Ala Val Ala Pro Val Leu Ser Ile
1               5                   10                  15

Asn Ser Asp Phe Ser Asp Leu Arg Glu Ile Lys Lys Gln Leu Leu
            20                  25                  30

Ile Ala Gly Leu Thr Arg Glu Arg Gly Leu Leu His Ser Ser Lys Trp
            35                  40                  45

Ser Ala Glu Leu Ala Phe Ser Leu Pro Ala Leu Pro Leu Ala Glu Leu
50                  55                  60

Gln Pro Pro Pro Pro Ile Thr Glu Glu Asp Ala Gln Asp Met Asp Ala
65                  70                  75                  80

Tyr Thr Leu Ala Lys Ala Tyr Phe Asp Val Lys Glu Tyr Asp Arg Ala
                85                  90                  95

Ala His Phe Leu His Gly Cys Asn Ser Lys Lys Ala Tyr Phe Leu Tyr
                100                 105                 110

Met Tyr Ser Arg Tyr Leu Val Arg Ala Ile Leu Lys Cys His Ser Ala
            115                 120                 125

Phe Ser Glu Thr Ser Ile Phe Arg Thr Asn Gly Lys Val Lys Ser Phe
        130                 135                 140

Lys
145
```

<210> SEQ ID NO 22
<211> LENGTH: 145
<212> TYPE: PRT
<213> ORGANISM: Homo sapiens

<400> SEQUENCE: 22

Met Val Pro Val Ala Val Thr Ala Ala Val Ala Pro Val Leu Ser Ile
1               5                   10                  15

Asn Ser Asp Phe Ser Asp Leu Arg Glu Ile Lys Lys Gln Leu Leu Leu
            20                  25                  30

Ile Ala Gly Leu Thr Arg Glu Arg Gly Leu Leu His Ser Ser Lys Trp
        35                  40                  45

Ser Ala Glu Leu Ala Phe Ser Leu Pro Ala Leu Pro Leu Ala Glu Leu
    50                  55                  60

Gln Pro Pro Pro Ile Thr Glu Glu Asp Ala Gln Asp Met Asp Ala
65                  70                  75                  80

Tyr Thr Leu Ala Lys Ala Tyr Phe Asp Val Lys Glu Tyr Asp Arg Ala
                85                  90                  95

Ala His Phe Leu His Gly Cys Asn Ser Lys Lys Ala Tyr Phe Leu Tyr
            100                 105                 110

Met Tyr Ser Arg Tyr Leu Val Arg Ala Ile Leu Lys Cys His Ser Ala
        115                 120                 125

Phe Ser Glu Thr Ser Ile Phe Arg Thr Asn Gly Lys Val Lys Ser Phe
    130                 135                 140

Lys
145

<210> SEQ ID NO 23
<211> LENGTH: 591
<212> TYPE: PRT
<213> ORGANISM: Homo sapiens

<400> SEQUENCE: 23

Met Val Pro Val Ala Val Thr Ala Ala Val Ala Pro Val Leu Ser Ile
1               5                   10                  15

Asn Ser Asp Phe Ser Asp Leu Arg Glu Ile Lys Lys Gln Leu Leu Leu
            20                  25                  30

Ile Ala Gly Leu Thr Arg Glu Arg Gly Leu Leu His Ser Ser Lys Trp
        35                  40                  45

Ser Ala Glu Leu Ala Phe Ser Leu Pro Ala Leu Pro Leu Ala Glu Leu
    50                  55                  60

Gln Pro Pro Pro Ile Thr Glu Glu Asp Ala Gln Asp Met Asp Ala
65                  70                  75                  80

Tyr Thr Leu Ala Lys Ala Tyr Phe Asp Val Lys Glu Tyr Asp Arg Ala
                85                  90                  95

Ala His Phe Leu His Gly Cys Asn Ser Lys Lys Ala Tyr Phe Leu Tyr
            100                 105                 110

Met Tyr Ser Arg Tyr Leu Ser Gly Glu Lys Lys Lys Asp Asp Glu Thr
        115                 120                 125

Val Asp Ser Leu Gly Pro Leu Glu Lys Gly Gln Val Lys Asn Glu Ala
    130                 135                 140

Leu Arg Glu Leu Arg Val Glu Leu Ser Lys Lys His Gln Ala Arg Glu
145                 150                 155                 160

Leu Asp Gly Phe Gly Leu Tyr Leu Tyr Gly Val Val Leu Arg Lys Leu
                165                 170                 175

```
Asp Leu Val Lys Glu Ala Ile Asp Val Phe Glu Ala Thr His Val
            180                 185                 190

Leu Pro Leu His Trp Gly Ala Trp Leu Glu Leu Cys Asn Leu Ile Thr
            195                 200                 205

Asp Lys Glu Met Leu Lys Phe Leu Ser Leu Pro Asp Thr Trp Met Lys
210                 215                 220

Glu Phe Phe Leu Ala His Ile Tyr Thr Glu Leu Gln Leu Ile Glu Glu
225                 230                 235                 240

Ala Leu Gln Lys Tyr Gln Asn Leu Ile Asp Val Gly Phe Ser Lys Ser
            245                 250                 255

Ser Tyr Ile Val Ser Gln Ile Ala Val Ala Tyr His Asn Ile Arg Asp
            260                 265                 270

Ile Asp Lys Ala Leu Ser Ile Phe Asn Glu Leu Arg Lys Gln Asp Pro
            275                 280                 285

Tyr Arg Ile Glu Asn Met Asp Thr Phe Ser Asn Leu Leu Tyr Val Arg
            290                 295                 300

Ser Met Lys Ser Glu Leu Ser Tyr Leu Ala His Asn Leu Cys Glu Ile
305                 310                 315                 320

Asp Lys Tyr Arg Val Glu Thr Cys Cys Val Ile Gly Asn Tyr Tyr Ser
            325                 330                 335

Leu Arg Ser Gln His Glu Lys Ala Ala Leu Tyr Phe Gln Arg Ala Leu
            340                 345                 350

Lys Leu Asn Pro Arg Tyr Leu Gly Ala Trp Thr Leu Met Gly His Glu
            355                 360                 365

Tyr Met Glu Met Lys Asn Thr Ser Ala Ala Ile Gln Ala Tyr Arg His
            370                 375                 380

Ala Ile Glu Val Asn Lys Arg Asp Tyr Arg Ala Trp Tyr Gly Leu Gly
385                 390                 395                 400

Gln Thr Tyr Glu Ile Leu Lys Met Pro Phe Tyr Cys Leu Tyr Tyr Tyr
            405                 410                 415

Arg Arg Ala His Gln Leu Arg Pro Asn Asp Ser Arg Met Leu Val Ala
            420                 425                 430

Leu Gly Glu Cys Tyr Glu Lys Leu Asn Gln Leu Val Glu Ala Lys Lys
            435                 440                 445

Cys Tyr Trp Arg Ala Tyr Ala Val Gly Asp Val Glu Lys Met Ala Leu
450                 455                 460

Val Lys Leu Ala Lys Leu His Glu Gln Leu Thr Glu Ser Glu Gln Ala
465                 470                 475                 480

Ala Gln Cys Tyr Ile Lys Tyr Ile Gln Asp Ile Tyr Ser Cys Gly Glu
            485                 490                 495

Ile Val Glu His Leu Glu Glu Ser Thr Ala Phe Arg Tyr Leu Ala Gln
            500                 505                 510

Tyr Tyr Phe Lys Cys Lys Leu Trp Asp Glu Ala Ser Thr Cys Ala Gln
            515                 520                 525

Lys Cys Cys Ala Phe Asn Asp Thr Arg Glu Glu Gly Lys Ala Leu Leu
            530                 535                 540

Arg Gln Ile Leu Gln Leu Arg Asn Gln Gly Glu Thr Pro Thr Thr Glu
545                 550                 555                 560

Val Pro Ala Pro Phe Phe Leu Pro Ala Ser Leu Ser Ala Asn Asn Thr
            565                 570                 575

Pro Thr Arg Arg Val Ser Pro Leu Asn Leu Ser Ser Val Thr Pro
            580                 585                 590
```

<210> SEQ ID NO 24
<211> LENGTH: 597
<212> TYPE: PRT
<213> ORGANISM: Homo sapiens

<400> SEQUENCE: 24

Met Ala Ala Ser Thr Ser Met Val Pro Val Ala Val Thr Ala Ala Val
1               5                   10                  15

Ala Pro Val Leu Ser Ile Asn Ser Asp Phe Ser Asp Leu Arg Glu Ile
                20                  25                  30

Lys Lys Gln Leu Leu Leu Ile Ala Gly Leu Thr Arg Glu Arg Gly Leu
            35                  40                  45

Leu His Ser Ser Lys Trp Ser Ala Glu Leu Ala Phe Ser Leu Pro Ala
    50                  55                  60

Leu Pro Leu Ala Glu Leu Gln Pro Pro Pro Ile Thr Glu Glu Asp
65                  70                  75                  80

Ala Gln Asp Met Asp Ala Tyr Thr Leu Ala Lys Ala Tyr Phe Asp Val
                85                  90                  95

Lys Glu Tyr Asp Arg Ala Ala His Phe Leu His Gly Cys Asn Ser Lys
                100                 105                 110

Lys Ala Tyr Phe Leu Tyr Met Tyr Ser Arg Tyr Leu Ser Gly Glu Lys
            115                 120                 125

Lys Lys Asp Asp Glu Thr Val Asp Ser Leu Gly Pro Leu Glu Lys Gly
130                 135                 140

Gln Val Lys Asn Glu Ala Leu Arg Glu Leu Arg Val Glu Leu Ser Lys
145                 150                 155                 160

Lys His Gln Ala Arg Glu Leu Asp Gly Phe Gly Leu Tyr Leu Tyr Gly
                165                 170                 175

Val Val Leu Arg Lys Leu Asp Leu Val Lys Glu Ala Ile Asp Val Phe
            180                 185                 190

Val Glu Ala Thr His Val Leu Pro Leu His Trp Gly Ala Trp Leu Glu
        195                 200                 205

Leu Cys Asn Leu Ile Thr Asp Lys Glu Met Leu Lys Phe Leu Ser Leu
    210                 215                 220

Pro Asp Thr Trp Met Lys Glu Phe Phe Leu Ala His Ile Tyr Thr Glu
225                 230                 235                 240

Leu Gln Leu Ile Glu Glu Ala Leu Gln Lys Tyr Gln Asn Leu Ile Asp
                245                 250                 255

Val Gly Phe Ser Lys Ser Ser Tyr Ile Val Ser Gln Ile Ala Val Ala
            260                 265                 270

Tyr His Asn Ile Arg Asp Ile Asp Lys Ala Leu Ser Ile Phe Asn Glu
        275                 280                 285

Leu Arg Lys Gln Asp Pro Tyr Arg Ile Glu Asn Met Asp Thr Phe Ser
    290                 295                 300

Asn Leu Leu Tyr Val Arg Ser Met Lys Ser Glu Leu Ser Tyr Leu Ala
305                 310                 315                 320

His Asn Leu Cys Glu Ile Asp Lys Tyr Arg Val Glu Thr Cys Cys Val
                325                 330                 335

Ile Gly Asn Tyr Tyr Ser Leu Arg Ser Gln His Glu Lys Ala Ala Leu
            340                 345                 350

Tyr Phe Gln Arg Ala Leu Lys Leu Asn Pro Arg Tyr Leu Gly Ala Trp
        355                 360                 365

Thr Leu Met Gly His Glu Tyr Met Glu Met Lys Asn Thr Ser Ala Ala
    370                 375                 380

```
Ile Gln Ala Tyr Arg His Ala Ile Glu Val Asn Lys Arg Asp Tyr Arg
385                 390                 395                 400

Ala Trp Tyr Gly Leu Gly Gln Thr Tyr Glu Ile Leu Lys Met Pro Phe
                405                 410                 415

Tyr Cys Leu Tyr Tyr Arg Ala His Gln Leu Arg Pro Asn Asp
            420                 425                 430

Ser Arg Met Leu Val Ala Leu Gly Glu Cys Tyr Glu Lys Leu Asn Gln
            435                 440                 445

Leu Val Glu Ala Lys Lys Cys Tyr Trp Arg Ala Tyr Ala Val Gly Asp
450                 455                 460

Val Glu Lys Met Ala Leu Val Lys Leu Ala Lys Leu His Glu Gln Leu
465                 470                 475                 480

Thr Glu Ser Glu Gln Ala Ala Gln Cys Tyr Ile Lys Tyr Ile Gln Asp
                485                 490                 495

Ile Tyr Ser Cys Gly Glu Ile Val Glu His Leu Glu Glu Ser Thr Ala
            500                 505                 510

Phe Arg Tyr Leu Ala Gln Tyr Tyr Phe Lys Cys Lys Leu Trp Asp Glu
        515                 520                 525

Ala Ser Thr Cys Ala Gln Lys Cys Cys Ala Phe Asn Asp Thr Arg Glu
530                 535                 540

Glu Gly Lys Ala Leu Leu Arg Gln Ile Leu Gln Leu Arg Asn Gln Gly
545                 550                 555                 560

Glu Thr Pro Thr Thr Glu Val Pro Ala Pro Phe Leu Pro Ala Ser
                565                 570                 575

Leu Ser Ala Asn Asn Thr Pro Thr Arg Arg Val Ser Pro Leu Asn Leu
            580                 585                 590

Ser Ser Val Thr Pro
        595

<210> SEQ ID NO 25
<211> LENGTH: 591
<212> TYPE: PRT
<213> ORGANISM: Homo sapiens

<400> SEQUENCE: 25

Met Val Pro Val Ala Val Thr Ala Ala Val Ala Pro Val Leu Ser Ile
1               5                   10                  15

Asn Ser Asp Phe Ser Asp Leu Arg Glu Ile Lys Lys Gln Leu Leu Leu
            20                  25                  30

Ile Ala Gly Leu Thr Arg Glu Arg Gly Leu Leu His Ser Ser Lys Trp
        35                  40                  45

Ser Ala Glu Leu Ala Phe Ser Leu Pro Ala Leu Pro Leu Ala Glu Leu
    50                  55                  60

Gln Pro Pro Pro Ile Thr Glu Glu Asp Ala Gln Asp Met Asp Ala
65                  70                  75                  80

Tyr Thr Leu Ala Lys Ala Tyr Phe Asp Val Lys Glu Tyr Asp Arg Ala
                85                  90                  95

Ala His Phe Leu His Gly Cys Asn Ser Lys Lys Ala Tyr Phe Leu Tyr
            100                 105                 110

Met Tyr Ser Arg Tyr Leu Ser Gly Glu Lys Lys Asp Asp Glu Thr
        115                 120                 125

Val Asp Ser Leu Gly Pro Leu Glu Lys Gly Gln Val Lys Asn Glu Ala
    130                 135                 140

Leu Arg Glu Leu Arg Val Glu Leu Ser Lys Lys His Gln Ala Arg Glu
```

```
                145                 150                 155                 160
Leu Asp Gly Phe Gly Leu Tyr Leu Tyr Gly Val Val Leu Arg Lys Leu
                    165                 170                 175

Asp Leu Val Lys Glu Ala Ile Asp Val Phe Val Glu Ala Thr His Val
            180                 185                 190

Leu Pro Leu His Trp Gly Ala Trp Leu Glu Leu Cys Asn Leu Ile Thr
                195                 200                 205

Asp Lys Glu Met Leu Lys Phe Leu Ser Leu Pro Asp Thr Trp Met Lys
        210                 215                 220

Glu Phe Phe Leu Ala His Ile Tyr Thr Glu Leu Gln Leu Ile Glu Glu
225                 230                 235                 240

Ala Leu Gln Lys Tyr Gln Asn Leu Ile Asp Val Gly Phe Ser Lys Ser
                245                 250                 255

Ser Tyr Ile Val Ser Gln Ile Ala Val Ala Tyr His Asn Ile Arg Asp
                    260                 265                 270

Ile Asp Lys Ala Leu Ser Ile Phe Asn Glu Leu Arg Lys Gln Asp Pro
                275                 280                 285

Tyr Arg Ile Glu Asn Met Asp Thr Phe Ser Asn Leu Leu Tyr Val Arg
            290                 295                 300

Ser Met Lys Ser Glu Leu Ser Tyr Leu Ala His Asn Leu Cys Glu Ile
305                 310                 315                 320

Asp Lys Tyr Arg Val Glu Thr Cys Cys Val Ile Gly Asn Tyr Tyr Ser
                    325                 330                 335

Leu Arg Ser Gln His Glu Lys Ala Ala Leu Tyr Phe Gln Arg Ala Leu
                340                 345                 350

Lys Leu Asn Pro Arg Tyr Leu Gly Ala Trp Thr Leu Met Gly His Glu
            355                 360                 365

Tyr Met Glu Met Lys Asn Thr Ser Ala Ala Ile Gln Ala Tyr Arg His
        370                 375                 380

Ala Ile Glu Val Asn Lys Arg Asp Tyr Arg Ala Trp Tyr Gly Leu Gly
385                 390                 395                 400

Gln Thr Tyr Glu Ile Leu Lys Met Pro Phe Tyr Cys Leu Tyr Tyr Tyr
                    405                 410                 415

Arg Arg Ala His Gln Leu Arg Pro Asn Asp Ser Arg Met Leu Val Ala
                420                 425                 430

Leu Gly Glu Cys Tyr Lys Leu Asn Gln Leu Val Glu Ala Lys Lys
            435                 440                 445

Cys Tyr Trp Arg Ala Tyr Ala Val Gly Asp Val Glu Lys Met Ala Leu
        450                 455                 460

Val Lys Leu Ala Lys Leu His Glu Gln Leu Thr Glu Ser Glu Gln Ala
465                 470                 475                 480

Ala Gln Cys Tyr Ile Lys Tyr Ile Gln Asp Ile Tyr Ser Cys Gly Glu
                    485                 490                 495

Ile Val Glu His Leu Glu Glu Ser Thr Ala Phe Arg Tyr Leu Ala Gln
                500                 505                 510

Tyr Tyr Phe Lys Cys Lys Leu Trp Asp Glu Ala Ser Thr Cys Ala Gln
            515                 520                 525

Lys Cys Cys Ala Phe Asn Asp Thr Arg Glu Gly Lys Ala Leu Leu
        530                 535                 540

Arg Gln Ile Leu Gln Leu Arg Asn Gln Gly Glu Thr Pro Thr Thr Glu
545                 550                 555                 560

Val Pro Ala Pro Phe Phe Leu Pro Ala Ser Leu Ser Ala Asn Asn Thr
                    565                 570                 575
```

```
Pro Thr Arg Arg Val Ser Pro Leu Asn Leu Ser Ser Val Thr Pro
            580                 585                 590

<210> SEQ ID NO 26
<211> LENGTH: 8
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid

<400> SEQUENCE: 26

Asp Arg Phe Tyr Ile Pro Xaa Arg
1               5
```